(12) United States Patent
Huang et al.

(10) Patent No.: US 11,518,754 B2
(45) Date of Patent: Dec. 6, 2022

(54) RADIOLABELED PHARMACEUTICALS AND METHODS OF MAKING AND USING SAME

(71) Applicant: YALE UNIVERSITY, New Haven, CT (US)

(72) Inventors: Yiyun Huang, Madison, CT (US);
Zhengxin Cai, Cheshire, CT (US);
Songye Li, New Haven, CT (US);
Nabeel Nabulsi, Milford, CT (US);
Richard Carson, Guilford, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 16/486,444

(22) PCT Filed: Feb. 15, 2018

(86) PCT No.: PCT/US2018/018388
§ 371 (c)(1),
(2) Date: Aug. 15, 2019

(87) PCT Pub. No.: WO2018/152339
PCT Pub. Date: Aug. 23, 2018

(65) Prior Publication Data
US 2020/0010447 A1 Jan. 9, 2020

Related U.S. Application Data

(60) Provisional application No. 62/460,541, filed on Feb. 17, 2017.

(51) Int. Cl.
| | | |
|---|---|---|
| C07D 401/06 | (2006.01) |
| A61K 51/04 | (2006.01) |
| C07D 403/06 | (2006.01) |
| A61K 9/00 | (2006.01) |

(52) U.S. Cl.
CPC ........ *C07D 401/06* (2013.01); *A61K 51/0446* (2013.01); *A61K 51/0455* (2013.01); *C07D 403/06* (2013.01); *A61K 9/0019* (2013.01); *C07B 2200/05* (2013.01)

(58) Field of Classification Search
None
See application file for complete search history.

(56) References Cited

U.S. PATENT DOCUMENTS

2008/0292548 A1 11/2008 Lehmann et al.
2013/0156700 A1 6/2013 Marik et al.

FOREIGN PATENT DOCUMENTS

WO 2013038153 A1 3/2013

OTHER PUBLICATIONS

Mercier et al. Discovery of heterocyclic nonacetamide synaptic vesicle protein 2A (SV2A) ligands with single-digit nanomolar potency: opening avenues towards the first SV2A positron emission tomography (PET) ligands. 2014 ChemMedChem. 9: 693-698. (Year: 2014).*
International Search Report and Written Opinion for PCT International Application No. PCT/US2018/018388 dated Apr. 30, 2018.
Finnema, et al., "Imaging synaptic density in the living human brain", Sci Transl Med. 8(348), Jul. 2016, 348ra96.
Mercier, et al., "Discovery of heterocyclic nonacetamide synaptic vesicle protein 2A (SV2A) ligands with single-digit Tanomolar potency: opening avenues towards the first SV2A positron emission tomography (PET) ligands", ChemMedChem. 9(4), Apr. 2014, 693-698.
Warnier, et al., "Enabling Efficient Positron Emission Tomography (PET) Imaging of Synaptic Vesicle Glycoprotein 2A (SV2A) with a Robust and One-Step Radiosynthesis of a Highly Potent 18 F-Labeled Ligand ([ 18 F]UCB-H)", J Med Chem. 59(19), Oct. 2016, 8955-8966.
Extended European Search Report for European Patent Application No. 18753847.5 dated Nov. 30, 2020.
Bretin, et al., "Biodistribution and Radiation Dosimetry for the Novel SV2A Radiotracer [(18)F]UCB-H: First-in-Human Study", Mol Imaging Biol. 17(4), Aug. 2015, 557-564.
Bretin, et al., "Preclinical radiation dosimetry for the novel SV2A radiotracer [18F]UCB-H", EJNMMI Res. 3(1), May 2013, 35.
Estrada, et al., "[(11)C]UCB-A, a novel PET tracer for synaptic vesicle protein 2A", Nucl Med Biol. 43(6), Jun. 2016, 325-332.
Menten-Dedoyart, et al., "Development and Validation of a New Mouse Model to Investigate the Role of SV2A in Epilepsy", PLoS One. 11(11), Nov. 2016, e0166525.
Morris, "Brain imaging: Synaptic density directly visualized in human brains", Nat Rev Neurol. 12(9):494, Sep. 2016, 494.
Nabulsi, et al., "[11 C]UCB-J: A novel PET tracer for imaging the synaptic vesicle glycoprotein 2A (SV2A)", J. Nucl. Med. vol. 55, supplement 1 355; URL:http://jnm.snmjournals.org/content/55/supplement_ 1 /355 [retrieved on Nov. 16, 2020], May 2014, Abstract only.
Nabulsi, et al., "Synthesis and Preclinical Evaluation of 11C-UCB-J as a PET Tracer for Imaging the Synaptic Vesicle Glycoprotein 2A in the Brain", J Nucl Med. 57(5), May 2016, 777-784.
Nicolas, et al., "Brivaracetam, a selective high-affinity synaptic vesicle protein 2A (SV2A) ligand with preclinical evidence of high brain permeability and fast onset of action", Epilepsia 57(2), Feb. 2016, 201-209.
Warnock, et al., "Evaluation of 18F-UCB-H as a novel PET tracer for synaptic vesicle protein 2A in the brain", J Nucl Med. 55(8), Aug. 2014, 1336-1341.

(Continued)

*Primary Examiner* — Jennifer Lamberski
(74) *Attorney, Agent, or Firm* — Saul Ewing Arnstein & Lehr LLP; Kathryn Doyle; Domingos J. Silva

(57) ABSTRACT

In one aspect, the invention comprises compounds that bind to the synaptic vesicle protein SV2A and that can be useful as radiotracers for positron emission tomography. In another aspect, the invention comprises methods of imaging the brain, measuring synaptic density or diagnosing neurological diseases such as Alzheimer's disease, psychiatric disorders such as depression, and metabolic disorders such as diabetes comprising detecting the compounds of the invention by positron emission tomography (PET).

20 Claims, 16 Drawing Sheets

(56) References Cited

OTHER PUBLICATIONS

Zheng, et al., "Synthesis and evaluation of 18F-UCB-H, a novel PET imaging tracer for the synaptic vesicle protein 2A", Journal of Nuclear Medicine, vol. 55, Issue supplement 1; URL:http://jnm.snmjournals.org/content/55/supplement_1/1792 [retrieved on Nov. 16, 2020], May 2014, Abstract only.

* cited by examiner

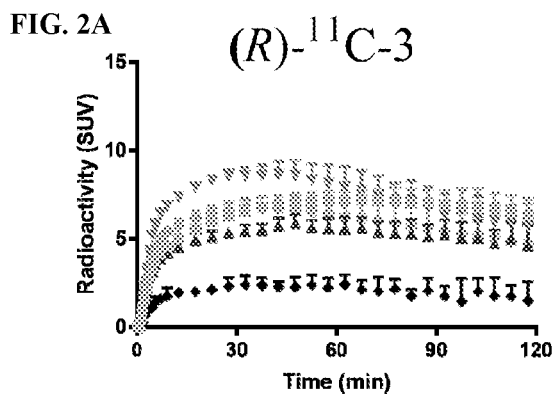
FIG. 2A  $(R)$-$^{11}$C-3
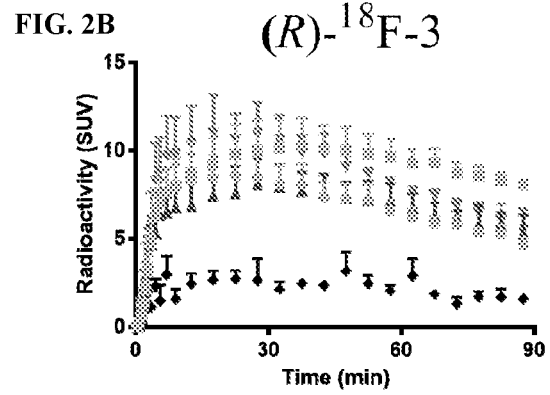
FIG. 2B  $(R)$-$^{18}$F-3
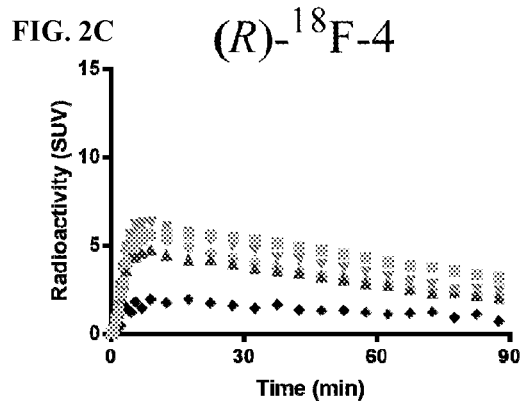
FIG. 2C  $(R)$-$^{18}$F-4
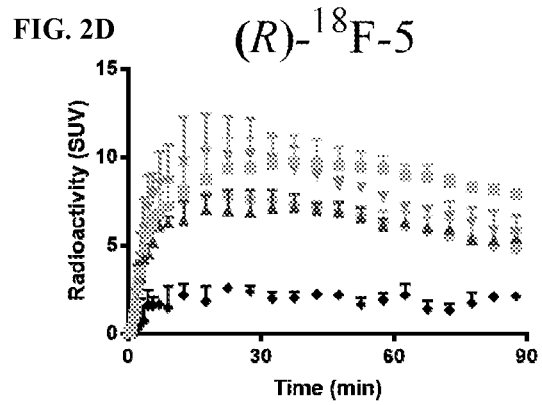
FIG. 2D  $(R)$-$^{18}$F-5
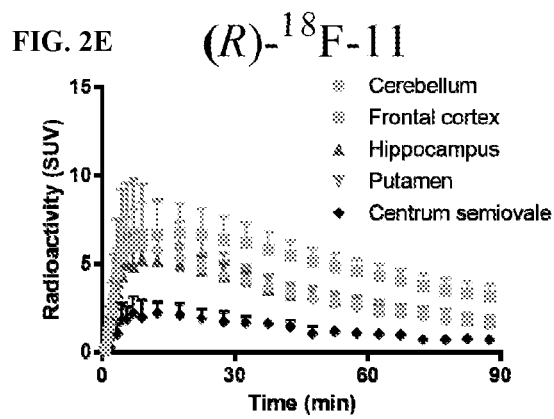
FIG. 2E  $(R)$-$^{18}$F-11

- Insular cortex
- Frontal cortex
- Thalamus
- Centrum semiovale
- Plasma
— Fit with 1T model

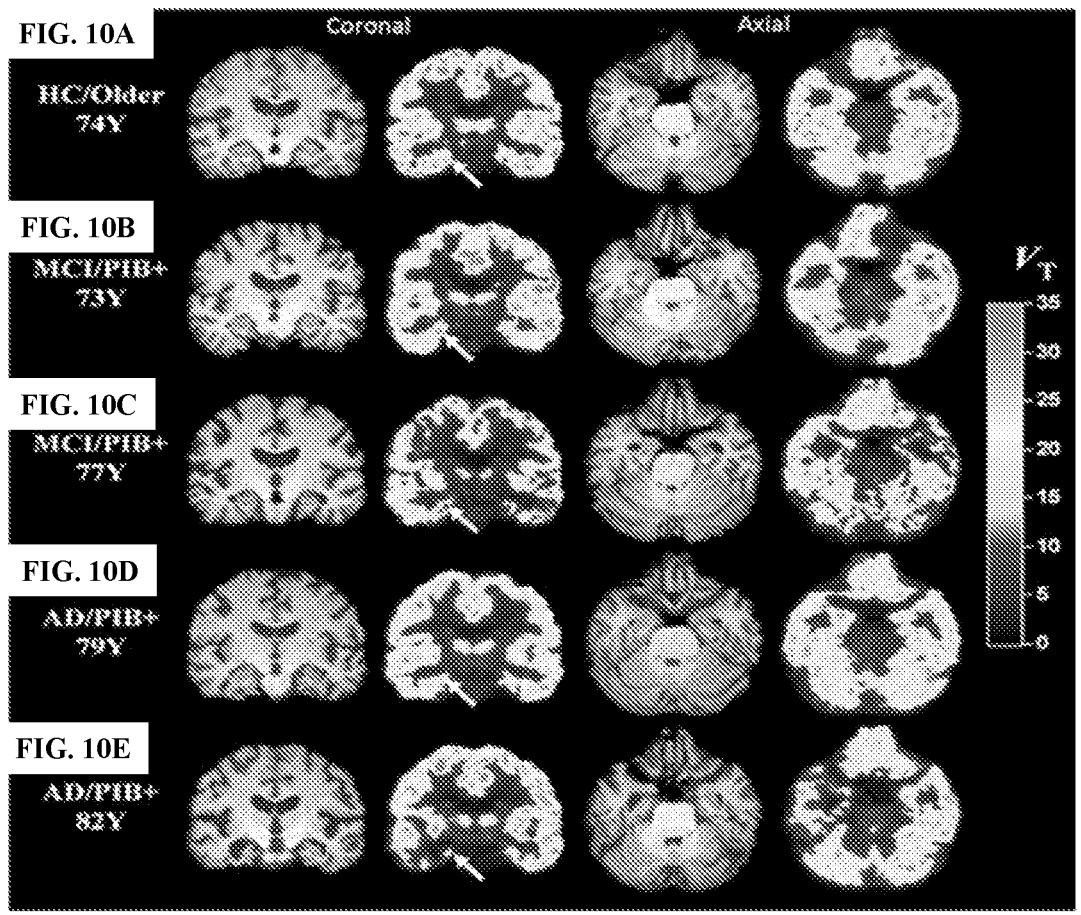
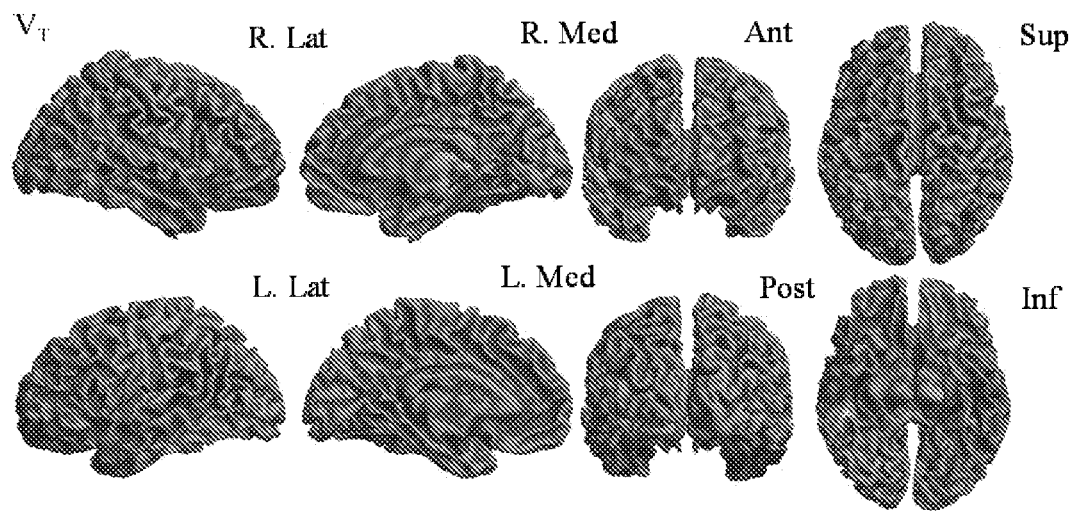
FIG. 10F

RADIOLABELED PHARMACEUTICALS AND METHODS OF MAKING AND USING SAME

CROSS-REFERENCE TO RELATED APPLICATIONS

The present application is a 35 U.S.C. § 371 national phase application from, and claims priority to, International Application No. PCT/US2018/018388, filed Feb. 15, 2018, and published under PCT Article 21(2) in English, which claims priority under 35 U.S.C. § 119(e) to U.S. Provisional Patent Application No. 62/460,541, filed Feb. 17, 2017, each of which is incorporated herein by reference in its entirety.

BACKGROUND OF THE INVENTION

Alzheimer's disease (AD) affects more than 35 million people worldwide, and the number is estimated to quadruple in 40 years if there remains no cure. AD is characterized by the accumulation of plaques and fibrillary tangles, i.e., β-amyloid plaques (aβ) and tau protein aggregates, with significant loss of neurons and atrophy at late stage, and can only be definitively diagnosed with postmortem histology staining of brain tissues. Early symptoms of AD are marked by the impairment of declarative memories, and accumulating evidence suggests that this occurs as the hippocampal synapses are compromised by soluble 0-amyloid protein oligomers during the earliest phase of AD. Evidence also suggests that neuropathophysiological development occurs for many years, if not decades, before any clinical presentation, with mild cognitive impairment (MCI) being a prodrome of AD, and synapse loss occurring prior to the accumulation of aβ.

The fact that there are no disease-modifying drugs for AD after decades of efforts to discover them drives us to consider early intervention as a strategy to treat that debilitating disease. With new treatments being tested, a biomarker for reliable, early diagnosis and prognosis of AD will enable more effective intervention before severe neurodegeneration sets in. The usefulness of positron emission tomography (PET) imaging for AD diagnosis has been well recognized by the AD community, as evidenced by its inclusion in the new diagnostic criteria for AD. PET imaging of aβ using Pittsburgh compound B (PIB) has emerged as a diagnostic tool included in clinical trials for aβ-targeting drugs. However, aβ accumulation is necessary but not sufficient to produce clinical manifestations of AD, with some people carrying aβ but never expressing dementia during their life. In an AD model, the recovery of cognitive function correlates well with the recovery of synapse density, rather than any changes in aβ. Thus, early detection and prediction of AD progression remains a big challenge, with no validated modality.

As one of the earliest and most consistent hallmarks of AD, regional synaptic losses correlate with the severity of AD from a postmortem study of AD patients. Regional synaptic loss in the hippocampus and prefrontal cortex is directly related to memory and cognitive dysfunction, and is one of the earliest signs of preclinical or prodromal AD, even before the onset of aβ plaques. Synaptic function has been indirectly measured by detecting neuronal activity via positron emission tomography (PET) imaging with $^{18}$F-fluorodeoxyglucose (FDG), or FDG PET. However, as FDG PET measures glucose metabolism of neurons, it is prone to confounders such as blood glucose level, neuron activation, and so forth. There is a need for an imaging biomarker that is directly linked to synaptic density and free of confounding factors in its measurement.

As the second most common neurodegenerative disease after AD, Parkinson's disease (PD) affects more than 10 million people worldwide, and causes enormous socioeconomic burden. There is evidence showing synaptic density changes in animal models and post-mortem PD patients. The exact synaptic density dynamics during the developing process of PD is yet to be clarified, partly due to the lack of a non-invasive imaging tool. From limited literature reports, an increase in synaptic density in the striatum was observed in animal models at the early stages of PD (proposed to be due to a compensatory mechanism from dopaminergic denervation), while a decrease in synaptic density was observed at the later stages of PD with clinical manifestations. The synaptic decrease was also found outside of the nigrostriatal system and include non-dopamine neurons in the cortex.

Stroke is a devastating disease that has high mortality and morbidity rates. As the most commonly used clinical outcome measure for stroke clinical trials, the modified ranking scale (mRS), which measures the degree of disability or dependence in the daily activities of the stroke patients, is subjective. One of the pathological features of stroke is synaptic deficit, with recovery of motor and memory functions after stroke accompanied by the increase of synaptic density. Studies in cortical stroke models have found a correlation between motor recovery and the synaptophysin expression level, a biomarker of synaptic density.

As a common neurological disorder, multiple sclerosis (MS) is a leading cause of disability from cognitive dysfunction. Cognitive deficits have been reported in 40-65% of MS patients at all stages and subtypes. These cognitive deficits relate to demyelination associated with loss of synaptic density and brain atrophy. Postmortem brain pathology showed hippocampal demyelination in MS as well as significant synaptic density loss (~50%). Significant reduction of cortical axonal density was observed only in demyelinated areas of cortical gray matter, but synapse loss was present also in normal appearing gray matter.

Autism spectrum disorder (ASD) is a range of disorders that are characterized by social and communication deficits and repetitive behaviors. Recent research suggests that children and teens with autism have an abnormal "pruning" of synapses in the brain during development, which results in a surplus of brain synapses. Thus abnormal synaptic homeostasis represent a risk factor for ASD and therapies to correct these synaptic defects might be effective in the treatment of ASD.

Epilepsy is a chronic brain disorder that affects nearly 3 million people in the United State. The hallmarks of epilepsy are spontaneous recurrent seizures and frequent comorbid conditions such as anxiety, depression, cognitive impairment, and sudden unexpected death. Despite the availability of multiple classes of antiepileptic drugs, about 30% of the patients develop medically intractable epilepsy, with a particularly high (50-70%) rate of intractable cases among patients with temporal lobe epilepsy. Thus, surgery for epilepsy has been a long-standing practice for medically refractory patients, but are dependent on the preoperative localization of the seizure-onset zone. SV2A is the target for levetiracetam, a second generation antiepileptic drug, and its expression has been shown to be reduced by 30-50% in the anterior temporal neocortex of patients with temporal lobe epilepsy. A similar reduction in SV2A expression has also been seen in the hippocampus of temporal lobe epilepsy patients with hippocampal sclerosis and in tissues resected from epilepsy patients with focal cortical dysplasia and tuberous sclerosis.

Traumatic brain injury (TBI) is a devastating problem worldwide. Approximately 2 million head injuries occur each year in the US, which lead to over 50,000 deaths and approximately 80,000 individuals who survive with severe neurological dysfunction. A large portion of patients with severe injury develop cognitive dysfunction, as well as post-traumatic seizures with epilepsy that can last for years. Acute TBI has been shown to be associated with reorganization of synapses, and functional recovery from TBI has been indicated to accompany recovery in synaptic function.

Diabetes mellitus is a group of chronic metabolic conditions, all of which are characterized by elevated blood glucose levels resulting from the body's inability to produce insulin or resistance to insulin action, or both. Diabetes prevalence is increasing rapidly. According to the 2016 data from the World Health Organization (WHO), an estimated 422 million adults globally are living with diabetes mellitus, and it is becoming one of the major health problems in developing countries. Diabetes-related complications, e.g., cardiovascular disease, kidney disease, neuropathy, blindness, and lower-extremity amputation are a significant cause of increased morbidity and mortality among people with diabetes, and result in a heavy economic burden. In the United States, the prevalence and incidence of diabetes have increased dramatically during the past 2 decades approaching epidemic proportions. Effective interventions are desperately needed to slow the diabetes epidemic and reduce diabetes-related complications. Type 1 Diabetes mellitus accounts for 5% to 10% of all cases of diabetes, and is characterized by a complete lack of insulin production caused by autoimmune beta-cell mass (BCM) destruction in the islets of Langerhans of the pancreas and subsequent deficient insulin secretion in response to hyperglycemia. A clinically viable means to measure BCM would be an invaluable tool for evaluating the physiological basis of therapeutic approaches to restore deficient insulin secretory capacity. SV2A is expressed in the pancreas associated with insulin-containing granules in neuroendocrine cells.

There is thus a need in the art for novel compounds and/or compositions that can be used in the clinic for the diagnosis of a neurodegenerative, neurological, psychiatric, and/or metabolic disease, such as but not limited to AD, PD, MS, autism, epilepsy, stroke, TBI, schizophrenia, post-traumatic stress disorder (PTSD), depression, and diabetes, or any other diseases/disorders where involvement of synaptic disruptions and/or abnormalities exists. The present disclosure addresses this need.

BRIEF SUMMARY OF THE INVENTION

In one aspect, the invention provides a compound of formula 1:

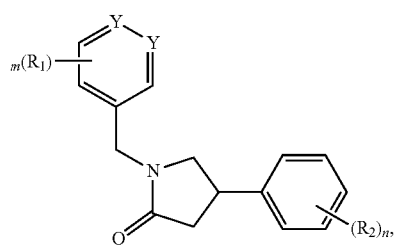

1 wherein: each instance of Y is independently selected from the group consisting of N, CH and $CR_1$, provided that 0-1 Y is N; each instance of $R_1$ and $R_2$ is independently selected from the group consisting of F, Cl, Br, I, $C_1$-$C_6$ alkyl, $C_1$-$C_6$ haloalkyl, CN, —$N_3$ and —$NO_2$, provided that at least one instance of $R_1$ or $R_2$ is F; and m and n are independently selected from the group consisting of 0, 1, 2, 3, 4 and 5; or a salt, solvate, tautomer or enantiomer thereof, or any mixtures thereof.

In various embodiments, the compound is a compound of formula 2:

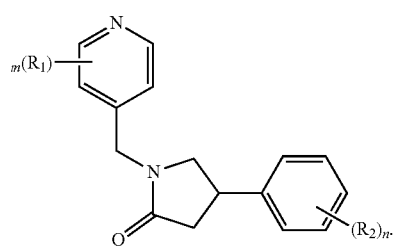

2 or a salt, solvate, tautomer or enantiomer thereof; or any mixtures thereof.

In various embodiments, the compound is selected from the group consisting of:

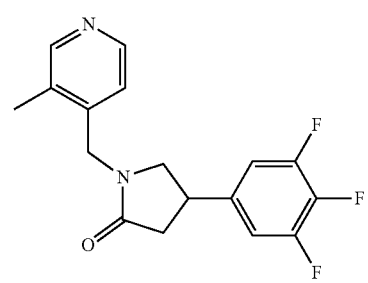

3

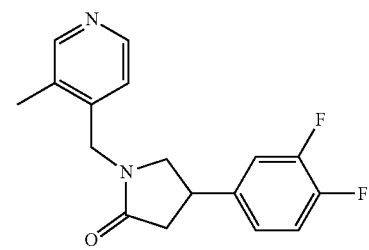

4

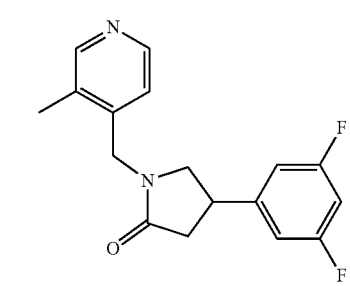

5

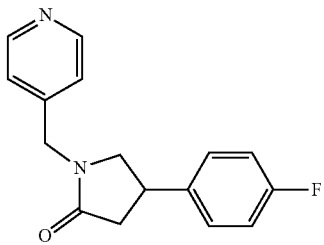
5
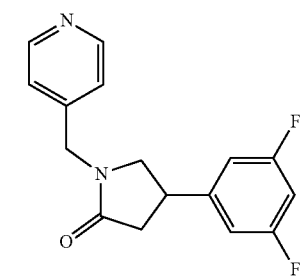
7
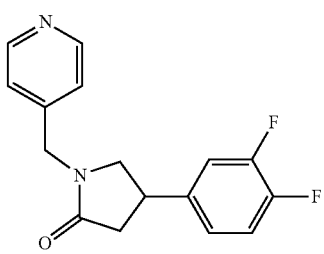
8
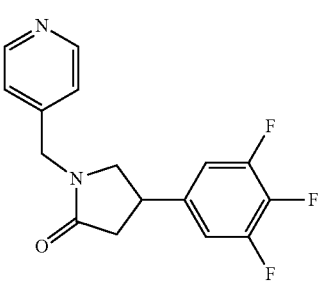
9
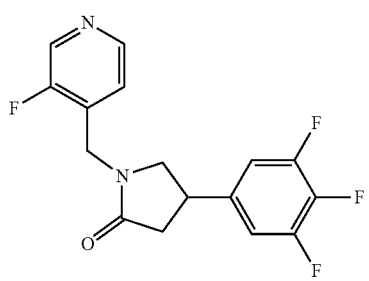
10
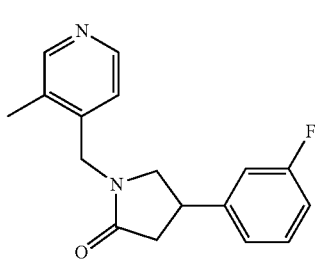
11
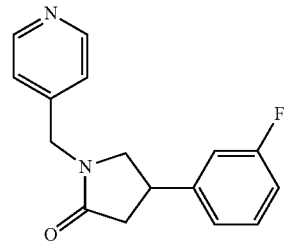
12
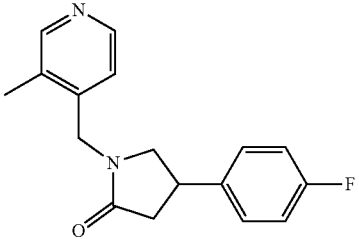
13
wherein at least one instance of F is $^{18}$F; or a salt, solvate, tautomer or enantiomer thereof; or any mixtures thereof.
In various embodiments, the compound is a compound of formula 14, or a salt, solvate, tautomer or enantiomer thereof; or any mixtures thereof:
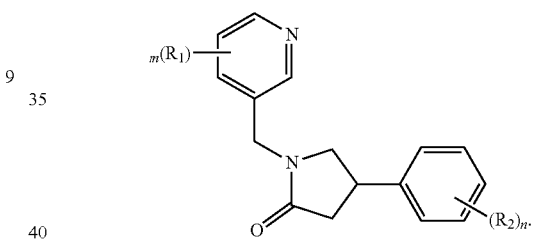
14
In various embodiments, the compound is selected from the group consisting of:
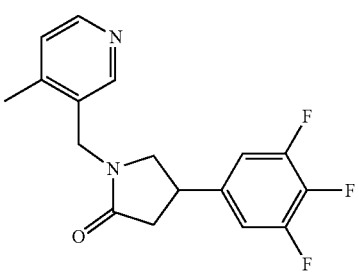
15
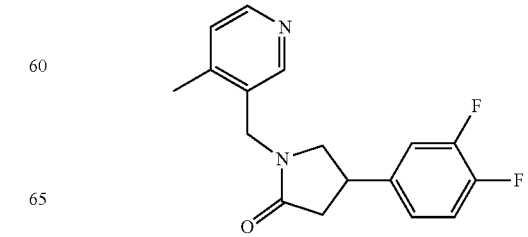
16

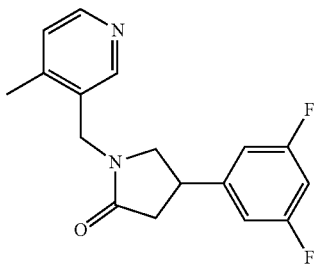

17

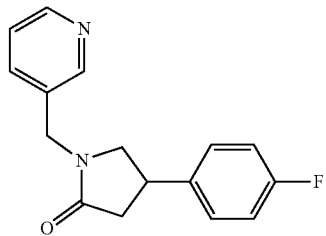

18

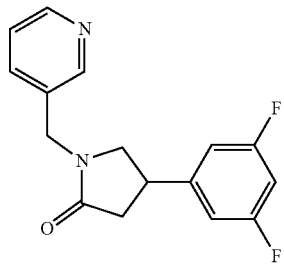

19

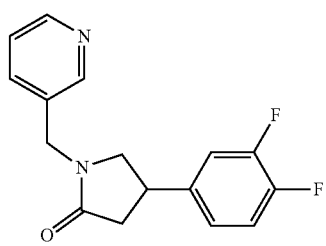

20

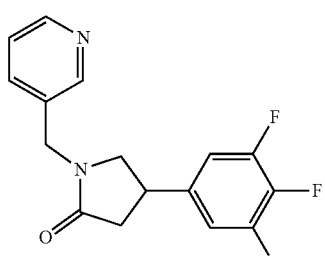

21

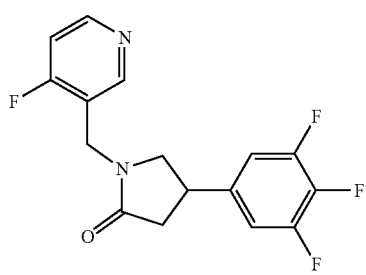

22

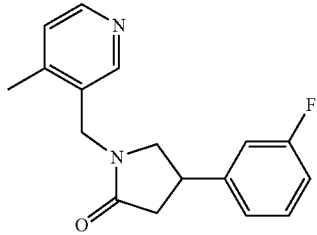

23

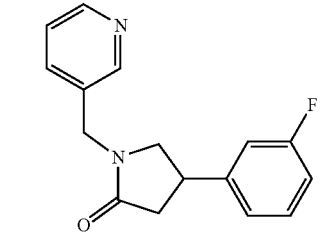

24

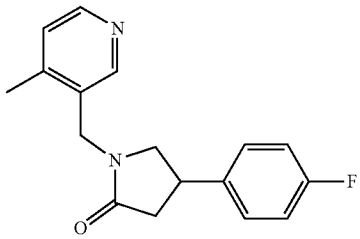

25 wherein at least one instance of F is $^{18}$F; or a salt, solvate, tautomer or enantiomer thereof; or any mixtures thereof.

In another aspect, the invention provides a compound of formula 26:

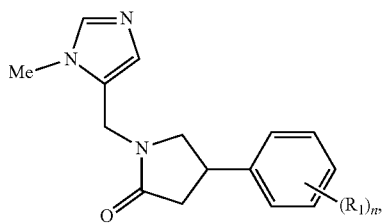

26 wherein: each instance of $R_1$ is independently selected from the group consisting of F, Cl, Br, I, $C_1$-$C_6$ alkyl, $C_1$-$C_6$ haloalkyl, CN, —$N_3$ and —$NO_2$, provided that at least one instance of $R_1$ is F; and n is selected from the group consisting of 1, 2, 3, 4 and 5, or a salt, solvate, tautomer or enantiomer thereof, or any mixtures thereof.

In various embodiments, the compound is 27, wherein at least one instance of F is $^{18}$F, or a salt, solvate, tautomer or enantiomer thereof, or any mixtures thereof:

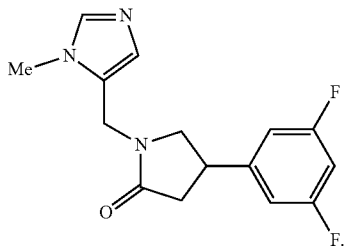

In various embodiments, the compound is in an enantiomerically enriched form. In various embodiments, the compound is a single enantiomer that is essentially free of the corresponding other enantiomer.

In various embodiments, the invention provides a pharmaceutical composition comprising the compound described above and at least one pharmaceutical excipient. In various embodiments, the composition is formulated for intravenous delivery.

In another aspect, the invention provides a method of decreasing the amount of unbound synaptic vesicle glycoprotein 2A (SV2A) in at least one region of the brain of a subject. In certain embodiments, the method comprises administering to the subject at least one compound or at least one pharmaceutical composition of the invention.

In another aspect, the invention provides a method of detecting and/or measuring the amount of synaptic vesicle glycoprotein 2A (SV2A) in a subject's body. In certain embodiments, the method comprises administering to the subject at least one compound or at least one pharmaceutical composition of the invention. In other embodiments, the method comprises detecting the at least one compound bound to the at least one region of the body of the subject, thereby detecting the amount of SV2A in the at least one region of the body of the subject.

In another aspect, the invention provides a method of imaging at least one region of a subject's body. In certain embodiments, the method comprises administering to the subject at least at least one compound or at least one pharmaceutical composition of the invention. In other embodiments, the method comprises detecting the at least one compound by positron emission tomography (PET) in at least one region of the body of the subject; thereby generating an image of the at least one region of the body of the subject.

In another aspect, the invention provides a method of detecting and/or measuring synaptic density in at least one region of a subject's body. In certain embodiments, the method comprises administering to the subject at least one at least one compound or at least one pharmaceutical composition of the invention. In other embodiments, the method comprises detecting the at least one compound by PET in at least one region of the body of the subject. In yet other embodiments, the method comprises determining a level of SV2A in the at least one region of the body of the subject.

In another aspect, the invention provides a method of detecting a disease or disorder involving synaptic disruptions and/or synaptic abnormalities or a metabolic disease or disorder in a subject's body. In certain embodiments, the method comprises administering to the subject at least one compound or at least one pharmaceutical composition of the invention. In other embodiments, the method comprises detecting the at least one compound by PET in at least one region of the body of the subject. In yet other embodiments, the method comprises determining a level of SV2A in the at least one region of the body of the subject, and comparing it to a control reference from a control subject who is not affected by the disease or disorder. In yet other embodiments, if the SV2A level in the at least one region of the subject's body is lower than in the control reference, the disease or disorder is detected in the subject.

In another aspect, the invention provides a method of monitoring and/or evaluating effectiveness of treatment and/or therapy for a disease or disorder involving synaptic disruptions and/or synaptic abnormalities a metabolic disease or disorder in a subject's body. In certain embodiments, the method comprises administering to the subject at least one compound or at least one pharmaceutical composition of the invention. In other embodiments, the method comprises detecting the at least one compound by PET in at least one region of the body of the subject. In yet other embodiments, the method comprises determining a level of SV2A in the at least one region of the body of the subject, and comparing it to a control reference from the subject before receiving the therapy and/or treatment. In yet other embodiments, if the SV2A level in the at least one region of the body of the subject is higher than in the control reference, the treatment and/or therapy is at least partially effective for the subject.

In various embodiments the disease or disorder is at least one selected from the group consisting of Alzheimer's disease (AD), Parkinson's disease (PD), multiple sclerosis (MS), autism, epilepsy, stroke, traumatic brain injury (TBI), schizophrenia, psychiatric disease, and diabetes.

In various embodiments, the disease or disorder is AD. In various embodiments, the AD is pre-clinical or prodromal AD. In various embodiments, the disease or disorder is PD. In various embodiments, the disease or disorder is MS. In various embodiments, the disease or disorder is autism. In various embodiments, the disease or disorder is epilepsy. In various embodiments, the disease or disorder is stroke. In various embodiments, the disease or disorder is TBI. In various embodiments, the disease or disorder is a psychiatric disease, such as but not limited to depression, schizophrenia, post-traumatic stress disorder (PTSD), and/or substance abuse disorder. In various embodiments, the disease or disorder is diabetes.

In another aspect, the invention provides a method of detecting and/or measuring a seizure onset zone in a subject with epilepsy, stroke, traumatic brain injury, Parkinson's disease or autism. In certain embodiments, the method comprises administering to the subject at least one compound or at least one pharmaceutical composition of the invention. In other embodiments, the method comprises detecting the at least one compound by PET in at least one region of the brain of the subject. In yet other embodiments, the method comprises determining a level of SV2A in the at least one region of the brain of the subject. In yet other embodiments, if an area within the at least one region has lower SV2A level than the rest of the at least one region, the area is identified as a seizure onset zone.

In another aspect, the invention provides a method of detecting an ischemic area in a subject with stroke. In certain embodiments, the method comprises administering to the subject at least one compound or at least one pharmaceutical composition of the invention. In other embodiments, the method comprises detecting the at least one compound by PET in at least one region of the brain of the subject. In yet other embodiments, the method comprises determining a level of SV2A in the at least one region of the brain of the subject. In yet other embodiments, if an area within the at least one region has lower SV2A level than the rest of the at least one region, the area is identified as being ischemic.

In various embodiments, the region of the subject's body is a region of the brain and the region of the brain comprises at least one selected from the group consisting of cingulate cortex, frontal cortex, insular cortex, nucleus accumbens, occipital cortex, temporal cortex, putamen, caudate nucleus, thalamus, cerebellum, hippocampus, globus pallidus, amygdala, brainstem, pons, and centrum semiovale. In various embodiments, the region of the subject's body comprises a region of the pancreas.

BRIEF DESCRIPTION OF THE DRAWINGS

The following detailed description of illustrative embodiments of the invention will be better understood when read in conjunction with the appended drawings. For the purpose of illustrating the invention, certain illustrative embodiments are shown in the drawings. It should be understood, however, that the invention is not limited to the precise arrangements and instrumentalities of the embodiments shown in the drawings.

FIG. 2A is a graph illustrating a time-activity course of regional radioactivity in the rhesus monkey brain after i.v. injection of (R)-$^{11}$C-3. Data are mean±standard deviation of 5 measurements. X-axis is scan time; Y-axis is standardized uptake value (SUV). FIG. 2B is a graph illustrating a time-activity course of regional radioactivity in the rhesus monkey brain after i.v. injection of (R)-$^{18}$F-3. Data are mean±standard deviation of 3 measurements. FIG. 2C is a graph illustrating a time-activity course of regional radioactivity in the rhesus monkey brain after i.v. injection of (R)-$^{18}$F-4. Data are single measurements. FIG. 2D is a graph illustrating a time-activity course of regional radioactivity in the rhesus monkey brain after i.v. injection of (R)-$^{18}$F-5. Data are mean±standard deviation of 2 measurements. FIG. 2E is a graph illustrating a time-activity course of regional radioactivity in the rhesus monkey brain after i.v. injection of (R)-$^{18}$F-11. Data are mean±standard deviation of 3 measurements.

FIG. 10A are representative coronal and axial images of MRI and (R)-[11]C-3 parametric PET ($V_T$) in a cognitive normal healthy control (HC) with a negative [11]C-PB PET scan. Arrow indicates the hippocampus region. FIG. 10B are representative coronal and axial images of MRI and (R)-[11]C-3 parametric PET ($V_T$) in a mild cognitive impairment (MCI) patient with a positive $^{11}$C-PIB PET scan. Arrow indicates the hippocampus region. FIG. 10C are representative coronal and axial images of MRI and (R)-[11]C-3 parametric PET ($V_T$) in a mild cognitive impairment (MCI) patient with a positive [11]C-PB PET scan. Arrow indicates the hippocampus region. FIG. 10D are representative coronal and axial images of MRI and (R)-[11]C-3 parametric PET ($V_T$) in a mild AD dementia patient with a positive [11]C-PB PET scan. Arrow indicates the hippocampus region. FIG. 10E are representative coronal and axial images of MRI and (R)-[11]C-3 parametric PET ($V_T$) in a mild AD dementia patient with a positive [11]C-PB PET scans. Arrow indicates the hippocampus region. FIG. 10F is the whole brain SPM analysis with (R)-[11]C-3 $V_T$ values from MCI/AD patients (n=9) compared to those from cognitive normal healthy control subjects (n=8). The clearest reductions are in the hippocampus region. Shading indicates the regions with statistically significant reduction of (R)-[11]C-3 $V_T$ in MCI/AD patients compared to cognitive normal healthy control subjects, rendered on brain surfaces at different projections.

DETAILED DESCRIPTION OF THE INVENTION

Figure 1A:
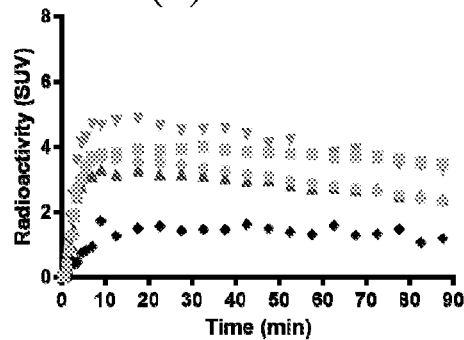
FIG. 1A is a graph illustrating a time-activity course of regional radioactivity in the rhesus monkey brain after i.v. injection of $(\pm)$-$^{18}$F-3. Data are single measurements. X-axis is scan time; Y-axis is standardized uptake value (SUV).
Figure 1B:
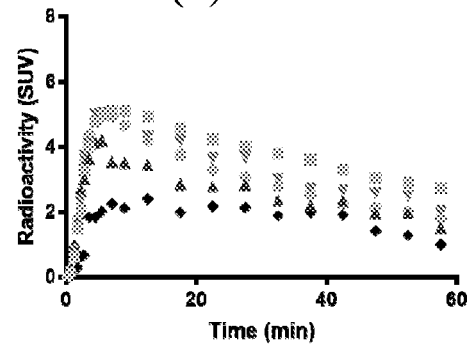
FIG. 1B is a graph illustrating a time-activity course of regional radioactivity in the rhesus monkey brain after i.v. injection of $(\pm)$-$^{18}$F-4. Data are single measurements.
Figure 1C:
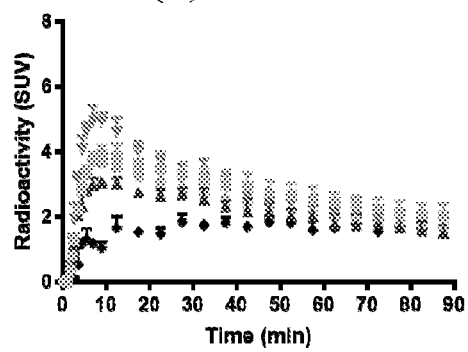
FIG. 1C is a graph illustrating a time-activity course of regional radioactivity in the rhesus monkey brain after i.v. injection of $(\pm)^{18}$F-10. Data are mean±standard deviation of 2 measurements.
Figure 1D:
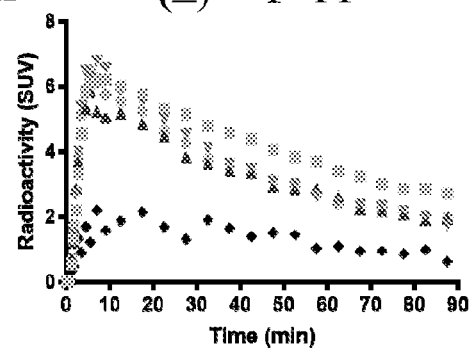
FIG. 1D is a graph illustrating a time-activity course of regional radioactivity in the rhesus monkey brain after i.v. injection of $(\pm)$-$^{18}$F-11. Data are single measurements.
Figure 1E:
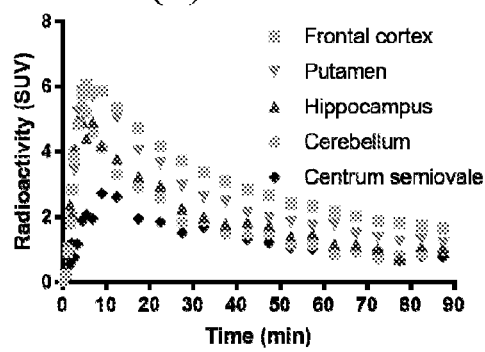
FIG. 1E is a graph illustrating a time-activity course of regional radioactivity in the rhesus monkey brain after i.v. injection of $(\pm)$-$^{18}$F-12. Data are single measurements.
Figure 3A:
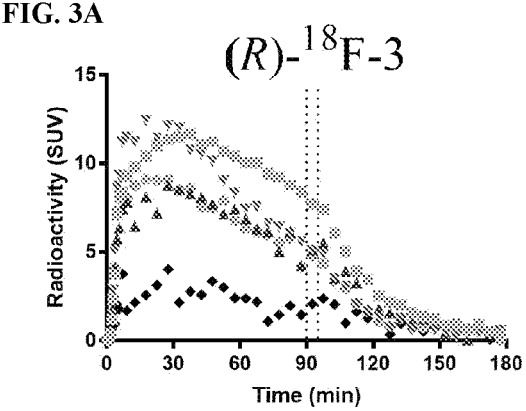
FIG. 3A is a graph illustrating the displacement effect of levetiracetam (30 mg/kg) on regional radioactivity in the rhesus monkey brain after i.v. injection of (R)-$^{18}$F-3. Data are single measurements. The vertical dotted lines represent levetiracetam administration which was i.v. infused at 60-65 min post radiotracer injection.
Figure 3B:
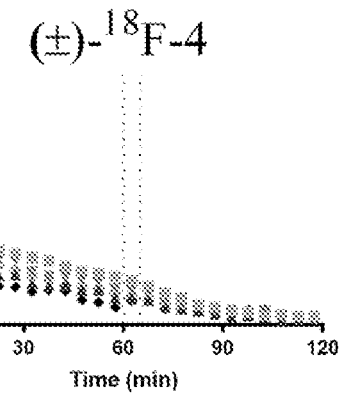
FIG. 3B is a graph illustrating the displacement effect of levetiracetam (30 mg/kg) on regional radioactivity in the rhesus monkey brain after i.v. injection of $(\pm)$-$^{18}$F-4. Data are single measurements. The vertical dotted lines represent levetiracetam administration which was i.v. infused at 60-65 min post radiotracer injection.
Figure 3C:
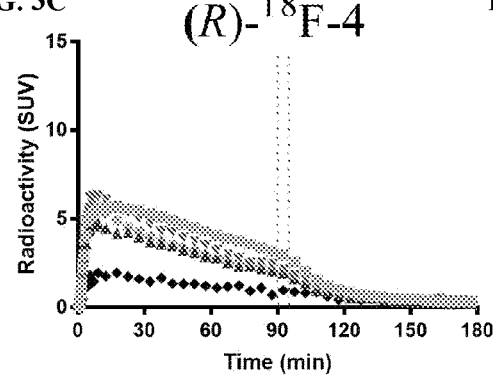
FIG. 3C is a graph illustrating the displacement effect of levetiracetam (30 mg/kg) on regional radioactivity in the rhesus monkey brain after i.v. injection of (R)-$^{18}$F-4. Data are single measurements. The vertical dotted lines represent levetiracetam administration which was i.v. infused at 90-95 min post radiotracer injection.
Figure 3D:
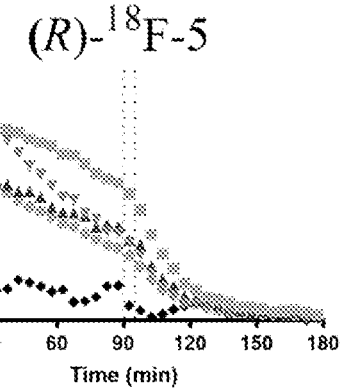
FIG. 3D is a graph illustrating the displacement effect of levetiracetam (30 mg/kg) on regional radioactivity in the rhesus monkey brain after i.v. injection of (R)-$^{18}$F-5. Data are single measurements. The vertical dotted lines represent levetiracetam administration which was i.v. infused at 90-95 min post radiotracer injection.
Figure 3E:
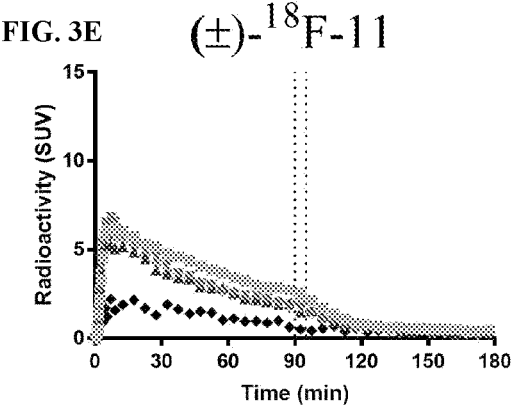
FIG. 3E is a graph illustrating the displacement effect of levetiracetam (30 mg/kg) on regional radioactivity in the rhesus monkey brain after i.v. injection of $(\pm)$-$^{18}$F-11. Data are single measurements. The vertical dotted lines represent levetiracetam administration which was i.v. infused at 90-95 min post radiotracer injection.
Figure 3F:
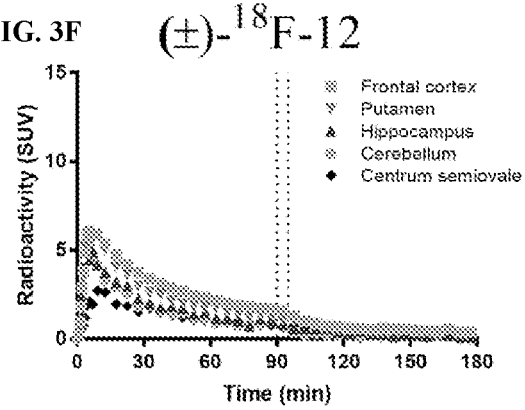
FIG. 3F is a graph illustrating the displacement effect of levetiracetam (30 mg/kg) on regional radioactivity in the rhesus monkey brain after i.v. injection of $(\pm)$-$^{18}$F-12. Data are single measurements. The vertical dotted lines represent levetiracetam administration which was i.v. infused at 90-95 min post radiotracer injection.
Figure 4A:
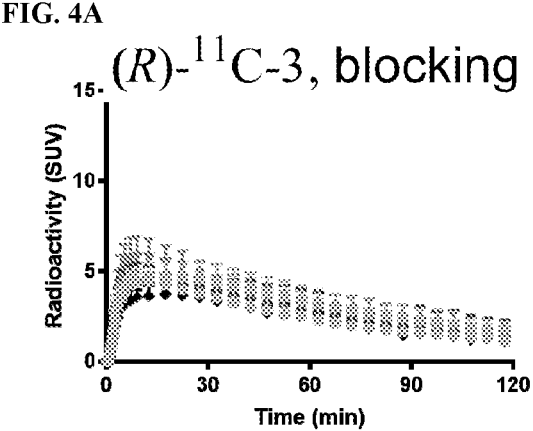
FIG. 4A is a graph illustrating the blocking effect of levetiracetam (30 mg/kg) on regional radioactivity in the rhesus monkey brain after i.v. injection of (R)-$^{11}$C-3. Data are single measurements. Levetiracetam was administered i.v. at 10 min before radiotracer injection.
Figure 4B:
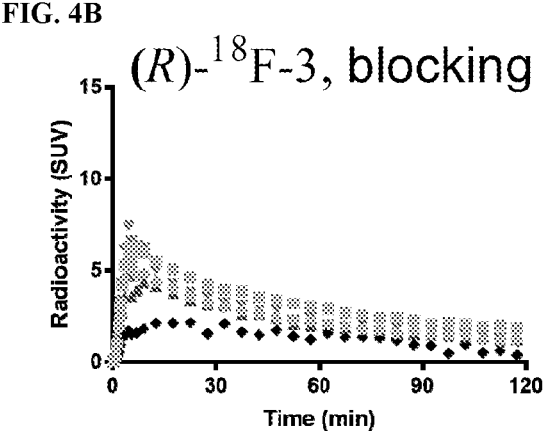
FIG. 4B is a graph illustrating the blocking effect of (R)-3 (150 µg/kg) on regional radioactivity in the rhesus monkey brain after i.v. injection of (R)-$^{18}$F-3. Data are single measurements. (R)-3 was administered i.v. at 10 min before radiotracer injection.
Figure 4C:
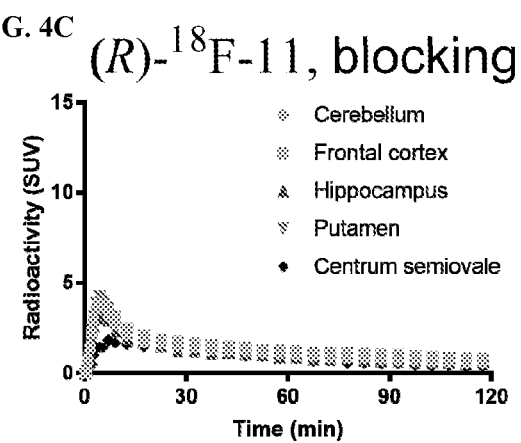
FIG. 4C is a graph illustrating the blocking effect of (R)-3 (150 jag g/kg) on regional radioactivity in the rhesus monkey brain after i.v. injection of (R)-$^{18}$F-11. Data are single measurements. (R)-3 was administered i.v. at 10 min before radiotracer injection.
Figure 5:
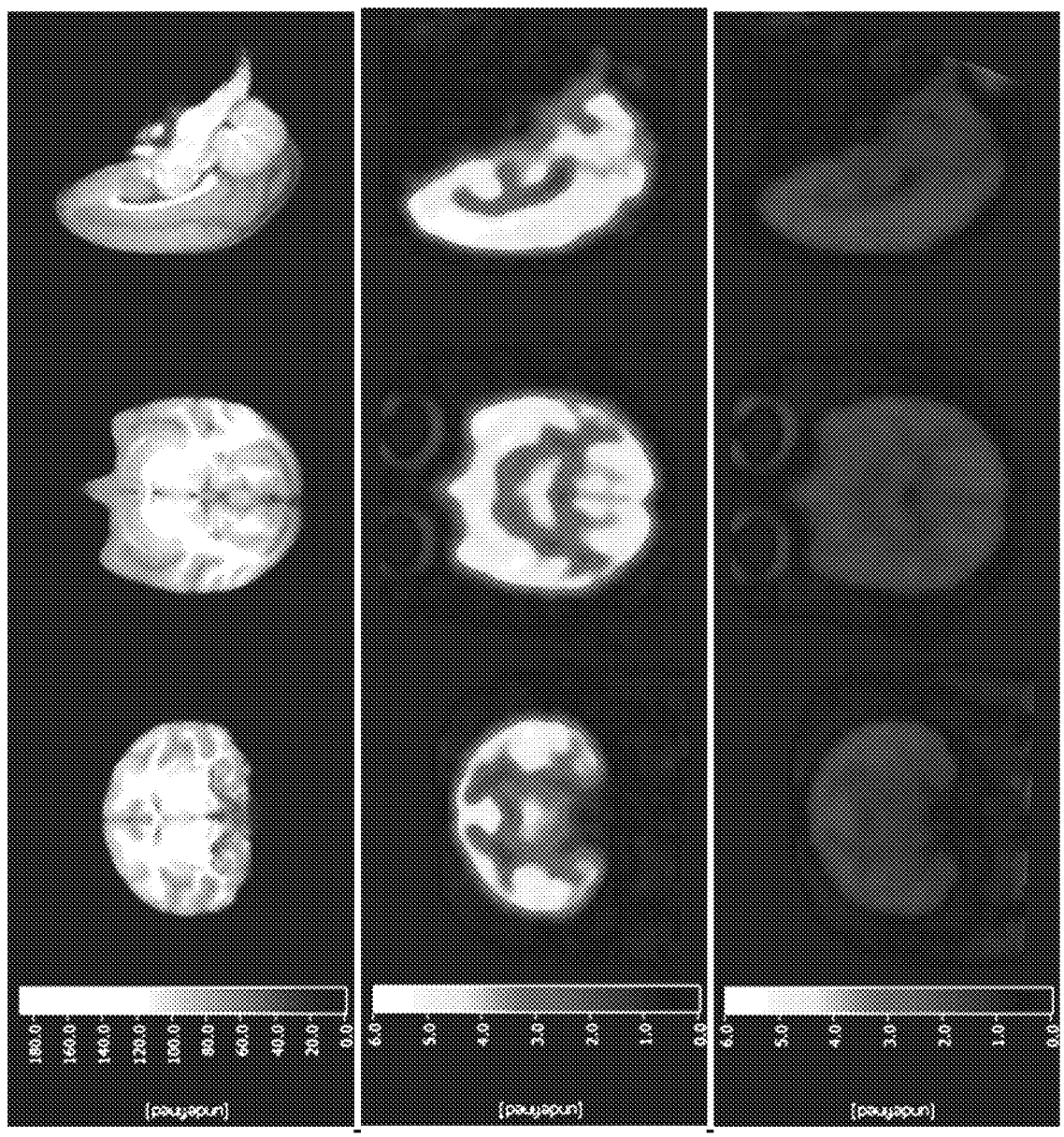
FIG. 5 shows template MRI (top) and PET summation images of the rhesus monkey brain from 20-40 min after i.v. injection of (R)-$^{18}$F-11 (middle), and blocking with (R)-3 (150 jag/kg, i.v.) (bottom). (R)-3 was administered i.v. at 10 min before radiotracer injection.
Figure 6:
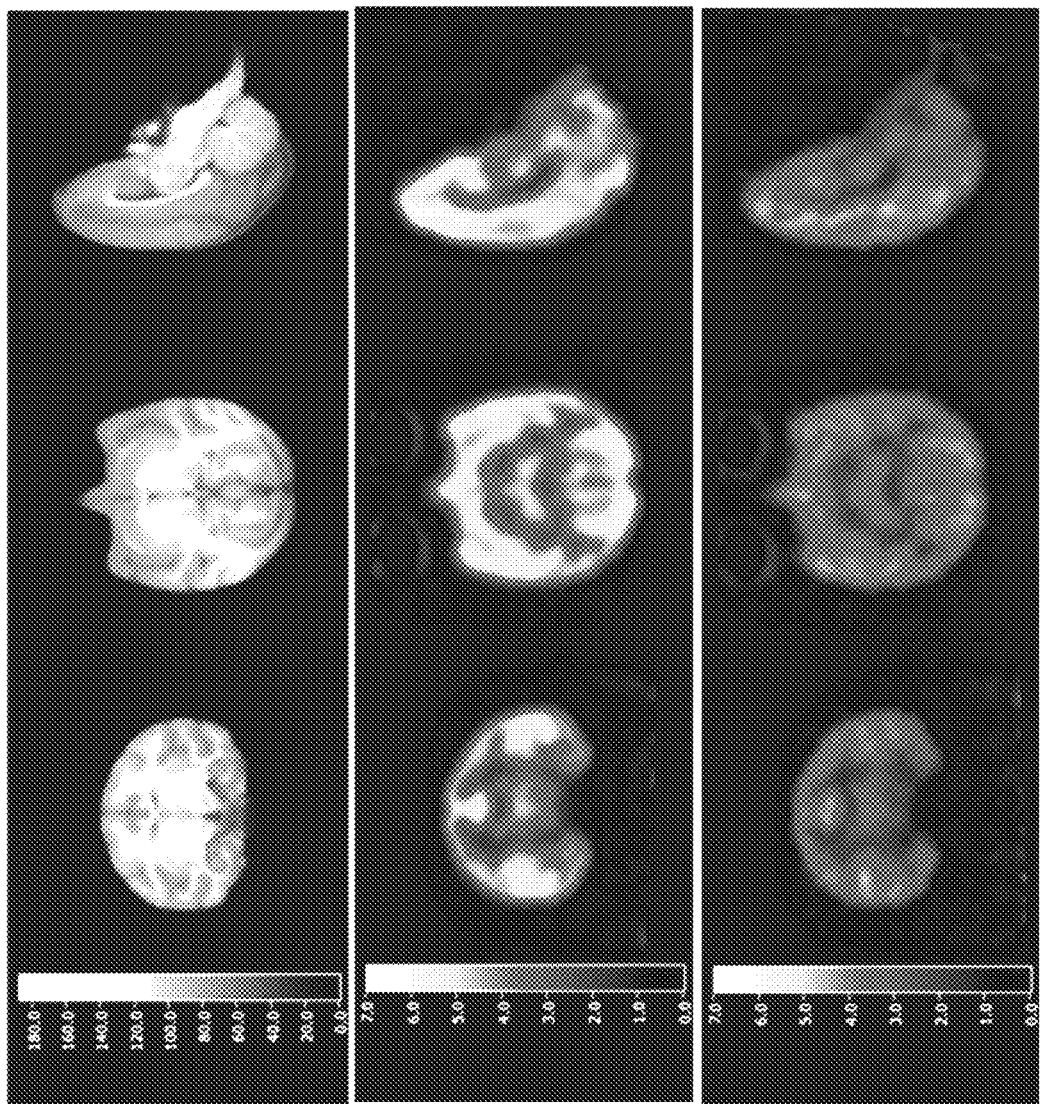
FIG. 6 shows template MRI (top) and PET summation images of the rhesus monkey brain from 20-40 min after i.v. injection of (R)-$^{18}$F-4 (middle), and (S)-$^{18}$F-4 (bottom).
Figure 7:
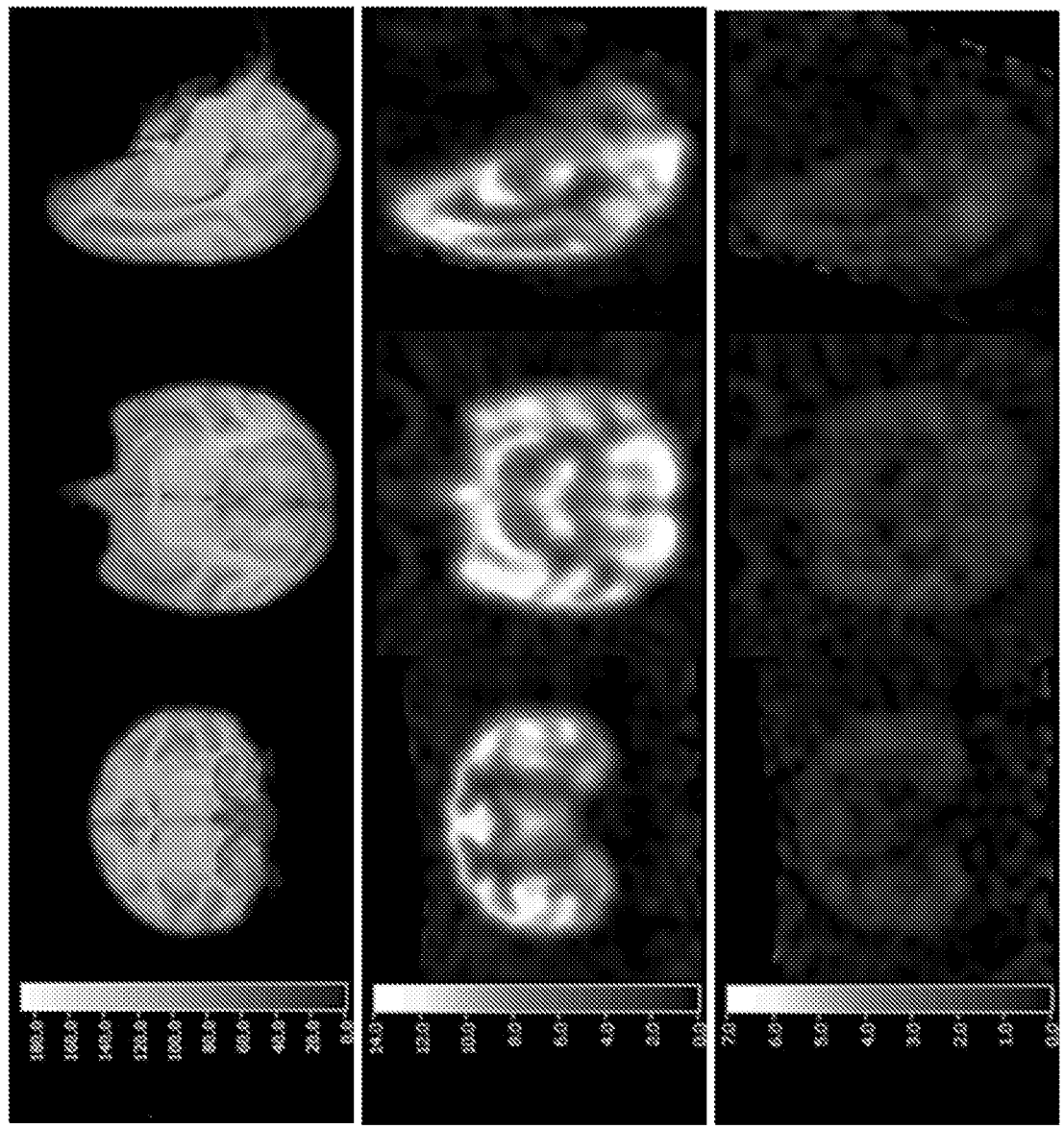
FIG. 7 shows template MRI (top) and PET summation images of the rhesus monkey brain from 20-40 min after i.v. injection of (R)-$^{18}$F-5 (middle), and from 140-160 min after i.v. injection of (R)-$^{18}$F-5 (and from 50-70 min after i.v. injection of 30 mg/kg levetiracetam, bottom). Levetiracetam was given at 90-95 min after radiotracer injection.

Synaptic vesicle (SV) proteins are abundant, hydrophobic, integral 12 transmembrane glycoproteins. They are expressed in three isoforms, SV2A, SV2B, and SV2C, with SV2A being the most abundant and ubiquitously distributed in all brain grey matter areas. In one aspect, the invention provides compounds that bind to SV2A and can be used as imaging biomarkers. In one aspect, the invention provides compounds and/or compositions that can bind to SV2A. In other embodiments, such compounds and/or compositions can be used for monitoring disease progression, recovery and treatment effects of disease-modifying therapies. In another aspect, the invention provides methods of using such compounds to image at least portions of the brain or other organs such as the pancreas, measure changes in SV2A binding as a surrogate for synaptic density, or to diagnose a neurodegenerative, neurological, psychiatric, and/or metabolic disease, such as but not limited to AD, Parkinson's disease (PD), multiple sclerosis (MS), autism, epilepsy, stroke, traumatic brain injury (TBI), schizophrenia, post-traumatic stress disorder (PTSD), depression, and diabetes, or any diseases/disorders where involvement of synaptic disruptions and/or abnormalities are present.

In one aspect, PET imaging of the synaptic vesicle glycoprotein-2A (SV2A) provides an imaging biomarker for synaptic density that is useful in the early diagnosis of AD, and monitoring of disease progression and treatment efficacy of disease-modifying therapies.

Synaptic dysfunction is involved in PD and regional synaptic density changes are characteristic in the pathogenesis of the disease. In another aspect, PET imaging of synaptic density in the brains of PD patients will not only reveal the disease progression, but also serve as a diagnosis or prognosis tool to facilitate more effective disease-modification interventions.

In another aspect, measurement of synaptic density after stroke by PET imaging of SV2A provides an objective measure of disease progression and treatment efficacy. In another aspect, as a synaptic density biomarker, SV2A PET imaging can be used to monitor the progression of MS cognitive dysfunction, and treatment effect of disease-modifying therapies. In another aspect, measurement of synaptic density by PET imaging of SV2A provides a non-invasive method to diagnose ASD and monitor the efficacy of therapies targeting the correction of synaptic abnormality in ASD. In another aspect, PET imaging of SV2A provides an effective, non-invasive way to detect the seizure-onset zone in patients with epilepsy and aid in the treatment of this disease. In another aspect, detection of synaptic density and/or function by SV2A PET imaging offers a non-invasive and objective means to monitor TBI, recovery, and treatment efficacy of therapies.

A number of psychiatric disorders, such as depression, schizophrenia, post-traumatic stress disorder (PTSD), and substance abuse disorders, are believed to be associated with region-specific decreases in synaptic density. In various aspects, PET imaging of SV2A as a synaptic density biomarker is a valuable tool for the accurate diagnosis and treatment effect monitoring of these psychiatric disorders.

In another aspect, non-invasive PET imaging of SV2A as a marker for endogenous pancreatic BCM may provide the needed tool for quantifying BCM in healthy subjects and type-1 diabetic patients, and for monitoring the treatment effects of therapeutic interventions.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. As used herein, each of the following terms has the meaning associated with it in this section.

Generally, the nomenclature used herein and the laboratory procedures in cell culture, molecular genetics, pharmacology, bioimaging and organic chemistry are those well-known and commonly employed in the art.

Standard techniques are used for biochemical and/or biological manipulations. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2002, Current Protocols in Molecular Biology, John Wiley & Sons, N.Y.), which are provided throughout this document.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "Alzheimer's Disease" or "AD" refers to the neurodegenerative disease associated with aβ plaque formation and/or tau protein aggregates, resulting in a progressive loss of memory function. As used herein, the term is applied to all phases of the disease, including mild cognitive impairment (MCI). This includes AD in pre-clinical or prodromal stages.

As used herein, the terms "analog," "analogue," or "derivative" are meant to refer to a chemical compound or molecule made from a parent compound or molecule by one or more chemical reactions. As such, an analog can be a structure having a structure similar to that of the small molecules described herein or can be based on a scaffold of a small molecule described herein, but differing from it in respect to certain components or structural makeup, which may have a similar or opposite action metabolically.

As used herein, the term "detecting" may refer to the qualitative observation of the presence of a biomarker or to the quantitative measurement of the relative or total amount of that biomarker or to a determination of its concentration. The term detecting may be applied to a sample, to a subject or to a defined region in the body of a subject.

As used herein, the term "binding" refers to the adherence of molecules to one another, such as, but not limited to, enzymes or any other proteins to substrates, antibodies to antigens, DNA strands to their complementary strands. Binding occurs because the shape and chemical nature of parts of the molecule surfaces are complementary. A common metaphor is the "lock-and-key" used to describe how enzymes fit around their substrate.

As used herein, the "subject's body" or "the body of the subject" particularly in the context of a region of the subject's body refers to the physical corpus of the subject. A region of the body of the subject may be any portion thereof. In various embodiments, the region of the subject's body may be the brain. In various embodiments, the region of the subject's body may be the pancreas.

A "disease" is a state of health of an animal, such as a human subject, wherein the animal cannot maintain homeostasis, and wherein if the disease is not ameliorated then the animal's health continues to deteriorate.

By "detectable label" is meant a composition that when linked to a molecule of interest renders the latter detectable, via spectroscopic, photochemical, radiological, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

An "effective amount" of a compound, as used herein in the context of a compound with a detectable label, is that amount of compound which is sufficient to allow effective measurement or imaging when provided to the patient by a particular method of administration. An appropriate effective amount in any individual case may be determined by one of ordinary skill in the art using routine experimentation.

As used herein, the phrase "a first compound is essentially free of a second compound" in a composition indicates that the ratio of the second compound to the first compound in the composition is about 10:90, 5:95, 4:96, 3:97, 2:98, 1:99, 0.5:99.5, 0.25:99.75, 0.1:99.9, 0.05:99.95, 0.025:99.975, 0.01:99.99 or 0:100.

The "level" of one or more biomarkers means the absolute or relative amount or concentration of the biomarker in the sample as determined by detecting the biomarker. The level of a biomarker may vary across a region of interest, for example, the level of the biomarker may be higher or lower in a subset of the region of interest and this may be interpreted to imply various biological states.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient.

Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids or bases, organic acids or bases, solvates, hydrates, or clathrates thereof.

By the term "specifically binds," as used herein, is meant a molecule, such as an antibody, which recognizes and binds to another molecule or feature, but does not substantially recognize or bind other molecules or features in a sample.

The term "substituted," as used herein and applied to chemical formulae means that a carbon or hydrogen atom in the group to which the term is applied may be changed to another atom, such as but not limited to nitrogen, oxygen, sulfur or halogens, so long as the substitution produces a stable compound.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 and so forth, as well as individual numbers within that range, for example, 1, 2, 2.7, 3, 4, 5, 5.3, and 6. This applies regardless of the breadth of the range.

Compounds

In one aspect, the invention provides compounds according to formula 1 or a salt, solvate, stereoisomer (such as, in a non-limiting example, an enantiomer or diastereomer (also known as diastereoisomer), and any mixtures thereof, such as, in a non-limiting example, mixtures in any proportion of enantiomers and/or diastereomers thereof), tautomer and any mixtures thereof, and/or geometric isomer and any mixtures thereof:

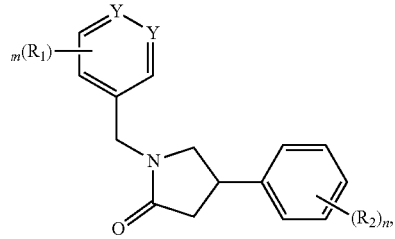

wherein:
each instance of Y is independently selected from the group consisting of N, CH and $CR_1$, provided that 0-1 Y is N; each instance of $R_1$ and $R_2$ is independently selected from the group consisting of F, Cl, Br, I, $C_1$-$C_6$ alkyl (such as but not limited to $CH_3$), $C_1$-$C_6$ haloalkyl (such as but not limited to $CF_3$), CN and —$NO_2$, provided that at least one instance of $R_1$ or $R_2$ is F; and m and n are independently selected from the group consisting of 0, 1, 2, 3, 4 and 5.

In certain embodiments, 1 encompasses multiple substitutions of $R_1$, e.g. 1, 2, 3 or 4 instances of $R_1$ on each ring. The synthetic processes by which these compounds can be made are illustrated in Example 1. As illustrated in FIGS. 3A-3F, 4A-4C, and 5 and in Examples 2-4, these compounds bind SV2A, which may be used as a biomarker for synaptic density. In certain embodiments, the compounds of formula 1 comprise a detectable label. In other embodiments, the detectable label is an isotope that can be detected by PET. In yet other embodiments, this isotope is $^{18}F$. Synthetic methods for selectively generating the isotopically labeled compounds are described in Example 1.

Compounds of the invention that possess at least one stereogenic center may be utilized as racemic mixtures or may be enriched in either the R or S enantiomer. In certain embodiments, the compounds are provided as isolated pure enantiomers. Illustrative methods of separating the enantiomers are discussed in Example 1 and Scheme 4.

In various embodiments, the compound of formula 1 is a compound of formula 2

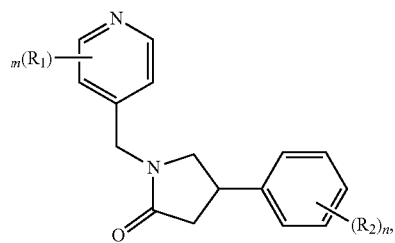

wherein:
each instance of $R_1$ and $R_2$ is independently selected from the group consisting of F, Cl, Br, I, $C_1$-$C_6$ alkyl (such as but not limited to $CH_3$), $C_1$-$C_6$ haloalkyl (such as but not limited to $CF_3$), CN and —$NO_2$, provided that at least one instance of $R_1$ or $R_2$ is F; and m and n are independently selected from the group consisting of 0, 1, 2, 3, 4 and 5; a salt, solvate, tautomer or enantiomer thereof, and any mixtures thereof.

In certain embodiments, the compound of formula 1 or 2 is at least one selected from the group consisting of:
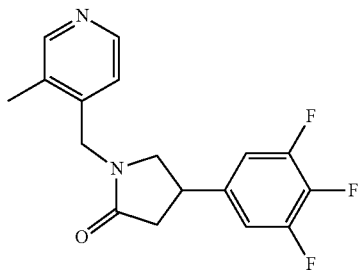
3
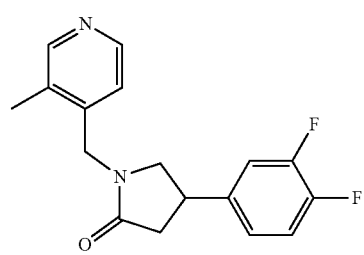
4
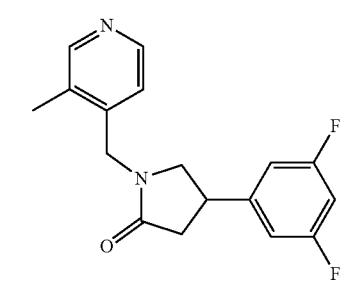
5
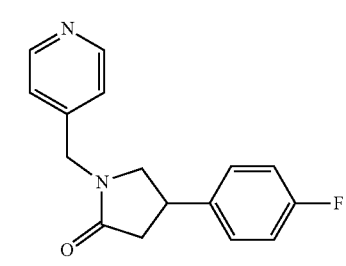
6
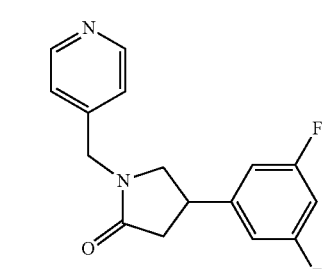
7
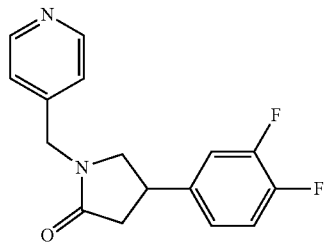
8
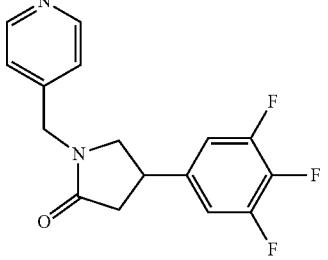
9
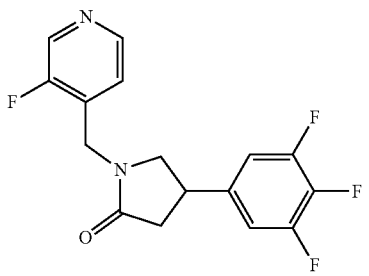
10
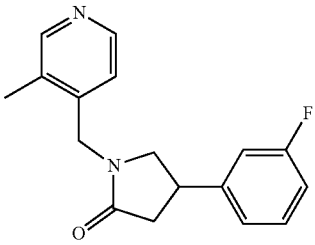
11
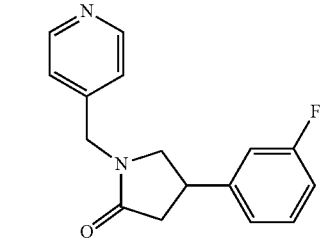
12
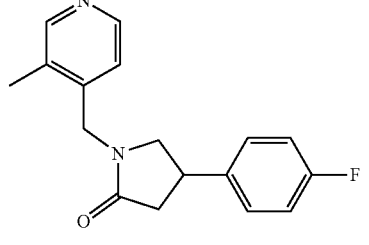
13
wherein at least one instance of F is $^{18}$F, a salt, solvate, tautomer or enantiomer thereof, and any mixtures thereof.

In certain embodiments the compound of formula 1 or 2 is selected from the group consisting of: 1-((3-methylpyridin-4-yl)methyl)-4-(3,4,5-trifluorophenyl) pyrrolidin-2-one; 4-(3,4-difluorophenyl)-1-((3-methylpyridin-4-yl)methyl) pyrrolidin-2-one; 4-(3,5-difluorophenyl)-1-((3-methylpyridin-4-yl)methyl)pyrrolidin-2-one; 4-(4-fluorophenyl)-1-(pyridin-4-ylmethyl)pyrrolidin-2-one; 4-(3,5-difluorophenyl)-1-(pyridin-4-ylmethyl) pyrrolidin-2-one; 4-(3,4-difluorophenyl)-1-(pyridin-4-ylmethyl)pyrrolidin-2-one; 1-(pyridin-4-ylmethyl)-4-(3,4,5-trifluorophenyl)pyrrolidin-2-one; 1-((3-fluoropyridin-4-yl)methyl)-4-(3,4,5-trifluorophenyl)pyrrolidin-2-one; 4-(3-fluorophenyl)-1-((3-methyl pyridin-4-yl)methyl)pyrrolidin-2-one; 4-(3-fluorophenyl)-1-(pyridin-4-ylmethyl)pyrrolidin-2-one and 4-(4-fluorophenyl)-1-((3-methylpyridin-4-yl)methyl)pyrrolidin-2-one, a salt, solvate, tautomer or enantiomer thereof, and any mixtures thereof.

In certain embodiments, the compound of formula 1 is a compound of formula 14:

14

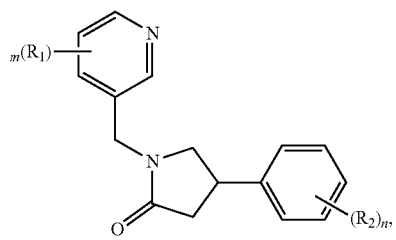

wherein:
each instance of $R_1$ and $R_2$ is independently selected from the group consisting of F, Cl, Br, I, $C_1$-$C_6$ alkyl (such as but not limited to $CH_3$), $C_1$-$C_6$ haloalkyl (such as but not limited to $CF_3$), CN and —$NO_2$, provided that at least one instance of $R_1$ or $R_2$ is F; and m and n are independently selected from the group consisting of 0, 1, 2, 3, 4 and 5;
a salt, solvate, tautomer or enantiomer thereof, and any mixtures thereof.

In certain embodiments, the compound of formula 1 or 14 is at least one selected from the group consisting of:

15

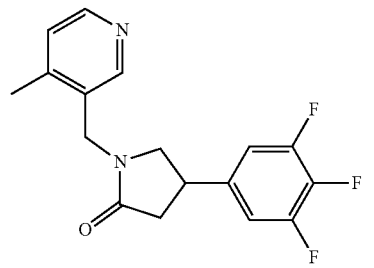

16

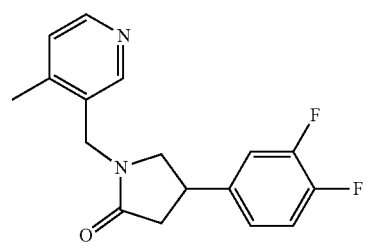

17

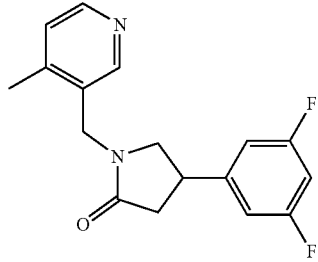

18

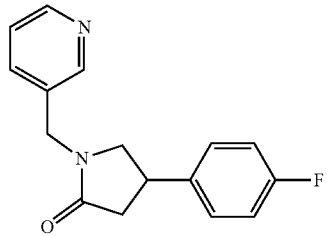

19

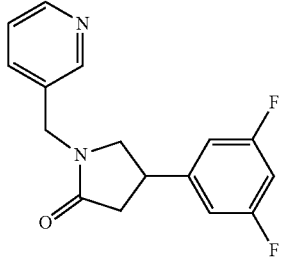

20

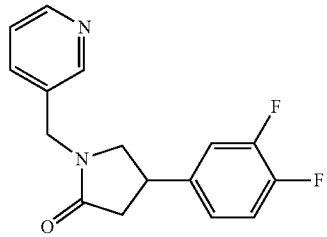

21

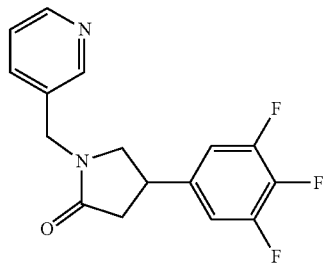

22

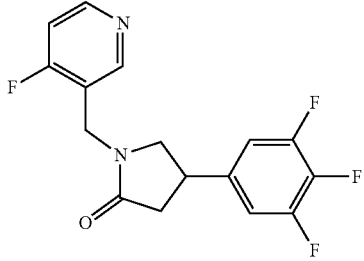

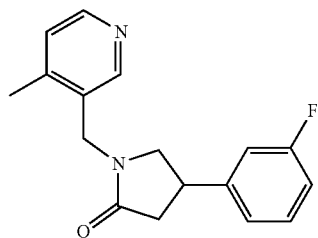

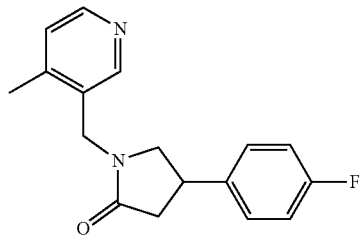

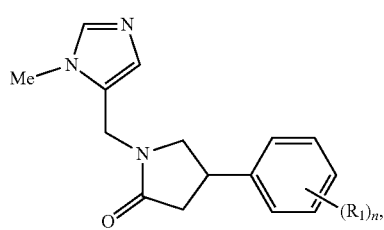

wherein at least one instance of F is $^{18}$F, a salt, solvate, tautomer or enantiomer thereof, and any mixtures thereof.

In certain embodiments, the compound of formula 1 or 14 is selected from the group consisting of: 1-((4-methylpyridin-3-yl)methyl)-4-(3,4,5-trifluorophenyl) pyrrolidin-2-one; 4-(3,4-difluorophenyl)-1-((4-methylpyridin-3-yl)methyl) pyrrolidin-2-one; 4-(3,5-difluorophenyl)-1-((4-methylpyridin-3-yl)methyl)pyrrolidin-2-one; 4-(4-fluoro phenyl)-1-(pyridin-3-ylmethyl)pyrrolidin-2-one; 4-(3,5-difluorophenyl)-1-(pyridin-3-ylmethyl)pyrrolidin-2-one; 4-(3,4-difluorophenyl)-1-(pyridin-3-ylmethyl)pyrrolidin-2-one; 1-(pyridin-3-ylmethyl)-4-(3,4,5-trifluorophenyl)pyrrolidin-2-one; 1-((4-fluoropyridin-3-yl)methyl)-4-(3,4,5-trifluorophenyl)pyrrolidin-2-one; 4-(3-fluorophenyl)-1-((4-methyl pyridin-3-yl)methyl)pyrrolidin-2-one; 4-(3-fluorophenyl)-1-(pyridin-3-ylmethyl)pyrrolidin-2-one, and 4-(4-fluorophenyl)-1-((4-methylpyridin-3-yl)methyl)pyrrolidin-2-one, a salt, solvate, tautomer or enantiomer thereof, and any mixtures thereof.

In a further aspect, the invention of formula 1 is a compound of formula 26:

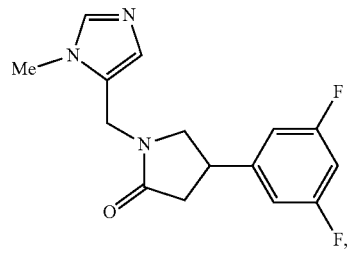 [SMILES: Cn1cncc1CN1CC(c2cc(F)cc(F)c2)CC1=O]

wherein:

each instance of $R_1$ is independently selected from the group consisting of F, Cl, Br, I, $C_1$-$C_6$ alkyl (such as but not limited to $CH_3$), $C_1$-$C_6$ haloalkyl (such as but not limited to $CF_3$), CN and —$NO_2$, provided that at least one instance of $R_1$ is F; and n is selected from the group consisting of 1, 2, 3, 4 and 5, a salt, solvate, tautomer or enantiomer thereof, and any mixtures thereof.

In certain embodiments, the compound of formula 1 or 26 is 27:

wherein at least one instance of F is $^{18}$F, a salt, solvate, tautomer or enantiomer thereof, and any mixtures thereof.

In certain embodiments, the compound of formula 1 or 26 is 4-(3,5-difluorophenyl)-1-((1-methyl-1H-imidazol-5-yl)methyl)pyrrolidin-2-one, a salt, solvate, tautomer or enantiomer thereof, and any mixtures thereof.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In certain embodiments, isotopically labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as C, $^{18}$F, $^{15}$O and $^{13}$N, is useful in Positron Emission Topography (PET) studies for examining target protein concentration and/or substrate receptor occupancy. Isotopically-labeled compounds are prepared by any suitable method or by processes using an appropriate isotopically-labeled reagent in place of the non-labeled reagent otherwise employed.

While the invention encompasses, in various embodiments, any isotope of any atom as shown in the structures, in various embodiments, $^{18}$F may be substituted for F at any position or at multiple positions.

In certain embodiments, the compounds described herein are labeled by other means, including, but not limited to, the use of chromophores or fluorescent moieties, bioluminescent labels, or chemiluminescent labels.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Methods

In one aspect, the invention provides a method of decreasing the amount of unbound synaptic vesicle glycoprotein 2A (SV2A) in at least one region of the body of a subject. In certain embodiments, the method comprises administering to a subject at least one compound of the invention, or a composition comprising the same. In other embodiments, the compound is administered to the subject by any known means of administration, and optionally in a pharmaceutical composition further comprising at least one excipient as appropriate to deliver the compound to the intended region of the subject's body. In various embodiments of this aspect or any aspect described herein, the at least one region of the subject's body may the subject's brain or a portion thereof. In various embodiments of this aspect or any aspect described herein, the at least one region of the subject's body may be the pancreas.

In one aspect, the invention provides a method of imaging at least one region of the body of a subject. In certain embodiments, the method comprises administering to a subject at least one compound of the invention, or a composition comprising the same, and detecting the at least one compound by positron emission tomography in at least one region of the body of the subject, thereby generating an image of the at least one region of the body of the subject. In certain embodiments, the compound is administered to the subject by any known means of administration, and optionally in a pharmaceutical composition further comprising at least one excipient as appropriate to deliver the compound to the subject's body.

The compounds of the invention can be utilized as radiotracers for PET imaging. In certain embodiments, the region of the brain may be the cingulate cortex, frontal cortex, insular cortex, nucleus accumbens, occipital cortex, temporal cortex, putamen, caudate nucleus, thalamus, cerebellum, hippocampus, globus pallidus, amygdala, brainstem, pons, centrum semiovale, or any combinations thereof. In non-limiting examples, FIGS. 5-7, 8A-8K, 9A-9C, 10A-10F, and 11 depict PET images and data acquired according to this method and procedures are discussed in Examples 3-5. A person of skill in the art is familiar with methods of PET imaging and may readily apply such knowledge in combination with the present disclosure to generate PET images and data using the compounds disclosed herein.

In one aspect, the invention further provides a method of detecting and/or measuring synaptic loss in a subject. In certain embodiments, the method comprises administering to a subject at least one compound of the invention, or a composition comprising the same; and detecting and/or measuring the at least one compound by PET in at least one region of the brain of the subject. In other embodiments, the detecting and/or measuring the at least one compound by PET is used to determine or evaluate the SV2A level in the at least one region of the brain of the subject. In a non-limiting example, the amount of the least one compound measured and/or detected by PET is compared or correlated to a predetermined reference (which is known to have, or not to have, significant synaptic loss), wherein the amount of the least one compound measured and/or detected by PET is correlated with the SV2A level. In yet other embodiments, if the SV2A level in the subject is lower than in the reference known not to have significant synaptic loss, decreased synaptic density is detected in the subject. Validation of SV2A in combination with compounds of the invention as a biomarker of synaptic density is exemplified in Example 4. In non-limiting examples, FIGS. 9A-9C, 10A-10F, and 11 depict PET detection of changes in synaptic density in the brain of patients with epilepsy, AD, and Parkinson's disease (PD).

In certain embodiments, the compound is administered to the subject by any known means of administration, and optionally in a pharmaceutical composition further comprising at least one excipient as appropriate to deliver the compound to the subject's brain or other organs such as the pancreas. The compound may be detected using methods of PET familiar to a person of skill in the art and described and exemplified in Examples 2-5 and the Figures of the invention. As disclosed herein, the compounds of the invention bind to SV2A and can be detected by PET. Competitive binding assays demonstrating the affinity for SV2A possessed by compounds of the invention are exemplified in Example 2.

A level of SV2A in a region of the brain or other organs such as the pancreas can be determined by calculating a distribution volume ($V_T$) and in turn binding potential ($BP_{ND}$). These values, along with the dissociation constant ($K_D$), can be used to calculate target protein density using equations familiar to a person of skill in the art. Further details are illustrated in Example 3-5 and FIGS. 8A-8K, 9A-9C, 10A-10F, and 11. Reference levels for SV2A can be calculated by determining typical values for groups of patients stratified by variables such as age by using the disclosed methods. Alternatively, reference levels can be determined by measuring the concentration of SV2A in vitro as described in Example 2.

In one aspect, the invention provides a method of detecting a neurodegenerative, neurological, psychiatric, and/or metabolic disease, or any other diseases/disorders where involvement of synaptic disruptions and/or abnormalities is present, in a subject. In certain embodiments, the method comprises administering to a subject at least one compound of the invention, or a composition comprising the same; detecting and/or measuring the at least one compound by PET in at least one region of the subject's body; determining the SV2A level in the at least one region of the subject's body and comparing it to a reference (which is known to be derived from a subject who has, or does not have, the disease); wherein, if the SV2A level in the at least one region of the subject's body is lower than in the reference from a subject known not to have the disease, the disease is detected in the subject. In the non-limiting example of AD, altered synaptic density is a leading indicator of cognitive impairment and AD, as exemplified in FIGS. 10A-10F. In certain embodiments, the disease is in pre-clinical or prodromal stage. The manner in which the compounds are provided to the patients, as well as the methods for determining a level and reference level for SV2A in a region of the brain of the patient, are illustrated elsewhere herein, such as in Example 5 and FIGS. 9A-9C, 10A-10F, and 11.

In one aspect, the invention provides a method of detecting and/or measuring a seizure onset zone in a subject with epilepsy, stroke, traumatic brain injury, Parkinson's disease or autism. In various embodiments, the method comprises administering to the subject at least one compound or at least one pharmaceutical composition of the invention; detecting the at least one compound by PET in at least one region of the brain of the subject and determining a level of SV2A in the at least one region of the brain of the subject. Because, PET detection allows spatial resolution of the level of SV2A in the region of interest, if an area within the at least one region has lower SV2A level than the rest of the at least one region, the area is identified as a seizure onset zone.

In one aspect, the invention provides a method of detecting an ischemic area in a subject with stroke. In various embodiments, the method comprises administering to the subject at least one compound or at least one pharmaceutical composition of the invention; detecting the at least one compound by PET in at least one region of the brain of the subject and determining a level of SV2A in the at least one region of the brain of the subject. Because, PET detection allows spatial resolution of the level of SV2A in the region of interest, if an area within the at least one region has lower SV2A level than the rest of the at least one region, the area is identified as being ischemic.

Administration/Dosage/Formulations

Administration of the compounds and/or compositions of the present invention to a patient, preferably a mammal, more preferably a human, may be carried out using known procedures, at dosages and for periods of time effective to perform an imaging method contemplated in the invention. An effective amount of the compound necessary for adequate signal for imaging may vary according to factors such as the state of a disease or disorder in the patient; the age, sex, and weight of the patient; and the equipment used to detect the compound of the invention. One of ordinary skill in the art would be able to study the relevant factors and make the determination regarding the effective amount of the compound without undue experimentation.

Actual dosage levels of the active ingredients in the pharmaceutical compositions of this invention may be varied so as to obtain an amount of the active ingredient that is effective to achieve successful imaging for a particular patient, composition, and mode of administration, without being toxic to the patient.

In certain embodiments, the compositions of the invention are formulated using one or more pharmaceutically acceptable excipients or carriers. In certain embodiments, the pharmaceutical compositions of the invention comprise an effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In certain embodiments, the dose of a compound of the invention is from about 1 mg and about 2,500 mg. In certain embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in certain embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In certain embodiments of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 2003/0147952; 2003/0104062; 2003/0104053; 2003/0044466; 2003/0039688; and 2002/0051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Materials and Methods

The materials and methods used in the following illustrative examples are here described. All reagents and solvents were obtained from commercial sources and used without further purification unless noted otherwise. Proton, carbon and fluorine nuclear magnetic resonance, ($^1$H NMR, $^{13}$C NMR and $^{19}$F NMR) spectra were recorded on an Agilent 400 MHz or 600 MHz NMR spectrometer. Chemical shifts are reported in parts per million, with the solvent resonance as the internal standard (CDCl$_3$: 7.26 ppm; DMSO-d$_6$: 2.49 ppm). Melting point was examined on an Electrothermal Mel-Temp instrument. High resolution mass spectrometry results were determined on a LC-MS/MS system including a Thermo Scientific LTQ-Orbitrap XL mass spectrometer and a Waters nanoACQUITY ultra high performance liquid chromatography instrument. HPLC-MS was performed with an Agilent 1200RRLC/6110SQD SYSTEM. Radio-HPLC systems include a Shimadzu LC-20A pump, a Knauer K200 UV detector, Shimadzu SPD-M20A PDA or SPD-20A UV detector, and a Bioscan γ-flow detector. [$^{18}$F]Fluoride was produced via the $^{18}$O(p, n) $^{18}$F nuclear reaction in a 16.5-MeV GE PETtrace cyclotron. H$_2$$^{18}$O was obtained from Huayi Isotopes. Anion exchange CHROMA-FIX™ cartridges (PS-HCO$_3$) were purchased from Macherey-Nagel. Solid-phase extraction (SPE) cartridges were purchased from Waters Associates. All chemicals used in this study were of ≥95% purity, based on HPLC, LC-MS, or NMR. The teachings of Finnema, et al., 2016, Sci. Transl. Med. 2016:8 are incorporated herein by reference.

Example 1

Synthesis of Precursors for $^{18}$F-3, $^{18}$F-4, $^{18}$F-5, $^{18}$F-6, F-11, $^{18}$F-12, $^{18}$F-13, $^{18}$F-18, and $^{18}$F-24 triphenyl phosphorene (6.0 g, 17.2 mmol) in anhydrous CH$_2$Cl$_2$ (20 mL). The reaction mixture was stirred for 30 min at 5° C. and concentrated in vacuo. A mixture of hexanes and diethyl ether (150 mL, 10:1, v/v) was added, and the suspension was stirred for 2 h at room temperature. Filtration of the suspension and evaporation of the solvents afford the intermediate as a white solid (4.5 g).

The synthetic intermediate (4.5 g, 14.9 mmol) was dissolved in nitromethane (2.5 mL, 46.7 mmol) under argon and cooled at 5° C. 1,8-Diazabicyclo[5.4.0]undec-7-ene (DBU, 2.62 g, 17.2 mmol) was added dropwise, and the mixture was stirred at 5° C. for 1 h. The reaction was quenched with saturated NH$_4$Cl (20 mL), acidified with aqueous HCl (2 M) until the pH of the mixture reached 2, and extracted with EtOAc (25 mL×3). The combined organic extracts were washed with brine (50 mL), dried over Na$_2$SO$_4$, filtered, and concentrated in vacuo to provide 29 as a yellow oil (6.7 g, quantitative), which was used in the next step of synthesis without further purification. $^1$H NMR (CDCl$_3$, 400 MHz): δ 7.70-7.53 (m, 2H), 7.22 (m, 1H), 7.07 (td, J=7.7, 1.8 Hz, 1H), 4.82-4.68 (m, 1H), 4.68-4.57 (m, 1H), 4.18-4.01 (m, 2H), 4.01-3.84 (m, 1H), 2.73 (ddd, J=7.7, 3.6, 1.6 Hz, 2H), 1.18 (t, J=7.1 Hz, 3H).

4-(3-Iodophenyl)pyrrolidin-2-one (30): A solution of 29 (0.545 g, 1.5 mmol) in ethanol (5 mL) was degassed with argon for 5 min. Raney-Ni (50% in water, 0.8 mL) was added, and the suspension was stirred under an atmosphere of hydrogen at room temperature for 2 days. The mixture was filtered through a layer of Celite and the filtrate was concentrated in vacuo. The synthetic intermediate was dissolved in toluene (50 mL), heated for 3 h under reflux conditions, and concentrated in vacuo. The crude product

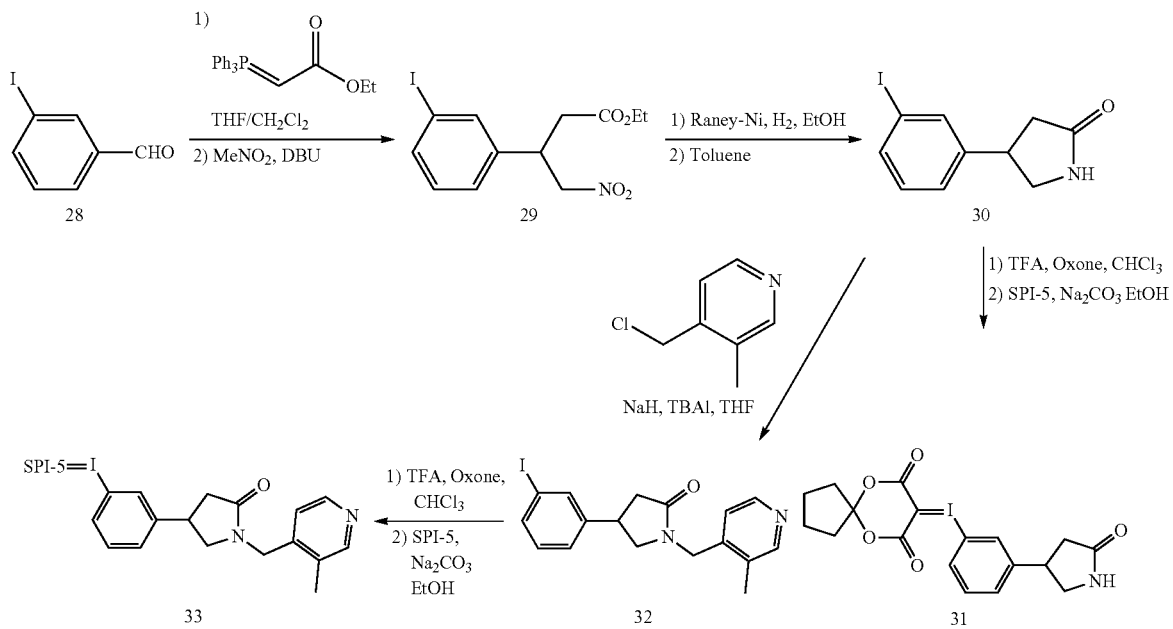

Scheme 1. Synthesis of radiofluorination precursors 31 and 33.

Ethyl 3-(3-iodophenyl)-4-nitrobutanoate (29): To a solution of 3-iodobenzaldehyde (28, 4.0 g, 17.2 mmol) in anhydrous THF (10 mL) under argon and cooled at 5° C. was dropwise added a solution of carbethoxymethylene was purified on a silica gel column eluting with 0-10% EtOH/EtOAc to give 30 as a yellow oil (430 mg, 30%). $^1$H NMR (CDCl$_3$, 400 MHz): δ 7.59 (d, J=6.41 Hz, 2H), 7.21 (d, J=7.74 Hz, 1H), 7.07 (t, J=8.00 Hz, 1H), 5.99 (s, 1H), 3.76 (t, J=8.76 Hz, 1H), 3.62 (p, J=8.34 Hz, 1H), 3.38 (t, J=7.40 Hz, 1H), 2.71 (dd, J=16.91, 8.94 Hz, 1H), 2.44 (dd, J=16.90, 8.58 Hz, 1H).

8-((3-(5-Oxopyrrolidin-3-yl)phenyl)-λ³-iodanylidene)-6,10-dioxaspiro[4.5]decane-7,9-dione (31)

To a solution of 30 (300 mg, 1.04 mmol) in CHCl₃ (1.5 mL) was added trifluoroacetic acid (TFA, 2.5 mL, 32.4 mmol) followed by Oxone (480 mg, 1.56 mmol). The reaction mixture was stirred for 2 h until it turned to a white suspension. The volatile contents were removed in vacuo. The residue was suspended in ethanol (2 mL) and 6,10-dioxaspiro[4.5]decane-7,9-dione (SPI-5, 220 mg, 1.29 mmol) was added, followed by 10% Na₂CO₃ until the pH of the mixture reached 10. The reaction mixture was stirred for 3 h, diluted with water, and extracted with CH₂Cl₂ (1.0 mL×3). The organic phases were combined, dried over MgSO₄, filtered, and concentrated in vacuo. The crude product was purified on a silica gel column eluting with 10-40% EtOH/EtOAc to afford 31 as a white solid (120 mg, 25%). ¹H NMR (DMSO-d₆, 600 MHz): δ 7.72 (s, 1H), 7.59 (d, J=7.99 Hz, 1H), 7.47 (d, J=7.76 Hz, 1H), 7.39 (t, J=7.79 Hz, 1H), 3.60 (m, 2H), 3.13 (m, 1H), 2.50 (dd, J=8.93 Hz, 1H, overlap with DMSO residue peaks), 2.22 (dd, J=16.29, 8.77 Hz, 1H), 1.94 (m, 4H), 1.65 (m, 4H). ¹³C NMR (DMSO-d₆, 100 MHz): δ 175.86, 163.98 (2C), 146.34, 131.58, 131.28, 130.84, 129.80, 116.96, 112.59, 48.70, 39.78 (overlap with DMSO residue peaks), 38.02, 37.22 (2C), 23.18 (2C). HRMS: calculated for C₁₈H₁₈INO₅ ([M+Na]⁺) 478.0122; found, 478.0162.

4-(3-Iodophenyl)-1-((3-methylpyridin-4-yl)methyl)pyrrolidin-2-One (32)

To a solution of 30 (250 mg, 0.87 mmol) in anhydrous THF (3.0 mL) under argon and cooled at 0° C. was added sodium hydride (110 mg, 2.75 mmol). Tetrabutylammonium iodide (TBAI, 17 mg, 0.05 mmol) and 4-(chloromethyl)-3-methylpyridine hydrochloride (180 mg, 0.96 mmol) were added after 30 min. The reaction mixture was kept stirring for 16 h at room temperature, then quenched with saturated NaHCO₃ solution (6 mL) and extracted with EtOAc (3 mL×3). The organic extracts were combined, dried over Na₂SO₄ and concentrated in vacuo. The crude product was purified on a silica gel column eluting with 0-10% EtOH/EtOAc to afford compound 32 as a light brown oil (256 mg, 68%). ¹H NMR (CDCl₃, 400 MHz): δ 8.41 (s, 2H), 7.58 (dt, J=7.80, 1.38 Hz, 1H), 7.51 (m, 1H), 7.13 (dt, J=7.75, 1.41 Hz, 1H), 7.05 (d, J=10.10 Hz, 1H), 7.03 (d, J=7.47 Hz, 1H), 4.57 (d, J=15.49 Hz, 1H), 4.42 (d, J=15.48 Hz, 1H), 3.59 (m, 1H), 3.53 (p, J=8.61 Hz, 1H), 3.23 (m, 1H), 2.88 (dd, J=16.99, 8.80 Hz, 1H), 2.60 (dd, J=17.00, 8.07 Hz, 1H), 2.30 (s, 3H).

8-((3-(1-((3-Methylpyridin-4-yl)methyl)-5-oxopyrrolidin-3-yl)phenyl)-λ³-iodaneylidene)-6,10-dioxaspiro[4.5]decane-7,9-dione (33)

Compound 33 was prepared in procedures similar to those described above for 31. Yield: 30%. ¹H NMR (DMSO-d₆, 400 MHz): δ 8.35 (s, 2H), 7.72 (d, J=1.76 Hz, 1H), 7.59 (dt, J=7.95, 1.35 Hz, 1H), 7.47 (d, J=7.81, 1.24 Hz, 1H), 7.38 (t, J=7.80 Hz, 1H), 7.11 (d, J=4.83 Hz, 1H), 4.51 (d, J=16.07 Hz, 1H), 4.33 (d, J=16.11 Hz, 1H), 3.70 (p, J=8.26 Hz, 1H), 3.61 (t, J=8.74 Hz, 1H), 3.20 (dd, J=9.29, 7.31 Hz, 1H), 2.76 (dd, J=16.43, 8.68 Hz, 1H), 2.50 (dd, overlap with DMSO solvent residue peak, 1H), 2.23 (s, 3H), 1.94 (m, 4H), 1.63 (m, 4H).

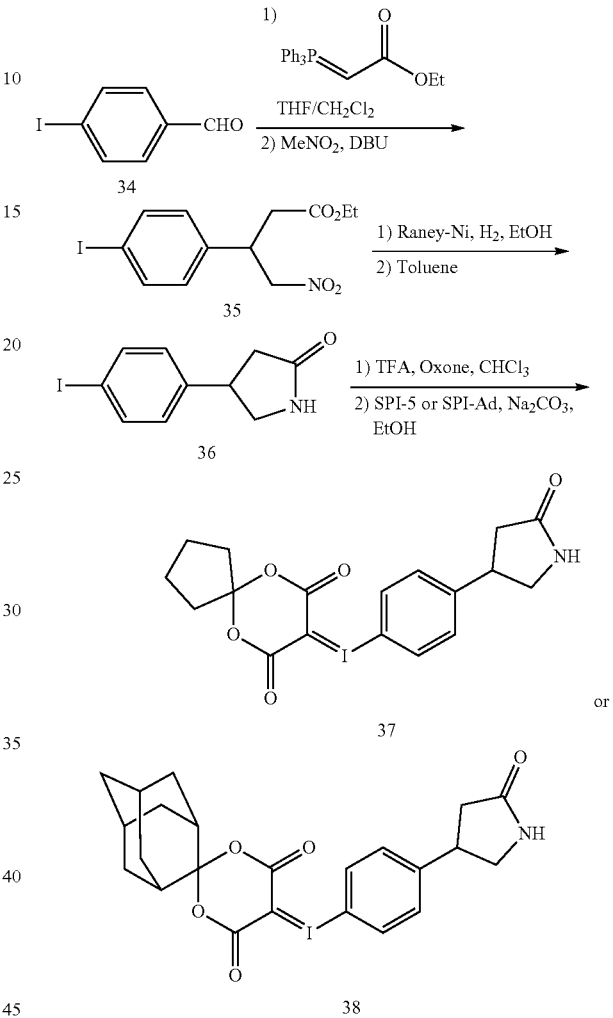

Scheme 2. Synthesis of radiofluorination precursors 37 and 38.

Ethyl 3-(4-iodophenyl)-4-nitrobutanoate (35)

Compound 35 was prepared in procedures similar to those described above for 29. Yield: 96%. ¹H NMR (CDCl₃, 400 MHz): δ 7.67 (d, J=8.4 Hz, 2H), 6.99 (d, J=8.4 Hz, 2H), 4.71 (dd, J=12.7, 6.8 Hz, 1H), 4.61 (dd, J=12.7, 8.2 Hz, 1H), 4.19-4.01 (m, 2H), 4.00-3.88 (m, 1H), 2.73 (dd, J=7.5, 4.4 Hz, 2H), 1.19 (t, J=7.2 Hz, 3H).

4-(4-Iodophenyl)pyrrolidin-2-one (36)

Compound 36 was prepared in procedures similar to those described above for 30. Yield: 32%. ¹H NMR (CDCl₃, 400 MHz): δ 7.65 (d, J=8.36 Hz, 2H), 6.99 (d, J=8.26 Hz, 2H), 5.55 (s, 1H), 3.76 (t, J=8.76 Hz, 1H), 3.64 (p, J=8.24 Hz, 1H), 3.35 (t, J=8.09 Hz, 1H), 2.71 (dd, J=16.88, 8.90 Hz, 1H), 2.43 (dd, J=16.89, 8.65 Hz, 1H).

8-((4-(5-Oxopyrrolidin-3-yl)phenyl)-λ³-iodanylidene)-6,10-dioxaspiro[4.5]Decane-7,9-Dione (37)

Compound 37 was prepared in procedures similar to those described above for 31. Yield: 31%. ¹H NMR (DMSO-$d_6$, 400 MHz): δ 7.68 (d, J=8.19 Hz, 2H), 7.37 (d, J=8.37 Hz, 2H), 3.60 (m, 2H), 3.14 (t, J=7.85 Hz, 1H), 2.47 (dd, 1H, overlap with DMSO residue peak), 2.26 (m, 1H), 1.90 (m, 4H), 1.64 (m, 4H).

(1r,3r,5r,7r)-5'-((4-(5-Oxopyrrolidin-3-yl)phenyl)-λ³-iodanylidene) spiro[adamantane-2,2'-[1,3]dioxane]-4',6'-dione (38)

Compound 38 was prepared in procedures similar to those described above for 31, with (1r,3r,5r,7r)-spiro[adamantane-2,2'-[1,3]dioxane]-4',6'-dione (SPI-Ad) added instead of 6,10-dioxaspiro[4.5]decane-7,9-dione (SPI-5) in the second stage of the reaction. Yield: 37%. ¹H NMR (DMSO-$d_6$, 400 MHz): δ 7.68 (d, J=8.19 Hz, 2H), 7.37 (d, J=8.37 Hz, 2H), 3.60 (m, 2H), 3.14 (t, J=7.85 Hz, 1H), 2.47 (dd, 1H overlap with solvent residue peak), 2.29 (m, 2H), 2.26 (dd, 1H), 1.90 (m, 4H), 1.76 (m, 2H), 1.64 (m, 4H), 1.62 (m, 1H), 1.02 (m, 1H).

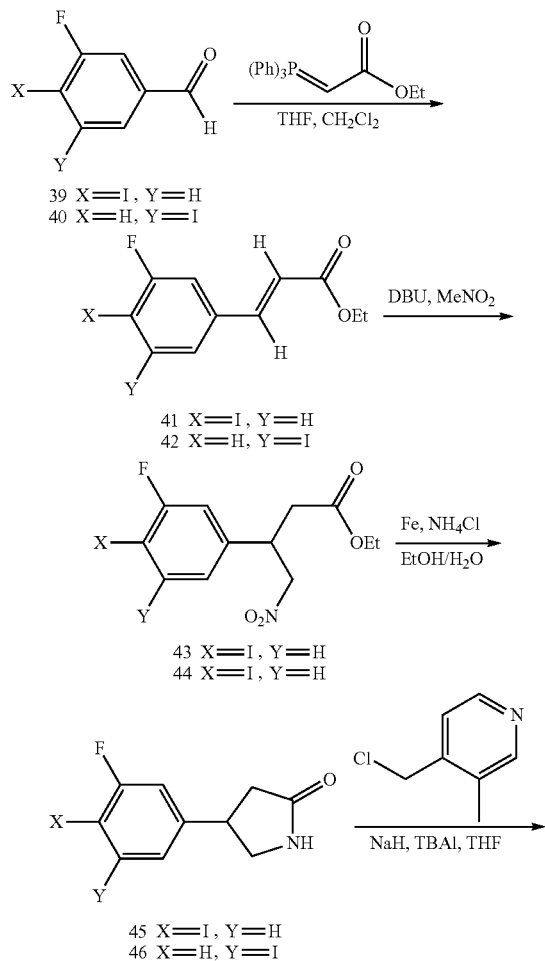

Scheme 3. Synthesis of radiofluorination precursors 49 and 50.

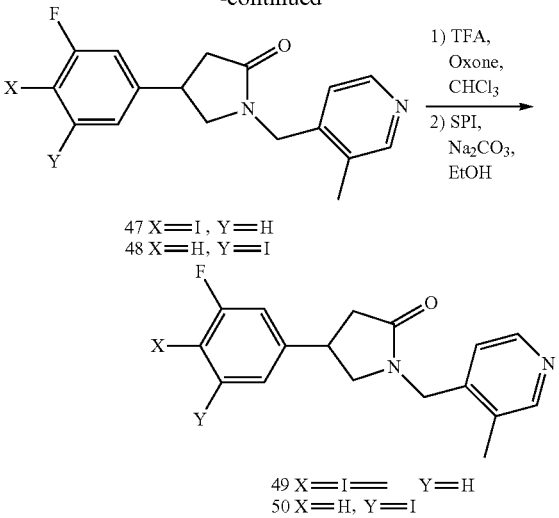

Ethyl (E)-3-(3-fluoro-4-iodophenyl)acrylate (41)

To a solution of 3-fluoro-4-iodobenzaldehyde (39, 1.0 g, 3.80 mmol) in anhydrous THF (3 mL) under argon and cooled at 0° C. was added dropwise a solution of carbethoxymethylene triphenyl phosphorene (1.49 g, 4.19 mmol) in anhydrous $CH_2Cl_2$ (5 mL). The reaction mixture was kept stirring for 1 h at 5° C., and then concentrated in vacuo. A mixture of hexanes and diethyl ether (15 mL, 4:1, v/v) was added and the suspension stirred for 10 min at room temperature. Filtration of the mixture through a silica gel plug and evaporation of the solvents afforded compound 41 as a white solid (1.2 g, quantitative), which was used in the next step of synthesis without further purification. ¹H NMR (CDCl₃, 400 MHz): δ 7.75 (t, J=7.29 Hz, 1H), 7.55 (d, J=16.21 Hz, 1H), 7.18 (d, J=8.75 Hz, 1H), 7.03 (d, J=8.17 Hz, 1H), 6.43 (d, J=15.99 Hz, 1H), 4.25 (q, J=7.11 Hz, 2H), 1.32 (t, J=7.11 Hz, 3H).

Ethyl (E)-3-(3-fluoro-5-iodophenyl)acrylate (42)

Compound 42 was prepared in procedures similar to those described above for 41. Yield: Quantitative. ¹H NMR (CDCl₃, 400 MHz): δ 7.63 (s, 1H), 7.51 (d, J=15.98 Hz, 1H), 7.42 (d, J=7.57 Hz, 1H), 7.16 (d, J=9.23 Hz, 1H), 6.39 (d, J=16.00 Hz, 1H), 4.25 (q, J=7.13 Hz, 2H), 1.32 (t, J=7.11 Hz, 3H).

Ethyl 3-(3-fluoro-4-iodophenyl)-4-nitrobutanoate (43)

Compound 41 (1.0 g, 3.12 mmol) was dissolved in nitromethane (0.5 mL, 9.34 mmol) under argon and cooled at −20° C. 1,8-diazabicyclo[5.4.0]undec-7-ene (DBU, 0.52 mL, 3.45 mmol) was added and the reaction mixture was kept stirring for 2 h at −20° C. Water (2 mL) was added, followed by 12 N HCl until the pH of the mixture reached 1. The mixture was extracted with EtOAc (2 mL×3). The organic extracts were combined, dried over $Na_2SO_4$ and concentrated in vacuo. The crude product was purified on a silica gel column eluting with 0-15% EtOAc/hexanes to afford compound 43 as a white solid (1.0 g, 85%). ¹H NMR (CDCl₃, 400 MHz): δ 7.70 (t, J=6.98 Hz, 1H), 6.94 (d, J=8.60 Hz, 1H), 6.79 (d, J=8.01 Hz, 1H), 4.70 (dd, J=12.18, 8.54 Hz, 1H), 4.61 (dd, J=12.02, 8.45 Hz, 1H), 4.09 (q, J=7.04 Hz, 2H), 3.95 (p, J=7.18 Hz, 1H), 2.71 (dd, J=6.91, 3.51 Hz, 2H), 1.19 (t, J=6.71 Hz, 3H).

Ethyl 3-(3-fluoro-5-iodophenyl)-4-nitrobutanoate (44)

Compound 44 was prepared in procedures similar to those described above for 43. Yield: 88%. $^1$H NMR (CDCl$_3$, 400 MHz): δ 7.35 (dd, J=6.84, 1.61 Hz, 2H), 6.92 (d, J=9.17 Hz, 1H), 4.63 (m, 2H), 4.10 (q, J=7.03 Hz, 2H), 3.92 (p, J=7.37 Hz, 1H), 2.71 (m, 2H), 1.19 (t, J=7.14 Hz, 3H).

4-(3-Fluoro-4-iodophenyl)pyrrolidin-2-one (45)

To a suspension of compound 43 (0.9 g, 2.39 mmol) and iron powder (1.33 g, 23.8 mmol) in a mixture of ethanol and water (12 mL, 2:1, v/v) was added NH$_4$Cl (3.83 g, 71.6 mmol). After stirring for 16 h at room temperature, the pH of the mixture was adjusted to pH 14 with saturated NaOH solution, then extracted with EtOAc (5 mL×3). The organic extracts were combined, dried over Na$_2$SO$_4$ and concentrated in vacuo to afford compound 45 as a white solid (0.37 g, 51%). This crude product was used in the next step of synthesis without further purification. $^1$H NMR (CDCl$_3$, 400 MHz): δ 7.69 (t, J=6.98 Hz, 1H), 6.96 (d, J=8.00 Hz, 1H), 6.81 (d, J=7.41 Hz, 1H), 5.62 (s, 1H), 3.77 (t, J=8.04 Hz, 1H), 3.66 (p, J=7.62 Hz, 1H), 3.36 (t, J=8.44 Hz, 1H), 2.73 (dd, J=16.97, 8.55 Hz, 1H), 2.42 (dd, J=15.87, 8.58 Hz, 1H).

4-(3-Fluoro-5-iodophenyl)pyrrolidin-2-one (46)

Compound 46 was prepared in procedures similar to those described above for 45. Yield: 85%. $^1$H NMR (CDCl$_3$, 400 MHz): δ 7.37 (s, 1H), 7.33 (d, J=7.76 Hz, 1H), 6.92 (d, J=9.06 Hz, 1H), 5.68 (s, 1H), 3.76 (t, J=8.82 Hz, 1H), 3.63 (p, J=7.96 Hz, 1H), 3.37 (m, 1H), 2.72 (dd, J=16.97, 8.98 Hz, 1H), 2.41 (dd, J=16.80, 8.32 Hz, 1H).

4-(3-Fluoro-4-iodophenyl)-1-((3-methylpyridin-4-yl)methyl)pyrrolidin-2-one (47)

Compound 47 was prepared in procedures similar to those described above for 32. Yield: 87%. $^1$H NMR (CDCl$_3$, 400 MHz): δ 8.40 (s, 2H), 7.67 (q, J=7.10 Hz, 1H), 7.01 (m, 1H), 6.89 (d, J=7.99 Hz, 1H), 6.74 (d, J=7.68 Hz, 1H), 4.60 (dd, J=15.48, 5.30 Hz, 1H), 4.38 (dd, J=15.46, 5.32 Hz, 1H), 3.59 (m, 2H), 3.22 (m, 1H), 2.90 (dd, J=16.62, 6.54 Hz, 1H), 2.58 (dd, J=15.84, 7.17 Hz, 1H), 2.29 (s, 3H).

4-(3-Fluoro-5-iodophenyl)-1-((3-methylpyridin-4-yl)methyl)pyrrolidin-2-one (48)

Compound 48 was prepared in procedures similar to those described above for 32. Yield: 47%. $^1$H NMR (CDCl$_3$, 400 MHz): δ 8.41 (s, 2H), 7.28 (m, 2H), 7.02 (m, 1H), 6.84 (d, J=9.37 Hz, 1H), 4.50 (m, 2H), 3.55 (m, 2H), 3.21 (m, 1H), 2.89 (dd, J=17.02, 8.79 Hz, 1H), 2.57 (dd, J=17.02, 7.87 Hz, 1H), 2.30 (s, 3H).

8-((2-Fluoro-4-(1-((3-methylpyridin-4-yl)methyl)-5-oxopyrrolidin-3-yl)phenyl)-λ$^3$-iodaneylidene)-6,10-dioxaspiro[4.5]decane-7,9-dione (49)

Compound 49 was prepared in procedures similar to those described above for 31. Yield: 36%. $^1$H NMR (DMSO-d$_6$, 400 MHz): δ 8.33 (s, 2H), 7.80 (t, J=7.18 Hz, 1H), 7.40 (d, J=9.48 Hz, 1H), 7.18 (d, J=8.15 Hz, 1H), 7.09 (d, J=4.71 Hz, 1H), 4.50 (d, J=16.0 Hz, 1H), 4.31 (d, J=16.1 Hz, 1H), 3.72 (p, J=8.15 Hz, 1H), 3.60 (t, J=8.79 Hz, 1H), 3.23 (t, J=8.36 Hz, 1H), 2.74 (dd, J=16.4, 8.74 Hz, 1H), 2.56 (dd, J=16.4, 9.14 Hz, 1H), 2.21 (s, 3H), 1.87 (m, 4H), 1.61 (m, 4H).

8-((3-Fluoro-5-(1-((3-methylpyridin-4-yl)methyl)-5-oxopyrrolidin-3-yl)phenyl)-λ$^3$-iodaneylidene)-6,10-dioxaspiro[4.5]decane-7,9-dione (50)

Compound 50 was prepared in procedures similar to those described above for 31. Yield: 15%. $^1$H NMR (DMSO-d$_6$, 400 MHz): δ 8.36 (s, 2H), 7.56 (s, 1H), 7.43 (m, 2H), 7.15 (m, 1H), 4.52 (d, J=15.95 Hz, 1H), 4.33 (d, J=16.04 Hz, 1H), 3.73 (m, 1H), 3.61 (t, J=8.78 Hz, 1H), 3.21 (m, 1H), 2.75 (dd, J=16.41, 8.67 Hz, 1H), 2.53 (m, 1H), 2.24 (s, 3H), 1.96 (m, 4H), 1.64 (m, 4H).

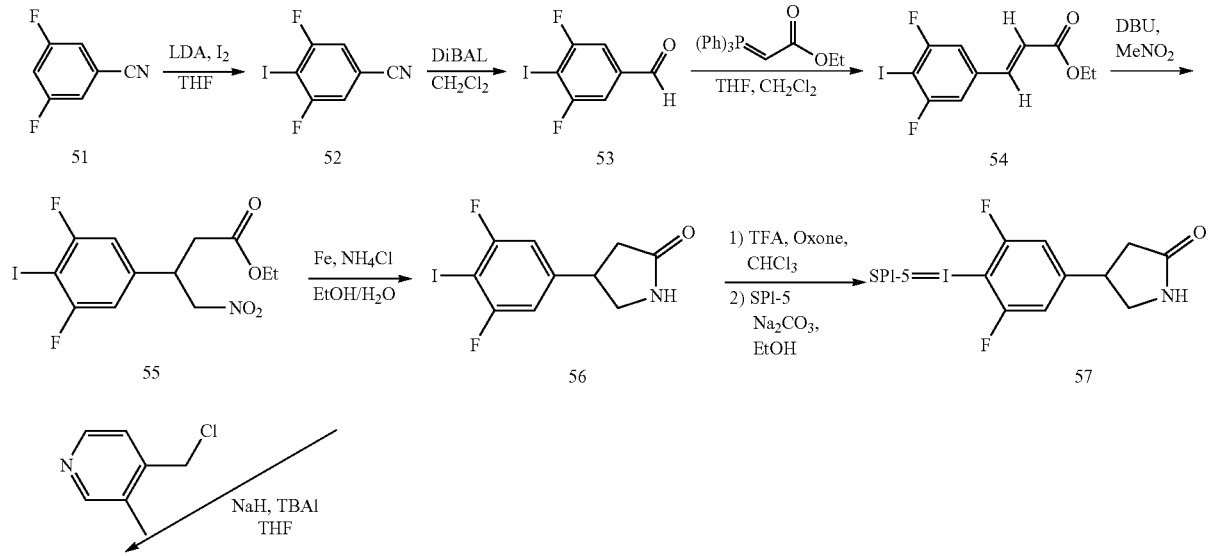

Scheme 4. Synthesis of radiofluorination precursors 57, 59, and (R)-59.

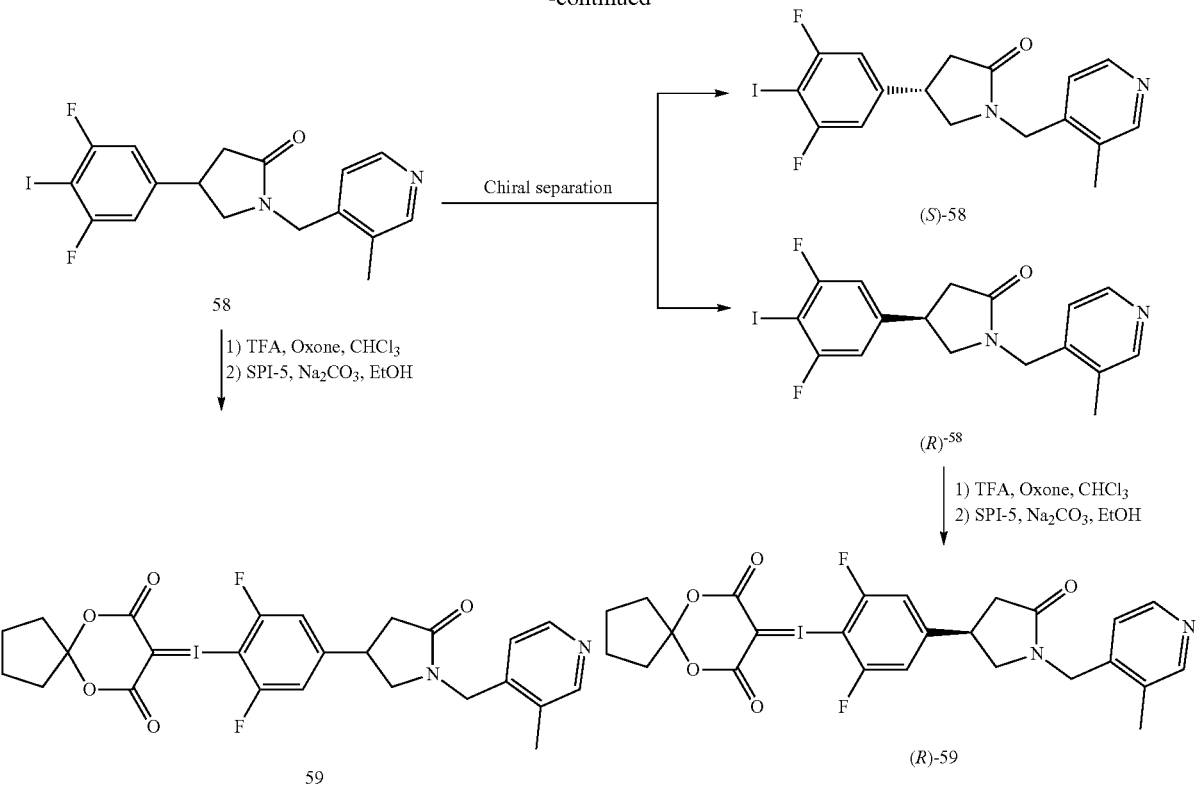

3,5-Difluoro-4-iodobenzonitrile (52): To a solution of 3,5-difluorobenzonitrile (51, 13.7 g, 98.5 mmol) in anhydrous tetrahydrofuran (THF, 130 mL) under argon and cooled at −78° C. was added dropwise a solution of lithium diisopropylamide (55 mL, 2 M in THF), followed by a solution of iodine (26.3 g, 103.6 mmol) in anhydrous THF (75 mL). The reaction was slowly warmed to room temperature, stirred for 1 h, and then quenched with 10% sodium thiosulfite solution (100 mL). The mixture was extracted with a 1:1 mixture of ethyl acetate/hexanes (50 mL×3). The combined organic phase was dried over $Na_2SO_4$ and concentrated in vacuo to afford compound 52 as a brownish solid (10.7 g, 41%). This crude product was used in the next step of synthesis without further purification. $^1$H NMR (CDCl$_3$, 400 MHz): δ 7.16(d, J=5.10 Hz, 2H).

3,5-Difluoro-4-iodobenzaldehyde (53): To a solution of 52 (10.7 g, 40.4 mmol) in anhydrous $CH_2Cl_2$ (85 mL) under argon and cooled at 0° C. was added dropwise a solution of diisobutylaluminium anhydride (40.5 mL, 1 M in $CH_2Cl_2$). The reaction was slowly warmed to room temperature, stirred for 1 h, and then quenched with 6 N HCl (85 mL). The mixture was extracted with $CH_2Cl_2$ (50 mL×3). The organic extracts were combined, dried over $Na_2SO_4$ and concentrated in vacuo to afford compound 53 as a white solid (9.7 g, 91%). This crude product was used in the next step of synthesis without further purification. $^1$H NMR (CDCl$_3$, 400 MHz): δ 9.91 (s, 1H), 7.37 (d, J=5.51 Hz, 2H).

Ethyl (E)-3-(3,5-difluoro-4-iodophenyl)acrylate (54)

Compound 54 was prepared in procedures similar to those described above for 41. Yield: Quantitative. $^1$H NMR (CDCl$_3$, 400 MHz): δ 7.54 (d, J=15.94 Hz, 1H), 7.03 (d, J=6.89 Hz, 2H), 6.45 (d, J=15.96 Hz, 1H), 4.27 (q, J=7.09 Hz, 2H), 1.33 (t, J=7.12 Hz, 3H).

Ethyl 3-(3,5-difluoro-4-iodophenyl)-4-nitrobutanoate (55)

Compound 55 was prepared in procedures similar to those described above for 43. Yield: 93%. $^1$H NMR (CDCl$_3$, 400 MHz): δ 6.80 (d, J=6.63 Hz, 2H), 4.72 (dd, J=12.98, 8.40 Hz, 1H), 4.61 (dd, J=12.98, 6.38 Hz, 1H), 4.12 (qd, J=7.14, 1.09 Hz, 2H), 3.97 (p, J=7.34 Hz, 1H), 2.72 (dd, J=7.12, 4.09 Hz, 2H), 1.21 (t, J=7.14 Hz, 3H).

4-(3,5-Difluoro-4-iodophenyl)pyrrolidin-2-one (56)

Compound 56 was prepared in procedures similar to those described above for 45. Yield: 46%. $^1$H NMR (CDCl$_3$, 400 MHz): δ 6.80 (d, J=7.60 Hz, 2H), 5.63 (s, 1H), 3.79 (t, J=8.77 Hz, 1H), 3.67 (p, J=7.62 Hz, 1H), 3.36 (t, J=8.44 Hz, 1H), 2.74 (dd, J=17.02, 8.72 Hz, 1H), 2.41 (dd, J=16.63, 8.10 Hz, 1H).

8-((2,6-Difluoro-4-(5-oxopyrrolidin-3-yl)phenyl)-$\lambda^3$-iodanylidene)-6,10-dioxaspiro[4.5]decane-7,9-dione (57)

Compound 57 was prepared in procedures similar to those described above for 31. Yield: 50%. $^1$H NMR (DMSO-d$_6$, 400 MHz): δ 7.27 (d, J=8.29 Hz, 2H), 3.60 (m, 2H), 3.13 (m, 1H), 2.50 (dd, J=8.93 Hz, 1H), 2.22 (dd, J=16.29, 8.77 Hz, 1H), 1.82 (m, 4H), 1.60 (m, 4H). $^{19}$F NMR (DMSO-d$_6$, 376 MHz): δ −73.64.

4-(3,5-Difluoro-4-iodophenyl)-1-((3-methylpyridin-4-yl)methyl) pyrrolidin-2-one (58)

Compound 58 was prepared in procedures similar to those described above for 32. Yield: 38%. $^1$H NMR (CDCl$_3$, 400 MHz): δ 8.41 (s, 2H), 7.02 (d, J=4.81 Hz, 1H), 6.72 (d, J=7.11 Hz, 2H), 4.61 (d, J=15.42 Hz, 1H), 4.39 (d, J=15.42 Hz, 1H), 3.60 (m, 2H), 3.21 (m, 1H), 2.91 (dd, J=16.87, 8.61 Hz, 1H), 2.56 (dd, J=16.86, 7.95 Hz, 1H), 2.30 (s, 3H).

8-((2,6-Difluoro-4-(1-((3-methylpyridin-4-yl)methyl)-5-oxopyrrolidin-3-yl)phenyl)-λ$^3$-iodanylidene)-6,10-dioxaspiro[4.5]decane-7,9-dione (59)

Compound 59 was prepared in procedures similar to those described above for 31. Yield: 31%. $^1$H NMR (DMSO-d$_6$, 400 MHz): δ 8.37 (s, 2H), 7.27 (d, J=8.29 Hz, 2H), 7.17 (s, 1H), 4.53 (d, J=15.7 Hz, 1H), 4.33 (d, J=15.9 Hz, 1H), 3.74 (m, 1H), 3.60 (m, 1H), 2.73 (dd, J=16.4, 8.9 Hz, 1H), 2.60 (dd, 1H), 2.20 (s, 3H), 1.82 (m, 4H), 1.59 (m, 4H). HRMS: calculated for C$_{25}$H$_{23}$F$_2$IN$_2$O$_5$[M+H]$^+$ 597.0693; found, 597.0743.

Chiral Separation of Enantiomers

The separation was conducted on a ChiralCel OD HPLC column (10 μm, 10×250 mm). Racemic 58 (100 mg) was dissolved in ethanol (1.0 mL), and 70 μL of the solution was injected in each separation. Mobile phase: 25/75 EtOH/hexane with 0.1% TEA, flow rate: 6 mL/min, the first compound eluting out from the column was the inactive enantiomer ((S)-58), while the second compound was the active enantiomer ((R)-58). The enantiomeric excess (ee.) was checked on an analytical ChiralCel OD column (10 μm, 4.6×250 mm). Mobile phase: 25/75 EtOH/hexane with 0.1% TEA, flow rate: 1.25 mL/min. Both enantiomers showed >95% ee.

(R)-8-((2,6-Difluoro-4-(1-((3-methylpyridin-4-yl)methyl)-5-oxopyrrolidin-3-yl)phenyl)-λ$^3$-iodanylidene)-6,10-dioxaspiro[4.5]decane-7,9-dione ((R)-59)

Compound (R)-59 was prepared in procedures similar to those described above for 31. Yield: 21%.

Synthesis of Compounds 4, 5, 6, 11, 12, 13, 18, and 24

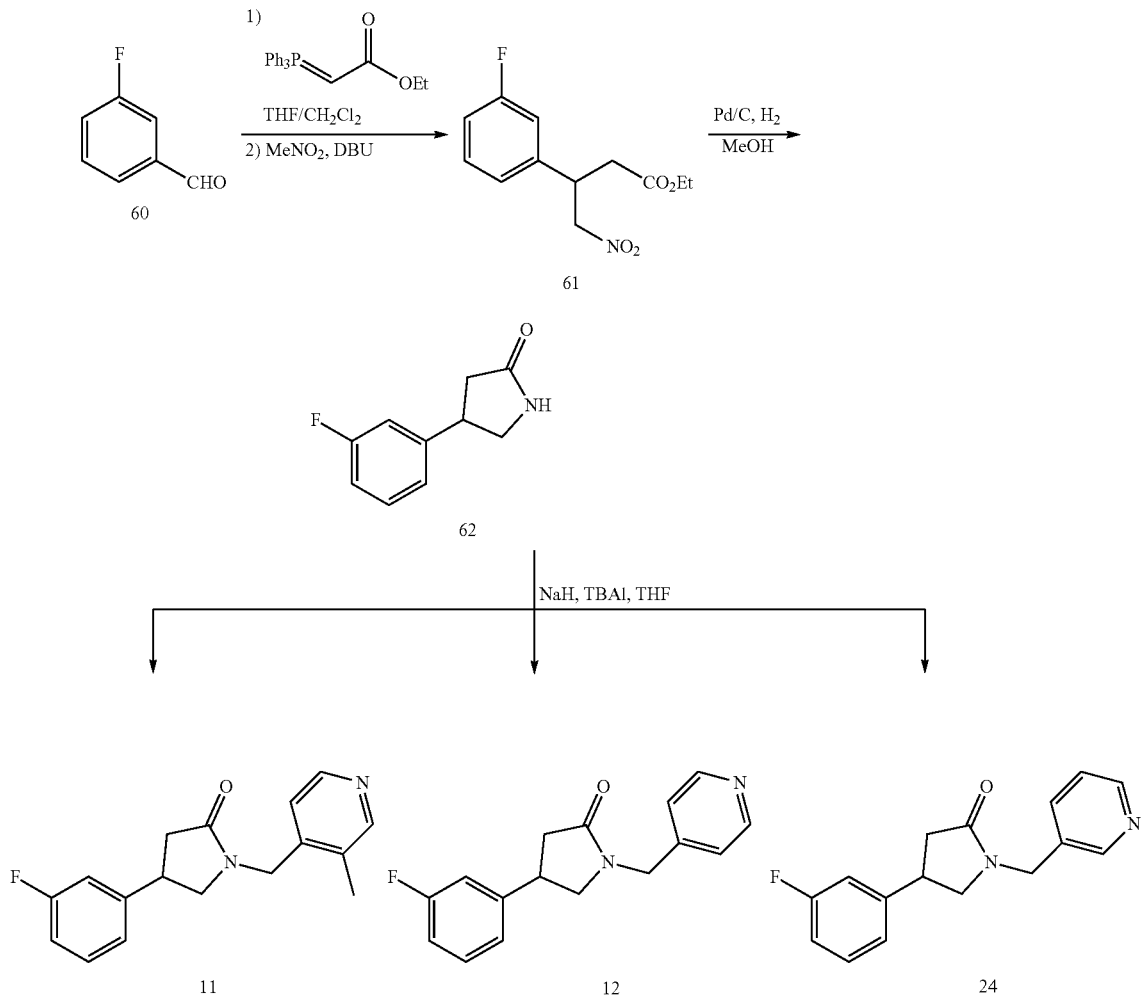

Scheme 5. Synthesis of compounds 11, 12, and 24.

Ethyl 3-(3-fluorophenyl)-4-nitrobutanoate (61)

Compound 61 was prepared in procedures similar to those described above for 29. Yield: 77%. $^1$H NMR (CDCl$_3$, 400 MHz): δ 7.39-7.21 (m, 1H), 7.11-6.90 (m, 3H), 4.73 (dd, J=12.8, 6.7 Hz, 1H), 4.63 (dd, J=12.7, 8.2 Hz, 1H), 4.20-4.04 (m, 2H), 4.04-3.83 (m, 1H), 2.74 (dd, J=7.4, 2.4 Hz, 2H), 1.18 (t, J=7.1 Hz, 3H).

4-(3-Fluorophenyl)pyrrolidin-2-one (62)

A solution of 61 (0.56 g, 2.2 mmol) in methanol (5 mL) was degassed with argon for 5 min, Pd/C (10%, 0.36 g) was added, and the suspension stirred under an atmosphere of hydrogen at ambient temperature for 12 h. The reaction mixture was filtered through a layer of Celite and the filtrate concentrated in vacuo. The crude product was purified on a silica gel column eluting with 0-10% EtOH/EtOAc to provide 62 as a colorless oil (390 mg, 99%). $^1$H NMR (CDCl$_3$, 400 MHz): δ 7.29 (q, J=7.34, 6.89 Hz, 1H), 7.01 (d, J=7.61 Hz, 1H), 6.94 (t, J=8.18 Hz, 2H), 3.78 (t, J=8.75 Hz, 1H), 3.68 (p, J=8.15 Hz, 1H), 3.39 (t, J=8.54 Hz, 1H), 2.73 (dd, J=16.9, 8.86 Hz, 1H), 2.46 (dd, J=16.9, 8.58 Hz, 1H).

General Procedure for the Synthesis of Compounds 11, 12, and 24

To a solution of 62 (55 mg, 0.31 mmol) in anhydrous THF (2.0 mL) under argon and cooled at 0° C. was added sodium hydride (61 mg, 1.54 mmol). The corresponding chloromethyl pyridine (0.37 mmol) was then added and the mixture stirred for 12 h at 50° C. The reaction was quenched with saturated NaHCO$_3$ solution (6 mL) and extracted with EtOAc (3 mL×3). The organic extracts were combined, dried over Na$_2$SO$_4$ and concentrated in vacuo. The crude product was purified on a silica gel column eluting with 0-10% EtOH/EtOAc to afford the product.

4-(3-Fluorophenyl)-1-((3-methylpyridin-4-yl)methyl)pyrrolidin-2-one (11)

$^1$H NMR (CDCl$_3$, 400 MHz): δ 8.40 (s, 2H), 7.29 (q, J=7.40, 7.40 Hz, 1H), 7.03 (d, J=4.80 Hz, 1H), 6.95 (d, J=7.98 Hz, 2H), 6.88 (d, J=10.0 Hz, 1H), 4.60 (d, J=15.6 Hz, 1H), 4.40 (d, J=15.5 Hz, 1H), 3.59 (m, 2H), 3.26 (m, 1H), 2.90 (dd, J=17.1, 8.19 Hz, 1H), 2.62 (dd, J=17.1, 7.55 Hz, 1H), 2.29 (s, 3H). $^{13}$C NMR (CDCl$_3$, 100 MHz): δ 173.57, 151.05 (2C), 147.77 (2C), 142.96, 131.65, 130.48 (split 2 peaks), 122.32 (split 2 peaks), 122.29, 114.15 (split 2 peaks), 113.71 (split 2 peaks), 53.76, 43.54, 38.21, 36.94, 15.93. $^{19}$F NMR (CDCl$_3$, 376 MHz): δ −112.17. HRMS: calculated for C$_{17}$H$_{17}$FN$_2$O [M+H]$^+$ 285.1398; found, 285.1423.

Chiral Separation and Analysis of the Enantiomers

The separation was conducted on a ChiralPak IA column, and the first compound eluting out from the column was the inactive enantiomer ((S)-11), while the second compound was the active enantiomer ((R)-11). The enantiomeric excess (ee.) was checked on an analytical ChiralPak IA column (4.6×250 mm). Mobile phase: 30/70 EtOH/hexane with 0.1% TEA, flow rate: 1.0 mL/min. Both enantiomers showed >99% ee.

4-(3-Fluorophenyl)-1-(pyridin-4-ylmethyl)pyrrolidin-2-one (12)

$^1$H NMR (CDCl$_3$, 400 MHz): δ 8.56 (s, 2H), 7.27 (t, J=7.87 Hz, 1H), 7.16 (d, J=4.50 Hz, 2H), 6.94 (d, J=7.98 Hz, 2H), 6.86 (d, J=9.98 Hz, 1H), 4.56 (d, J=15.3 Hz, 1H), 4.44 (d, J=15.4 Hz, 1H), 3.60 (m, 2H), 3.27 (t, J=6.21 Hz, 1H), 2.89 (dd, J=17.2, 8.37 Hz, 1H), 2.60 (dd, J=17.0, 7.95 Hz, 1H).

Chiral Separation and Analysis of the Enantiomers

The separation was conducted on a ChiralPak IF column, and the first compound eluting out from the column was the inactive enantiomer ((S)-12), while the second compound was the active enantiomer ((R)-12). The enantiomeric excess (ee.) was checked on an analytical ChiralPak IF column (4.6×250 mm). Mobile phase: 30/70 EtOH/hexane with 0.1% TEA, flow rate: 1.0 mL/min. Both enantiomers showed >98% ee.

4-(3-Fluorophenyl)-1-(pyridin-3-ylmethyl)pyrrolidin-2-one (24)

$^1$H NMR (CDCl$_3$, 400 MHz): δ 8.55 (d, J=4.62 Hz, 1H), 8.51 (s, 1H), 7.62 (d, J=7.68 Hz, 1H), 7.28 (m, 2H), 6.92 (d, J=5.65 Hz, 2H), 6.84 (d, J=9.75 Hz, 1H), 4.56 (d, J=15.95 Hz, 1H), 4.47 (d, J=15.91 Hz, 1H), 3.63 (t, J=8.74 Hz, 1H), 3.55 (p, J=7.42 Hz, 1H), 3.26 (t, J=7.96 Hz, 1H), 2.87 (dd, J=16.9, 8.78 Hz, 1H), 2.58 (dd, J=16.7, 8.06 Hz, 1H).

Scheme 6. Synthesis of compounds 6, 13, and 18.

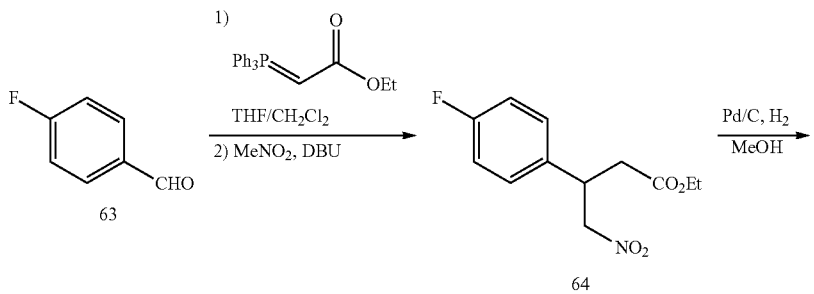

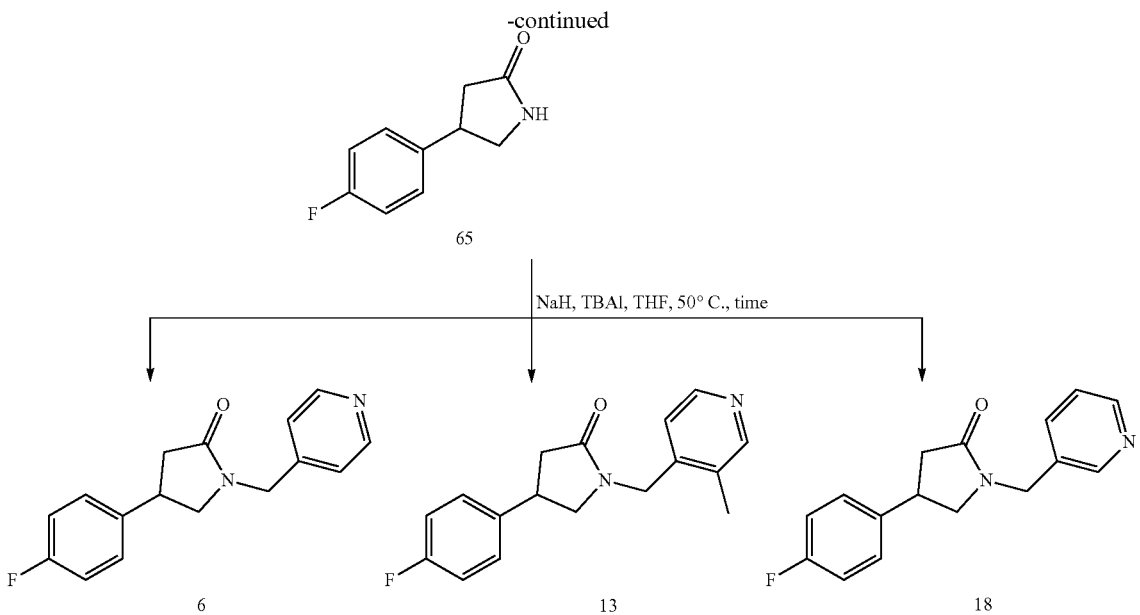

Ethyl 3-(4-fluorophenyl)-4-nitrobutanoate (64)

Compound 64 was prepared in procedures similar to those described above for 29. Yield: 77%. $^1$H NMR (CDCl$_3$, 400 MHz): δ 7.23-7.16 (m, 2H), 7.03 (t, J=8.6 Hz, 2H), 4.78-4.67 (m, 1H), 4.61 (dd, J=12.6, 8.2 Hz, 1H), 4.08 (q, J=7.2 Hz, 2H), 4.05-3.85 (m, 1H), 2.74 (dd, J=7.5, 5.6 Hz, 2H), 1.18 (t, J=7.1 Hz, 3H).

4-(4-Fluorophenyl)pyrrolidin-2-one (65)

Compound 65 was prepared in procedures similar to those described above for 62. Yield: 36%. $^1$H NMR (CDCl$_3$, 400 MHz): δ 7.20 (t, J=7.64 Hz, 2H), 7.02 (t, J=8.58 Hz, 2H), 5.80 (s, 1H), 3.76 (t, J=8.69 Hz, 1H), 3.67 (p, J=8.19 Hz, 1H), 3.36 (t, J=8.60 Hz, 1H), 2.72 (dd, J=16.9, 8.81 Hz, 1H), 2.44 (dd, J=16.91, 8.75 Hz, 1H).

4-(4-Fluorophenyl)-1-(pyridin-4-ylmethyl)pyrrolidin-2-one (6)

Compound 6 was prepared in procedures similar to those described above for 11. $^1$H NMR (CDCl$_3$, 400 MHz): δ 8.57 (d, J=5.61 Hz, 2H), 7.16 (d, J=5.77 Hz, 2H), 7.13 (d, J=8.62 Hz, 2H), 6.99 (t, J=8.59 Hz, 2H), 4.56 (d, J=15.35 Hz, 1H), 4.43 (d, J=15.36 Hz, 1H), 3.63 (q, J=8.39 Hz, 1H), 3.56 (p, J=8.28 Hz, 1H), 3.25 (dd, J=8.90, 6.59 Hz, 1H), 2.89 (dd, J=16.98, 8.66 Hz, 1H), 2.59 (dd, J=17.04, 8.16 Hz, 1H).

4-(4-Fluorophenyl)-1-((3-methylpyridin-4-yl)methyl)pyrrolidin-2-one (13)

Compound 13 was prepared in procedures similar to those described above for 11. $^1$H NMR (CDCl$_3$, 400 MHz): δ 8.48 (s, 2H), 7.14 (t, J=8.43 Hz, 2H), 7.06 (s, 1H), 7.00 (t, J=8.57 Hz, 2H), 4.60 (d, J=15.49 Hz, 1H), 4.38 (d, J=15.54 Hz, 1H), 3.58 (m, 2H), 3.23 (m, 1H), 2.89 (dd, J=17.00, 8.47 Hz, 1H), 2.60 (dd, J=16.93, 7.99 Hz, 1H), 2.30 (s, 3H).

4-(4-Fluorophenyl)-1-(pyridin-3-ylmethyl)pyrrolidin-2-one (18)

Compound 18 was prepared in procedures similar to those described above for 11. $^1$H NMR (CDCl$_3$, 400 MHz): δ 8.54 (d, J=4.52 Hz, 1H), 8.51 (s, 1H), 7.61 (d, J=7.79 Hz, 1H), 7.27 (dd, J=7.79, 4.87 Hz, 1H), 7.11 (t, J=8.54 Hz, 2H), 6.98 (t, J=8.61 Hz, 2H), 4.56 (d, J=14.9 Hz, 1H), 4.46 (d, J=14.9 Hz, 1H), 3.62 (q, J=8.45 Hz, 1H), 3.53 (p, J=8.36 Hz, 1H), 3.23 (dd, J=9.31, 6.89 Hz, 1H), 2.86 (dd, J=16.96, 8.87 Hz, 1H), 2.56 (dd, J=16.93, 8.31 Hz, 1H).

Scheme 7. Synthesis of compounds 4 and 5.

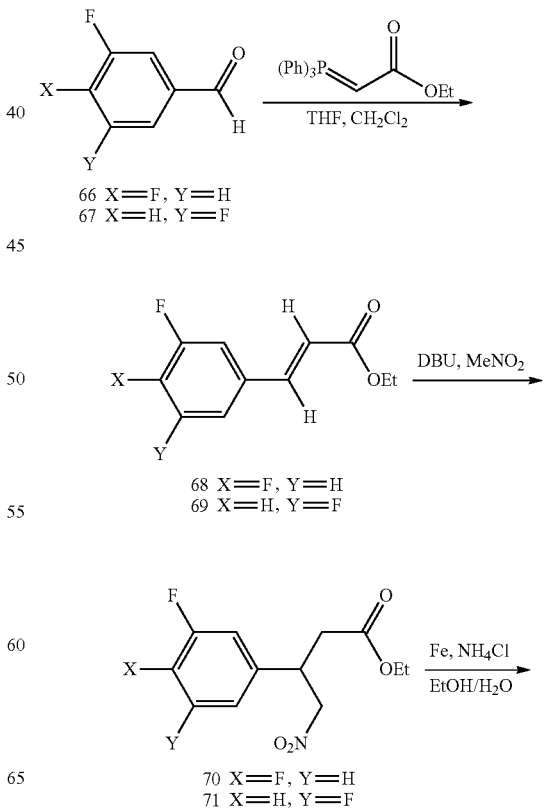

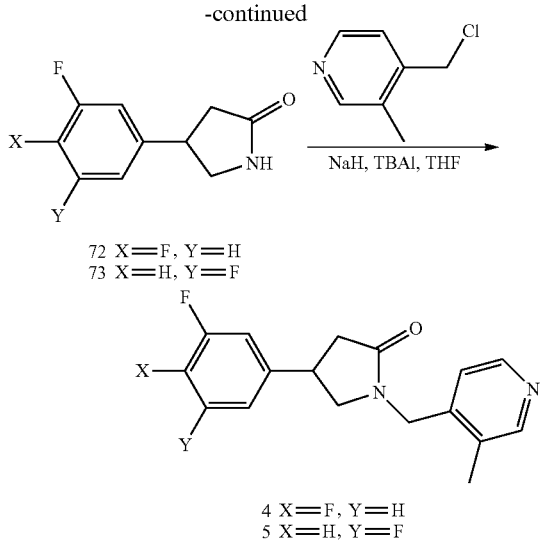

Ethyl (E)-3-(3,4-difluorophenyl)acrylate (68)

Compound 68 was prepared in procedures similar to those described above for 41. Yield: Quantitative. ¹H NMR (CDCl₃, 400 MHz): δ 7.55 (d, J=16.02 Hz, 1H), 7.32 (t, J=9.32 Hz, 1H), 7.23 (d, J=9.62 Hz, 1H), 7.15 (q, J=8.61 Hz, 1H), 6.32 (d, J=15.98 Hz, 1H), 4.24 (q, J=7.10 Hz, 2H), 1.31 (t, J=7.11 Hz, 3H).

Ethyl (E)-3-(3,5-difluorophenyl)acrylate (69)

Compound 69 was prepared in procedures similar to those described above for 41. Yield: Quantitative. ¹H NMR (CDCl₃, 400 MHz): δ 7.56 (d, J=15.97 Hz, 1H), 7.03 (d, J=6.26 Hz, 2H), 6.83 (t, J=8.70 Hz, 1H), 6.42 (d, J=15.97 Hz, 1H), 4.27 (q, J=7.13 Hz, 2H), 1.34 (t, J=7.13 Hz, 3H).

Ethyl 3-(3,4-difluorophenyl)-4-nitrobutanoate (70)

Compound 70 was prepared in procedures similar to those described above for 43. ¹H NMR (CDCl₃, 400 MHz): δ 7.12 (q, J=9.00 Hz, 1H), 7.05 (t, J=9.60 Hz, 1H), 6.96 (d, J=7.77 Hz, 1H), 4.70 (dd, J=12.72, 8.56 Hz, 1H), 4.58 (dd, J=12.63, 8.40 Hz, 1H), 4.08 (q, J=7.15 Hz, 2H), 3.94 (p, J=7.40 Hz, 1H), 2.70 (m, 2H), 1.18 (t, J=7.11 Hz, 3H).

Ethyl 3-(3,5-difluorophenyl)-4-nitrobutanoate (71)

Compound 71 was prepared in procedures similar to those described above for 43. Yield: 80%. NMR (CDCl₃, 400 MHz): δ 6.78 (d, J=7.56 Hz, 2H), 6.73 (m, 1H), 4.72 (dd, J=12.90, 6.53 Hz, 1H), 4.61 (dd, J=12.85, 8.29 Hz, 1H), 4.11 (q, J=7.10 Hz, 2H), 3.98 (p, J=7.31 Hz, 1H), 2.73 (m, 2H), 1.20 (t, J=7.13 Hz, 3H).

4-(3,4-Difluoro-4-iodophenyl)pyrrolidin-2-one (72)

Compound 72 was prepared in procedures similar to those described above for 45. Yield: 80%. ¹H NMR (CDCl₃, 400 MHz): δ 7.12 (q, J=8.63 Hz, 1H), 7.05 (t, J=7.67 Hz, 1H), 6.95 (m, 1H), 6.02 (s, 1H), 3.77 (t, J=8.77 Hz, 1H), 3.65 (p, J=8.26 Hz, 1H), 3.36 (dd, J=9.28, 7.12 Hz, 1H), 2.72 (dd, J=16.88, 8.89 Hz, 1H), 2.41 (dd, J=16.88, 8.46 Hz, 1H).

4-(3,5-Difluorophenyl)pyrrolidin-2-one (73)

Compound 73 was prepared in procedures similar to those described above for 45. Yield: 72% ¹H NMR (CDCl₃, 400 MHz): δ 6.78 (d, J=6.60 Hz, 2H), 6.72 (t, J=8.83 Hz, 1H), 5.79 (s, 1H), 3.79 (t, J=8.74 Hz, 1H), 3.68 (p, J=8.21 Hz, 1H), 3.39 (m, 1H), 2.75 (dd, J=16.88, 8.91 Hz, 1H), 2.44 (dd, J=16.90, 8.37 Hz, 1H).

4-(3,4-Difluoro-4-iodophenyl)-1-((3-methylpyridin-4-yl)methyl)pyrrolidin-2-one (4)

Compound 4 was prepared in procedures similar to those described above for 32. Yield: 75%. ¹H NMR (CDCl₃, 400 MHz): δ 8.40 (s, 2H), 7.09 (q, J=8.40 Hz, 1H), 7.01 (d, J=5.11 Hz, 1H), 6.97 (m, 1H), 6.89 (m, 1H), 4.60 (d, J=15.46 Hz, 1H), 4.38 (d, J=15.48 Hz, 1H), 3.60 (m, 2H), 3.21 (m, 1H), 2.88 (dd, J=16.90, 8.51 Hz, 1H), 2.56 (dd, J=17.00, 7.98 Hz, 1H), 2.29 (s, 3H); ¹³C NMR (CDCl₃, 150 MHz): δ 173.25, 151.03 (2C), 147.74 (2C), 142.88, 138.78, 131.57, 122.66, 122.24, 117.59 (split 2 peaks), 113.71 (split 2 peaks), 53.72, 43.47, 38.26, 36.49, 15.84. ¹⁹F NMR (CDCl₃, 376 MHz): δ −136.77, −139.80.

Chiral Separation and Analysis of the Enantiomers

The separation was conducted on a ChiralPak IA-3 column, and the first compound eluting out from the column was the inactive enantiomer ((S)-4), while the second compound was the active enantiomer ((R)-4). The enantiomeric excess (ee.) was checked on an analytical ChiralPak IA-3 column (4.6×250 mm). Mobile phase: 20/80 EtOH/hexane with 0.1% TEA, flow rate: 1.0 mL/min. Both enantiomers showed >98% ee.

4-(3,5-Difluorophenyl)-1-((3-methylpyridin-4-yl)methyl)pyrrolidin-2-one (5)

Compound 5 was prepared in procedures similar to those described above for 32. ¹H NMR (CDCl₃, 400 MHz): δ 8.41 (s, 2H), 7.02 (d, J=4.29 Hz, 1H), 6.69 (m, 3H overlap), 4.61 (d, J=15.51 Hz, 1H), 4.40 (d, J=15.38 Hz, 1H), 3.59 (p, J=8.36 Hz, 2H), 3.23 (m, 1H), 2.90 (dd, J=17.06, 8.49 Hz, 1H), 2.58 (dd, J=17.18, 7.44 Hz, 1H), 2.30 (s, 3H); 19F NMR (CDCl₃, 376 MHz): δ −108.64.

Chiral Separation and Analysis of the Enantiomers

The separation was conducted on a ChiralPak IA column, and the first compound eluting out from the column was the inactive enantiomer ((S)-5), while the second compound was the active enantiomer ((R)-5). The enantiomeric excess (ee.) was checked on an analytical ChiralPak IA column (10 μm, 4.6×250 mm). Mobile phase: 30/70 EtOH/hexane with 0.1% TEA, flow rate: 1.0 mL/min. Both enantiomers showed >99% ee.

Radiosynthesis of $^{18}$F-3, $^{18}$F-4, $^{18}$F-5, $^{18}$F-11, and $^{18}$F-12
Scheme 8. Radiosynthesis of $^{18}$F-3, $^{18}$F-4, $^{18}$F-5, $^{18}$F-11, and $^{18}$F-12.
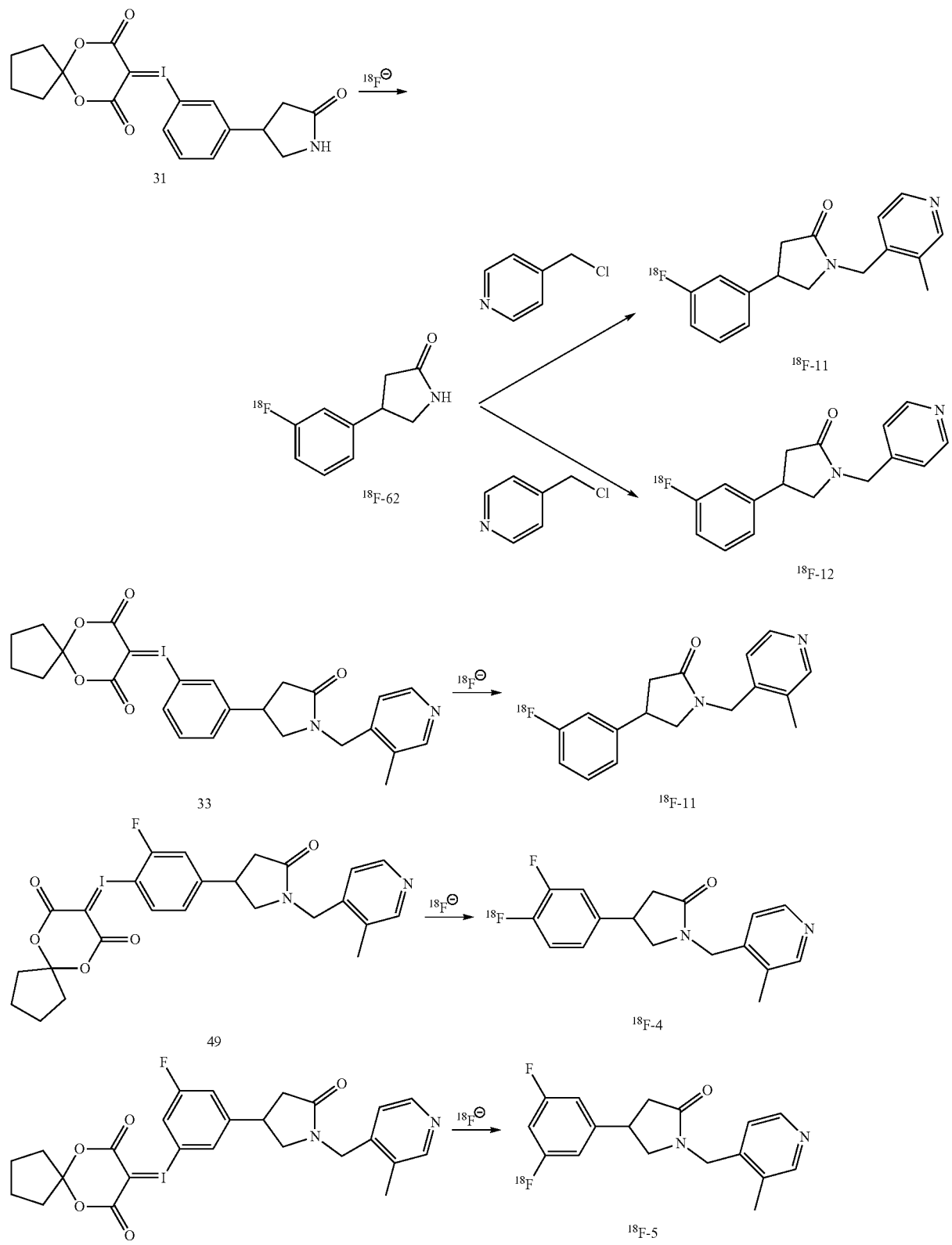

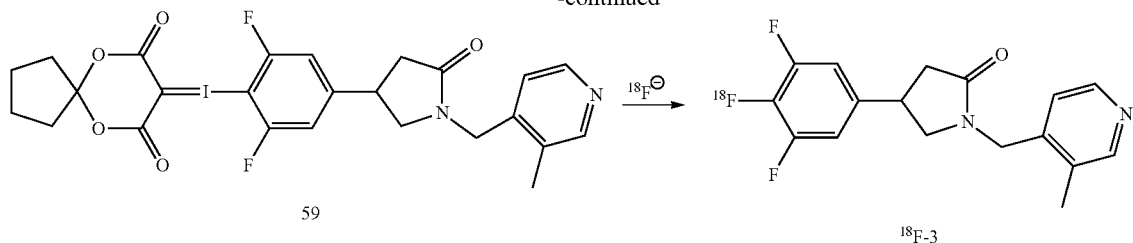

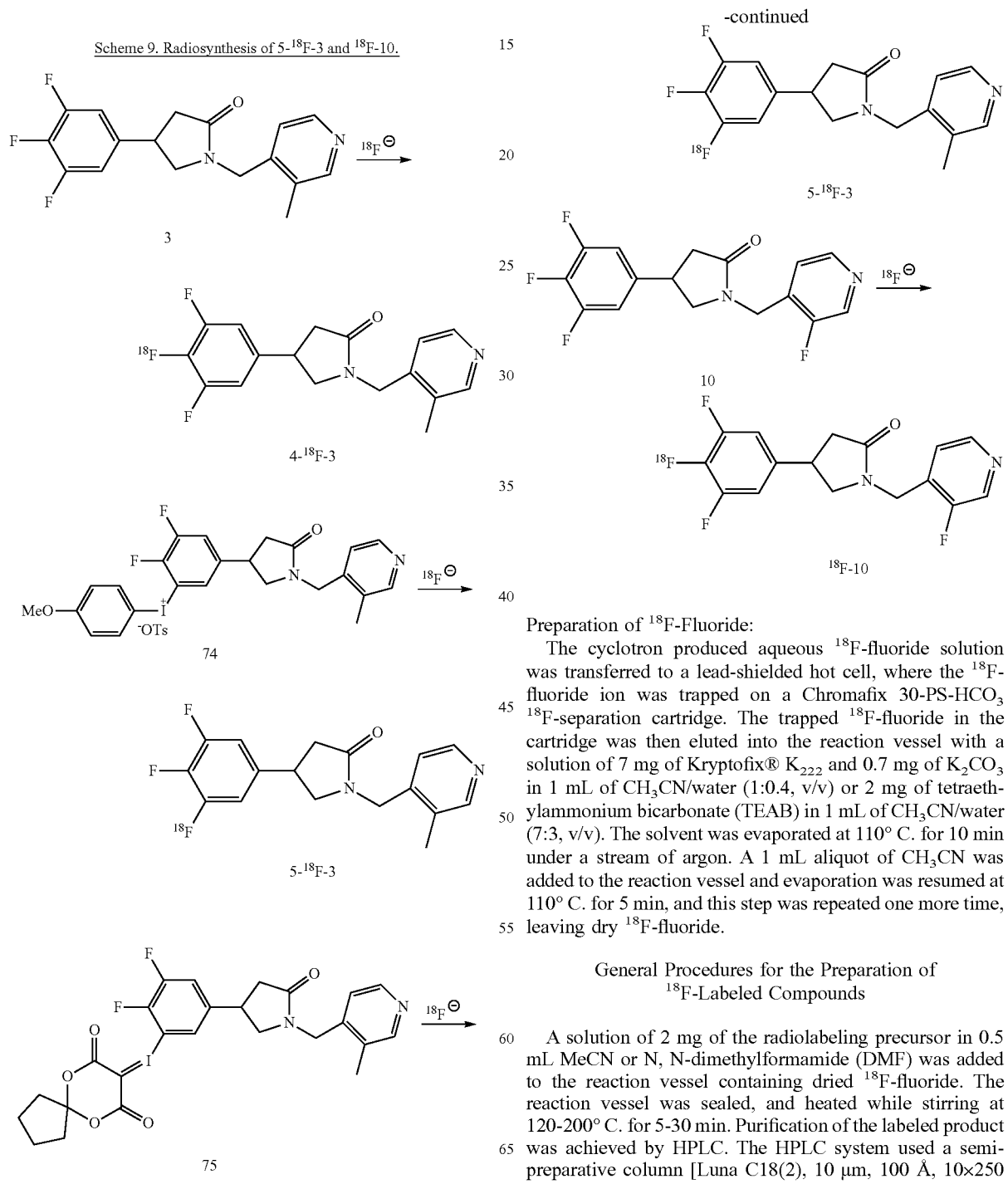

Preparation of $^{18}$F-Fluoride:

The cyclotron produced aqueous $^{18}$F-fluoride solution was transferred to a lead-shielded hot cell, where the $^{18}$F-fluoride ion was trapped on a Chromafix 30-PS-HCO$_3$ $^{18}$F-separation cartridge. The trapped $^{18}$F-fluoride in the cartridge was then eluted into the reaction vessel with a solution of 7 mg of Kryptofix® K$_{222}$ and 0.7 mg of K$_2$CO$_3$ in 1 mL of CH$_3$CN/water (1:0.4, v/v) or 2 mg of tetraethylammonium bicarbonate (TEAB) in 1 mL of CH$_3$CN/water (7:3, v/v). The solvent was evaporated at 110° C. for 10 min under a stream of argon. A 1 mL aliquot of CH$_3$CN was added to the reaction vessel and evaporation was resumed at 110° C. for 5 min, and this step was repeated one more time, leaving dry $^{18}$F-fluoride.

General Procedures for the Preparation of $^{18}$F-Labeled Compounds

A solution of 2 mg of the radiolabeling precursor in 0.5 mL MeCN or N, N-dimethylformamide (DMF) was added to the reaction vessel containing dried $^{18}$F-fluoride. The reaction vessel was sealed, and heated while stirring at 120-200° C. for 5-30 min. Purification of the labeled product was achieved by HPLC. The HPLC system used a semi-preparative column [Luna C18(2), 10 μm, 100 Å, 10×250 mm] from Phenomenex, Torrance, Calif. or its equivalent.

Alternatively, the enantiopure product was purified by a semi-preparative chiral column (ChiralCel, OD-H, SFC, 10 µm, 10×250 mm). The column was eluted under isocratic conditions at a flow rate of 5 mL/min with a mixture of MeCN and 0.1 M aqueous ammonium formate with 0.5% acetic acid (v/v, pH 4.2). The eluent was monitored by a UV detector and a radioactivity detector. The fraction containing the radiolabeled product was collected, diluted with deionized (DI) water (50 mL), and passed through a C18 SepPak. The SepPak was washed with DI water (10 mL), and dried with air. The $^{18}$F-labeled product was eluted off the SepPak with ethanol (1 mL), followed by USP saline (3 mL). The resulting solution was then passed through a sterile membrane filter (0.2 µm) for terminal sterilization and collected in a sterile vial pre-charged with 7 mL of saline (USP) to afford a formulated solution ready for dispensing and intravenous administration.

Example 2: Radioligand Competition Binding Assays

Binding affinities of the compounds to SV2A were determined in radioligand competition binding assays using rat brain homogenates and the radioligand $^{11}$C-3 with known affinity ($K_D$=3.9 nM), or with (R)-$^{18}$F-11.

One Sprague Dawley rat was euthanized with carbon dioxide inhalation. The brain was harvested, rapidly frozen on dry ice and then stored at −80° C. The whole brain homogenates were obtained following published procedures. The final homogenate was suspended in 20 mM Tris-HCl buffer (pH 7.4) containing 250 mM of sucrose at a wet tissue concentration of 100 mg/mL and stored at −80° C. until use.

For competition binding experiments, 0.5 mg of the rat brain homogenates in 800 µL of binding buffer (2 mM $MgCl_2$ in 50 mM Tris*HCl, pH=7.4) were incubated on a thermoshaker at 37° C. for 30 min with 100 µL (R)-$^{11}$C-3 or (R)-$^{18}$F-11 and 100 µL of the compound over a range of concentrations (from 0.1 to 100 nM). Nonspecific binding was defined as the residual binding observed in the presence of 1 mM levetiracetam (100 µL). At completion of the incubation period, the membrane-bound radioligand was recovered using rapid filtration through GF/B glass fiber filters (13 mm GD/X, Whatman Inc.) which were pre-soaked for at least 30 min in 0.5% polyethyleneimine (PEI). The membranes were washed twice with 1 mL of ice-cooled binding buffer. The binding mixtures, filters and filtrates were counted using cross-calibrated gamma counters (1480 & 2480 WIZARD; Perkin-Elmer). Values of $IC_{50}$ were calculated using the GRAPHPAD PRISM™ software and converted to inhibition constants ($K_i$) by the Cheng-Prusoff equation.

Assay compounds displayed moderate to high binding affinity to SV2A protein. Values of $IC_{50}$ and K for some example compounds are listed in Table 1.

TABLE 1

Values of $IC_{50}$ and $K_i$ obtained from radioligand competition binding assays

| Compound | $IC_{50}$ (nM) | $K_i$ (nM) |
|---|---|---|
| (R)-3 | 1.621 | 0.27 |
| (S)-3 | 75.56 | 12.5 |
| (R)-4 | 12.58 | 2.08 |
| (S)-4 | 56.99 | 9.43 |
| (R)-5 | 3.524 | 0.58 |

TABLE 1-continued

Values of $IC_{50}$ and $K_i$ obtained from radioligand competition binding assays

| Compound | $IC_{50}$ (nM) | $K_i$ (nM) |
|---|---|---|
| (S)-5 | 698.1 | 115.46 |
| (R)-11 | 26.85 | 4.44 |
| (S)-11 | 109.2 | 18.2 |
| (R)-12 | 26.8 | 4.43 |
| (S)-12 | 28.2 | 4.66 |

Example 3: Evaluation of Radioligands by PET Imaging Studies in Rhesus Monkeys Experiments were performed in rhesus monkeys (*Macaca mulatta*). Rhesus monkeys were sedated using intramuscular (i.m.) injection of ketamine and glycopyrrolate approximately 2 hours before the PET scan and anesthesia was maintained with isoflurane (1.5%-2.5%) for the duration of the experiments. Baseline PET scans were obtained after intravenous (i.v.) injection of $^{11}$C-3, $^{18}$F-3, $^{18}$F-4, $^{18}$F-5, $^{18}$F-10, $^{18}$F-11, or $^{18}$F-12. Specific binding of the radioligands to SV2A was evaluated in displacement experiments by administering levetiracetam (30 mg/kg, 5 min i.v. infusion) at 60 or 90 min post injection of $^{18}$F-labeled radiotracer, and/or in blocking experiments with administration of levetiracetam (30 mg/kg, i.v.) or UCB-J (the (R)-enantiomer of compound 3, (R)-3, 150 µg/kg, i.v.) 10 min before injection of the radiotracer.

Arterial blood samples were collected during the PET scans to calculate the plasma input function and to determine the unmetabolized parent fraction using the automatic column-switching HPLC system. Plasma free fraction (fp) was measured in triplicate using the ultrafiltration method.

PET scans of the brain were acquired using the FOCUS 220 PET scanner (Siemens Preclinical Solutions) with a reconstructed image resolution of approximately 1.5 mm. After a transmission scan, the radioligand was injected i.v. as a 3 min slow bolus by an infusion pump (PHD 22/2000; Harvard Apparatus). List-mode data were acquired for 120-180 min and binned into sinograms with an applicable number of frames. Scan data were reconstructed with a Fourier rebinning/filtered backprojection algorithm with corrections for attenuation, scanner normalization, radiation scatter, and randoms. Regions of interest were manually delineated on a single representative anatomic rhesus monkey MR image registered to a template image. The regions used in this study were amygdala, brain stem, caudate, centrum semiovale, cerebellum, cingulate cortex, frontal cortex, globus pallidus, insular cortex, nucleus accumbens, occipital cortex, pons, putamen, temporal cortex, and thalamus. Registration parameters were obtained to apply the regions of interest to individual PET scans, and regional time-activity curves were generated. Regional time-activity curves of the brain were analyzed with the 1-tissue-(1T) compartment model. Fit quality was compared with the 2-tissue model and the multilinear analysis method to calculate $V_T$.

Typical injected radioactivity amount was 0.5-5 mCi per injection, with typical injected mass amount of 1-10 µg.

The radiotracers showed similar rates of metabolism in rhesus monkeys. Radiometabolites were more polar (shorter retention time on HPLC) than the parent radiotracer. The fp values were high, at 42±6% for $^{18}$F-3 (n=4), 41% for $^{18}$F-4, 42±3% for $^{18}$F-5 (n=2), 52% for $^{18}$F-10, 42±2% for $^{18}$F-11 (n=4), 61% for $^{18}$F-12, and 44±1% for $^{11}$C-3 (n=5).

After injection of the radioligands, the PET-measured distribution of radioactivity was higher in the gray matter and lowest in the white matter centrum semiovale brain region. Regional time-activity curves for selected radiotracers are presented in FIGS. 1 & 2. All radioligands displayed high uptake in the brain (peak SUV>5). The SUV peak in gray matter regions was achieved within 10 min for $^{18}$F-4, $^{18}$F-10, $^{18}$F-11 and $^{18}$F-12, but was slower for $^{18}$F-3, $^{18}$F-5 and $^{11}$C-3 (FIGS. 1 & 2).

For all radiotracers, the 1T model produced suitable fits and reliable distribution volume ($V_T$) values. Multilinear analysis method 1 produced good fits with small differences in $V_T$ values from 1T. Overall, the 2-tissue compartment model produced comparable $V_T$ estimates, but with higher standard error than the 1T model. Thus, the 1T model was the method chosen for quantification of $V_T$ values. The regional $V_T$ values are shown in Table 2. Regional $BP_{ND}$ values were estimated using the centrum semiovale as the reference region and are provided in Table 3. Reversible and specific binding to SV2A was examined for $^{18}$F-3, $^{18}$F-4, $^{18}$F-5, $^{18}$F-11, and $^{18}$F-12 in displacement studies with levetiracetam, where levetiracetam was i.v. infused 60 or 90 min post injection of the radiotracer and reduced the binding of these tracers to a significant extent (FIG. 3). Specific binding to SV2A was further examined for $^{11}$C-3, $^{18}$F-3, and $^{18}$F-11 in blocking studies, where levetiracetam or UCB-J ((R)-3) was i.v. infused before injection of the radiotracers. Uptake of radiotracers was all reduced to background levels, indicating blocking of specific binding by levetiracetam and UCB-J (FIG. 4). Thus, the SV2A binding specificity of the examined radiotracers was demonstrated.

TABLE 2

Distribution volumes ($V_T$)* in monkey brain regions calculated with 1T model.

| | Radiotracer | | | | | | |
|---|---|---|---|---|---|---|---|
| | $^{18}$F-4 n = 1 | $^{18}$F-5 n = 2 | $^{18}$F-10 n = 1 | $^{18}$F-11 n = 3 | $^{18}$F-12 n = 1 | $^{18}$F-3 n = 3 | $^{11}$C-3 n = 5 |
| Cingulate cortex | 18.77 | 45.0 ± 9.2 | 16.0 | 18.2 ± 2.2 | 8.5 | 47.9 ± 7.9 | 55.6 ± 9.9 |
| Frontal cortex | 18.30 | 43.0 ± 8.1 | 14.7 | 17.4 ± 2.2 | 8.0 | 46.2 ± 6.1 | 55.4 ± 8.2 |
| Insular cortex | 17.77 | 42.3 ± 9.1 | 14.9 | 16.8 ± 2.6 | 7.3 | 45.7 ± 5.9 | 54.6 ± 6.7 |
| Nucleus accumbens | 18.08 | 41.9 ± 7.8 | 14.4 | 16.4 ± 2.9 | 7.6 | 42.5 ± 5.5 | 53.9 ± 9.2 |
| Occipital cortex | 17.19 | 39.3 ± 10.7 | 15.5 | 15.7 ± 2.7 | 6.6 | 41.3 ± 6.6 | 52.9 ± 7.0 |
| Temporal cortex | 16.74 | 37.9 ± 9.4 | 14.0 | 14.7 ± 2.5 | 6.8 | 39.2 ± 5.6 | 50.5 ± 6.9 |
| Putamen | 14.90 | 32.8 ± 5.2 | 14.0 | 13.6 ± 2.3 | 6.5 | 34.3 ± 5.3 | 45.2 ± 3.0 |
| Caudate nucleus | 14.19 | 31.9 ± 4.8 | 13.8 | 13.2 ± 2.6 | 6.1 | 33.1 ± 3.4 | 44.8 ± 4.6 |
| Thalamus | 13.78 | 32.7 ± 1.9 | 12.0 | 13.2 ± 2.1 | 5.0 | 32.3 ± 7.3 | 40.3 ± 6.4 |
| Cerebellum | 12.84 | 26.1 ± 6.5 | 12.3 | 10.8 ± 2.6 | 4.4 | 27.6 ± 3.8 | 36.0 ± 5.2 |
| Hippocampus | 12.25 | 27.3 ± 4.0 | 11.3 | 10.7 ± 2.8 | 5.0 | 26.9 ± 1.7 | 34.4 ± 2.8 |
| Globus pallidus | 10.17 | 19.3 ± 2.4 | 11.5 | 8.8 ± 1.8 | 4.5 | 24.0 ± 6.3 | 27.9 ± 3.0 |
| Amygdala | 8.62 | 20.5 ± 6.0 | 9.8 | 8.7 ± 2.4 | 3.6 | 19.2 ± 4.3 | 24.4 ± 2.0 |
| Brainstem | 9.09 | 15.0 ± 4.0 | 10.2 | 6.6 ± 2.9 | 3.3 | 17.3 ± 2.1 | 23.5 ± 2.8 |
| Pons | 9.00 | 14.9 ± 4.1 | 10.5 | 6.4 ± 3.5 | 3.2 | 17.0 ± 2.6 | 23.4 ± 3.2 |
| Centrum semiovale | 5.21 | 8.3 ± 2.4 | 10.1 | 4.4 ± 1.5 | 3.5 | 9.5 ± 1.7 | 13.6 ± 2.8 |

*Data are single or multiple (n) measurements represented as single value or mean ± SD, respectively.
SD is standard deviation.

TABLE 2

Binding potential ($BP_{ND}$) values* in monkey brain regions calculated from the $V_T$ values using centrum semiovale as reference region.

| | Radiotracer | | | | | | |
|---|---|---|---|---|---|---|---|
| | $^{18}$F-4 n = 1 | $^{18}$F-5 n = 2 | $^{18}$F-10 n = 1 | $^{18}$F-11 n = 3 | $^{18}$F-12 n = 1 | $^{18}$F-3 n = 3 | $^{11}$C-3 n = 5 |
| Cingulate cortex | 2.60 | 4.49 ± 0.50 | 0.59 | 3.49 ± 1.52 | 1.45 | 4.04 ± 0.38 | 3.17 ± 0.84 |
| Frontal cortex | 2.51 | 4.26 ± 0.57 | 0.46 | 3.29 ± 1.40 | 1.28 | 3.90 ± 0.54 | 3.18 ± 0.91 |
| Insular cortex | 2.41 | 4.16 ± 0.42 | 0.48 | 3.00 ± 1.21 | 1.09 | 3.51 ± 0.56 | 3.12 ± 0.81 |
| Nucleus accumbens | 2.47 | 3.09 ± 2.04 | 0.43 | 3.12 ± 1.26 | 1.18 | 3.85 ± 0.57 | 3.04 ± 0.69 |
| Occipital cortex | 2.30 | 3.75 ± 0.11 | 0.53 | 2.90 ± 1.50 | 0.90 | 3.35 ± 0.27 | 2.97 ± 0.65 |
| Temporal cortex | 2.21 | 3.60 ± 0.22 | 0.39 | 2.63 ± 1.33 | 0.95 | 3.14 ± 0.41 | 2.79 ± 0.61 |
| Putamen | 1.86 | 3.03 ± 0.55 | 0.39 | 2.21 ± 0.89 | 0.86 | 2.62 ± 0.46 | 2.42 ± 0.63 |
| Caudate nucleus | 1.72 | 2.09 ± 1.37 | 0.37 | 2.29 ± 0.88 | 0.75 | 2.54 ± 0.60 | 2.40 ± 0.72 |
| Thalamus | 1.65 | 3.08 ± 0.96 | 0.19 | 2.18 ± 0.77 | 0.42 | 2.53 ± 1.18 | 2.03 ± 0.62 |
| Cerebellum | 0.55 | 2.16 ± 0.15 | 0.22 | 1.59 ± 0.76 | 0.25 | 1.88 ± 0.42 | 1.68 ± 0.31 |
| Hippocampus | 1.35 | 2.36 ± 0.51 | 0.12 | 1.58 ± 0.59 | 0.44 | 1.99 ± 0.75 | 1.59 ± 0.39 |
| Globus pallidus | 0.95 | 1.04 ± 0.09 | 0.14 | 1.13 ± 0.61 | 0.29 | 1.08 ± 0.59 | 1.10 ± 0.28 |
| Amygdala | 0.66 | 1.70 ± 1.51 | −0.03 | 1.05 ± 0.29 | 0.04 | 1.65 ± 1.04 | 0.85 ± 0.34 |
| Brainstem | 0.75 | 0.59 ± 0.57 | 0.01 | 0.53 ± 0.42 | −0.06 | 0.84 ± 0.28 | 0.76 ± 0.21 |
| Pons | 0.73 | 0.80 ± 0.03 | 0.04 | 0.46 ± 0.51 | −0.09 | 0.80 ± 0.26 | 0.75 ± 0.21 |

*Data are single or multiple (n) measurements represented as single value or mean ± SD, respectively.
SD is standard deviation.

Example 4: Validation of $^{11}$C-3 as a Synaptic Density Marker

Experiments were conducted in one olive baboon (*P. anubis*). The 7-year old female baboon (27 kg) was sedated using ketamine and glycopyrrolate-2.5 h before the start of the PET measurement and anesthesia was maintained using isoflurane (1.5-2.5%) for the duration of the experiment. PET images of the brain were acquired using a Siemens Biograph mCT system (Siemens Medical Solutions). Following a CT scan, 92 MBq of $^{11}$C-3 was injected intravenously as a 3-min slow bolus by an infusion pump (PHD 22/2000, Harvard Apparatus). List-mode data were acquired for 120 min and binned into sinograms with the following frame timing: 6×30 sec; 3×1 min; 2×2 min; and 22×5 min.

PET data were reconstructed with a TrueX+TOF algorithm with corrections for attenuation, normalization, scatter and randoms. Regions of interest (ROIs) were manually delineated on a single representative anatomical baboon magnetic resonance image (MRI) registered to a template image. The included ROIs were brainstem, caudate nucleus, centrum semiovale, cerebellum, cingulate cortex, frontal cortex, globus pallidus, insular cortex, pons, putamen, temporal cortex and thalamus. MRI-to-PET registration parameters were obtained to apply the ROIs to individual PET scans, and regional time-activity curves (TACs) were generated. $V_T$ values were estimated using a one-tissue (1T) compartment model with the metabolite-corrected input function.

Arterial blood samples were collected to determine the plasma input function, including measurement of the unmetabolized $^{11}$C-3 fraction. The free fraction of $^{11}$C-3 in plasma was determined in arterial blood samples taken immediately before $^{11}$C-3 injection.

After completion of the PET measurement, the baboon was euthanized using an i.v. bolus injection of pentobarbital (86 mg/kg) and phenytoin (11 mg/kg). The brain was rapidly harvested, placed on ice and sliced in coronal sections (~5-10 mm thick). The left hemisphere sections were placed in 4% paraformaldehyde in 0.1 M phosphate buffer, pH 7.4 and stored at 4° C. The right hemisphere sections were snap-frozen on dry ice and stored at 80° C. Later, tissue was dissected from 12 brain regions, matching those examined with PET, for Western blot analyses and homogenate binding studies.

Binding assays with baboon brain homogenate were performed in accordance with the above described methods for SV2A using $^{11}$C-3 or (R)-$^{18}$F-11. Frozen tissue of 12 brain regions was homogenized (10% w/v) using a Polytron in 20 mM Tris-HCl buffer (pH=7.4) containing 250 mM sucrose (buffer A). The homogenates were centrifuged at 24,000 g at 4° C. for 20 min and the pellets resuspended in fresh buffer A (1 mL). The membranes were then incubated at 37° C. for 15 min, followed by three cycles of washing using the same centrifugation protocol. The final pellets were resuspended in buffer A at a wet tissue concentration of 100 mg/mL and stored at −80° C. Protein concentrations were determined using the bicinchoninic acid method (BCA) using bovine serum albumin (BSA) as standard.

For binding experiments, membrane proteins [per assay: 70-300 μg in 700 μL of 2 mM MgCl$_2$ in 50 mM Tris-HCl, pH=7.4 (buffer B)] were incubated on a thermoshaker at 37° C. for 30 min with 100 μL of $^{11}$C-3 solution (210±79 MBq/nmol; 2.4±1.1 pmol/assay) and increasing concentrations of unlabeled 3 in buffer B (100 μL). Nonspecific binding was defined as the residual binding observed in the presence of 1 mM levetiracetam (100 μL). At completion of the incubation period, the membrane-bound radioligand was recovered using rapid filtration through GF/B glass fiber filters (13 mm GD/X, Whatman Inc.) that were pre-soaked for more than 30 min in 0.5% polyethyleneimine (PEI). The membranes were washed twice with 1 ml of ice-cold buffer B. The binding mixtures, filters and filtrates were counted in a γ-counter (Wizard; Perkin-Elmer). Saturation of $^{11}$C-3 was calculated using a two-parameter hyperbolic equation in which $B=B_{max} \times [L]/(K_D+[L])$ where B is measured binding at concentration of ligand [L] with a density ($B_{max}$) and equilibrium constant ($K_D$). The $B_{max}$ in the centrum semiovale was fit using a fixed $K_D$ value of 3.9 nM.

Tissue of 12 brain regions was homogenized using a FastPrep instrument in lysis buffer containing, per mL: 200 μL of 10% sodium dodecyl sulfate (SDS), 100 μL of glycerol, 62.5 μL of 1 M Tris (pH 6.8), 100 μL of 10× protease inhibitor in water, 100 μL of 10× phosphatase inhibitor in water, and 437.5 μL of water. The protein concentrations were determined using the BCA method. For each brain region, 2 μg of protein per lane was loaded on 4-20% precast polyacrylamide gels (n=10 for SV2A, n=5 for SYN, and n=5 for β-actin). Proteins were separated by gel electrophoresis and transferred to PVDF membranes by electroblotting (Mini-PROTEAN system; Bio-Rad Laboratories). The membranes were blocked in tris-buffered-saline-tween 20 (TBST, 0.1%, v/v) containing 5% BSA for 1 h at room temperature, and then incubated overnight at 4° C. with primary antibodies (rabbit anti-SV2A, ab32942, 1:10,000, Abcam; mouse anti-SYN, s5768, 1:500, Sigma-Aldrich; mouse anti-β-actin, ab6276, 1:5000, Abcam). The membranes were washed in TBST for ~15 min, before incubation for 1 h at room temperature with secondary antibodies conjugated with horseradish peroxidase (anti-rabbit, 711-035-152, 1:10,000 Jackson ImmunoResearch Laboratories; anti-mouse, 715-035-150, 1:10,000 Jackson ImmunoResearch Laboratories). Membranes were washed in TBST for ~15 min, before visualization of the immunoreactivity bands by chemiluminescence using Clarity Western ECL substrate (Bio-Rad). Chemiluminescent intensities were measured on a Typhoon Trio Variable Mode Imager (GE Healthcare Life Sciences). To allow for normalization of the membranes between gels, on each gel a quality control sample (2 μg, temporal cortex) was included. Background optical density was subtracted from each band to ensure measurement of antibody-specific signal.

For fluorescent immunocytochemistry, a coronal tissue section of baboon brain containing somatosensory cortex was immersion fixed in 4% freshly depolymerized paraformaldehyde dissolved in 0.1 M phosphate buffer (pH 7.4) at 4° C. overnight. The next day the tissue was sectioned into 50-μm thick slices on a Vibratome and sections were stored in FD Tissue Cryoprotection Solution (FD Neuro-Technologies) at −20° C. On the experimental day, tissue sections were washed in TBST2 (TBS with 0.5% Triton-X-100) followed by incubation in 1M ethanolamine in 0.1 M phosphate buffer (pH 7.4) for quenching of aldehydes. Sections were washed again in TBST2, and then blocked for 1 h in 10% newborn calf serum+3% BSA in TBST2. The blocked sections were incubated with primary antibodies (anti-SV2A, 1:200; anti-SYN, 1:1000) overnight at room temperature. The next day, sections were washed in TBST2 and incubated with secondary fluorescent antibodies (goat anti-rabbit, Alexa Fluor 555, 1:1000, Abcam; goat anti-mouse, Alexa Fluor 488, 1:1000, Abcam) for 1 h at room temperature. Following washes in TBST2, the sections were mounted on gelatin coated slides using Vectashield with DAPI (Vector Laboratories). Images were acquired using a LEICA TCS SP5 confocal laser scanning microscope (Leica Microsystems).

Figure 8A:
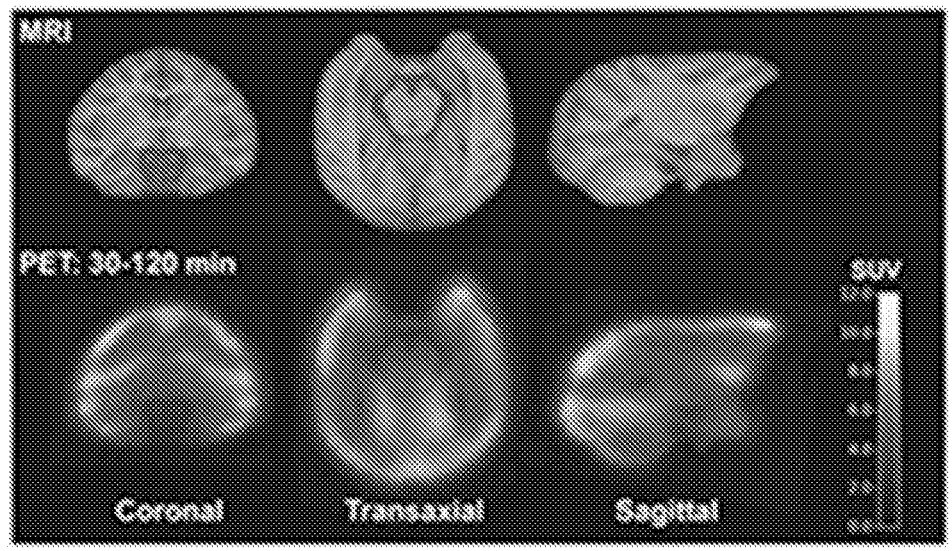
FIG. 8A shows template MRI and PET summation images of baboon brain from 30-120 min after i.v. injection of (R)-$^{18}$C-3.
Figure 8B:
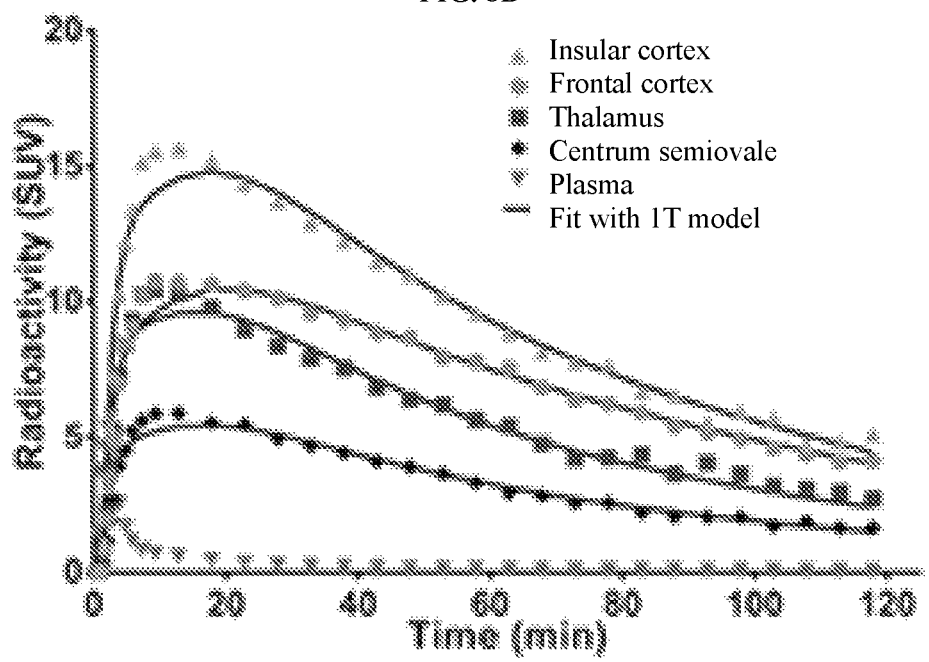
FIG. 8B is a graph depicting time-activity curves of regional brain radioactivity in the insular cortex, frontal cortex, thalamus, and centrum semiovale and (R)-$^{18}$C-3 plasma concentration. The solid lines show curve fitting with the 1-tissue (1T) compartment model.

To validate $^{11}$C-3 as a marker of synaptic density, a PET measurement in an olive baboon (*Papio anubis*) was performed, after which the animal was sacrificed and the brain dissected for post-mortem tissue studies. Following injection of $^{11}$C-3, brain uptake was rapid, with highest radioactivity concentrations in the cerebral cortex and lowest in the white matter region centrum semiovale (FIGS. 8A-8B). Regional time-activity curves displayed rapid kinetics, with peak uptake of 10-15 (standardized uptake value, SUV, activity normalized to injection dose and body weight) in gray matter regions achieved within 6-16 min after injection. Regional volume of distribution ($V_T$) values, a measure of equilibrium binding, were estimated with the 1T model and were in accordance with previously reported $V_T$ values ($V_T$ rhesus=1.86×$V_T$ baboon-0.0123; $R^2$=0.87).

Figure 8C:
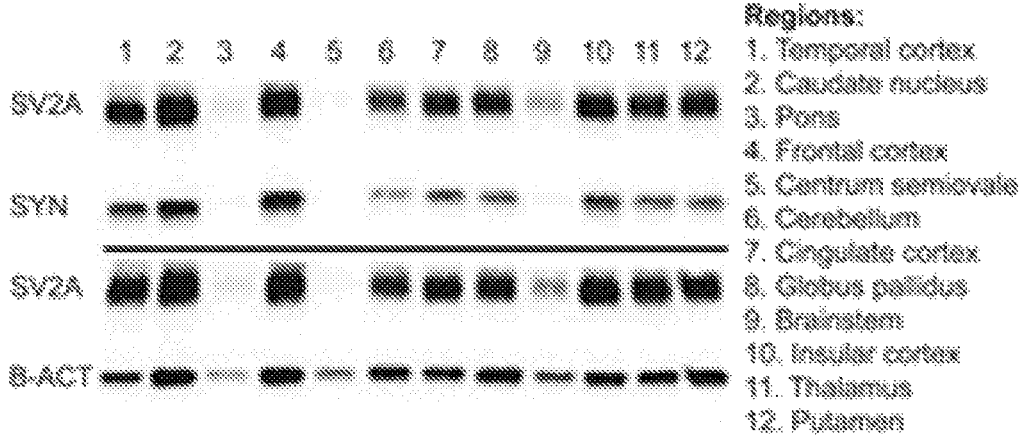
FIG. 8C depicts Western blot analyses of twelve baboon brain regions. Western blot was performed with a polyclonal anti-SV2A antibody (83 kDa, top and bottom), a monoclonal anti-synaptophysin (SYN) antibody (38 kDa, top), and a monoclonal anti-beta actin antibody (42 kDa, bottom). For each brain region, individual wells were loaded with 2 jag protein.
Figure 8D:
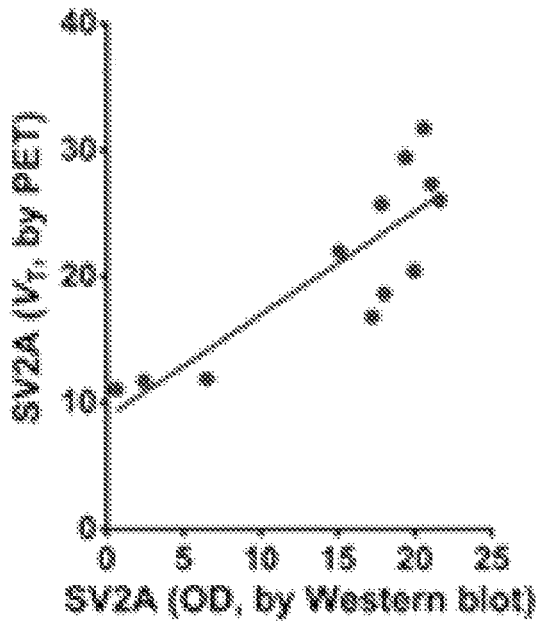
FIG. 8D is a graph that depicts the correlation between regional SV2A density in vitro (by Western blot) and in vivo (by PET measurement). Data are from 12 baboon brain regions.
Figure 8E:
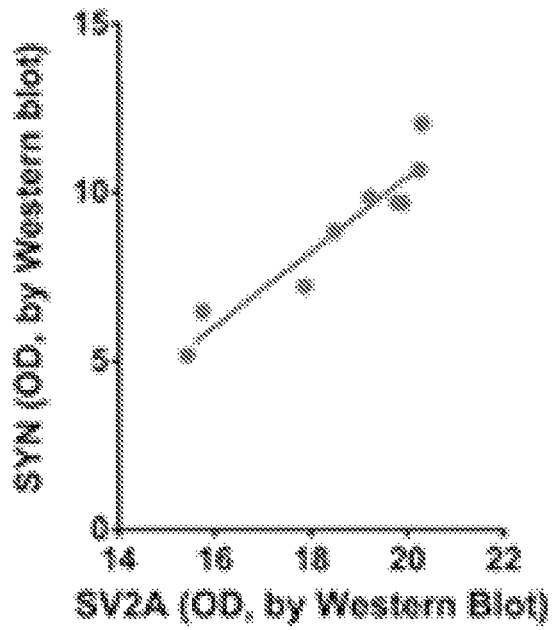
FIG. 8E is a graph that depicts the correlation between in vitro SV2A and in vitro synaptophysin (SYN) density in gray matter regions determined using Western blot analyses. Data are from 9 baboon brain regions.

Tissues were sampled from 12 regions of the baboon brain and analyzed by Western blotting and SV2A homogenate binding assays. To determine if SV2A can, like the gold standard SYN, be used as a marker of synaptic density, regional densities of SV2A and SYN were compared using selective antibodies for SV2A, SYN, and the housekeeping protein β-actin. SV2A and SYN signals were strong and specific in all gray matter regions, but absent or weak in the centrum semiovale (FIG. 8C). The in vitro regional distribution of SV2A (optical density, OD) correlated well with in vivo PET-measured $^{11}$C-3 $V_T$ (FIG. 8D). Importantly, there was an excellent linear correlation between SV2A and SYN across all gray matter regions analyzed (FIG. 8E), indicating that SV2A can be used as an alternative to SYN for accurate synapse quantification.

Figure 8F:
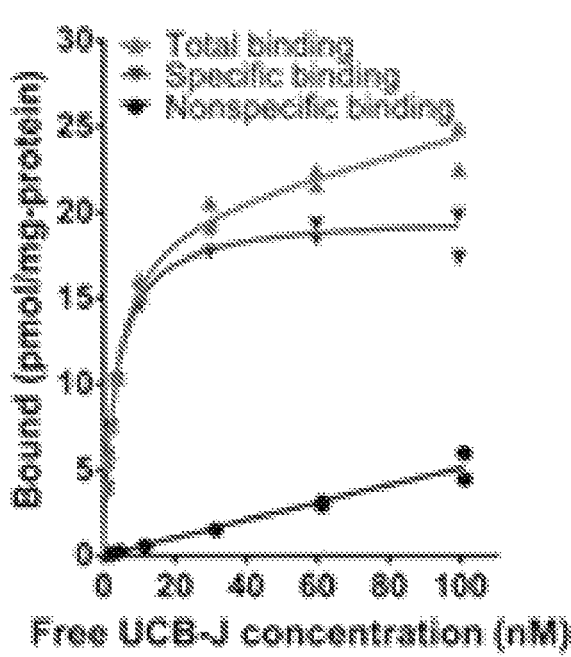
FIG. 8F is a graph that depicts saturation studies of (R)-[11]C-3 that were performed for 12 baboon brain regions. Data are for the temporal cortex. Each measurement was performed in duplicate. Membranes were incubated with increasing concentrations of 3 for 30 min at 37° C. Nonspecific binding was determined as the residual binding measured in the presence of 1 mM levetiracetam. Specific binding was determined by subtraction of the nonspecific from the total binding.
Figure 8G:
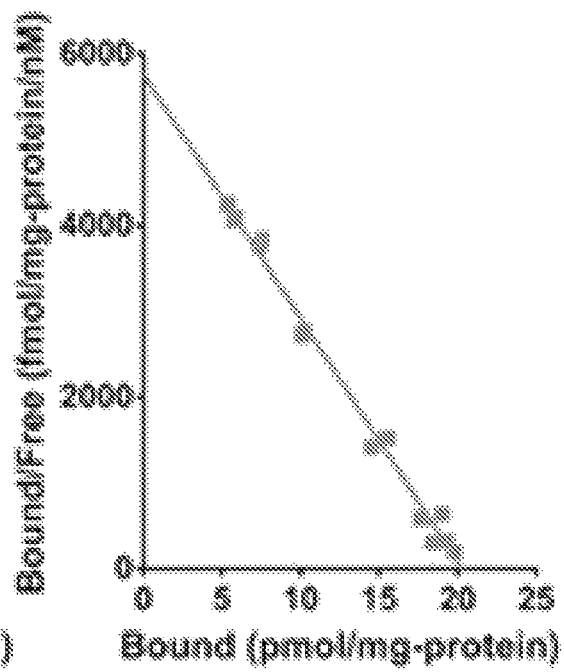
FIG. 8G is a Scatchard plot from the transformed data of the temporal cortex in FIG. 8F.
Figure 8H:
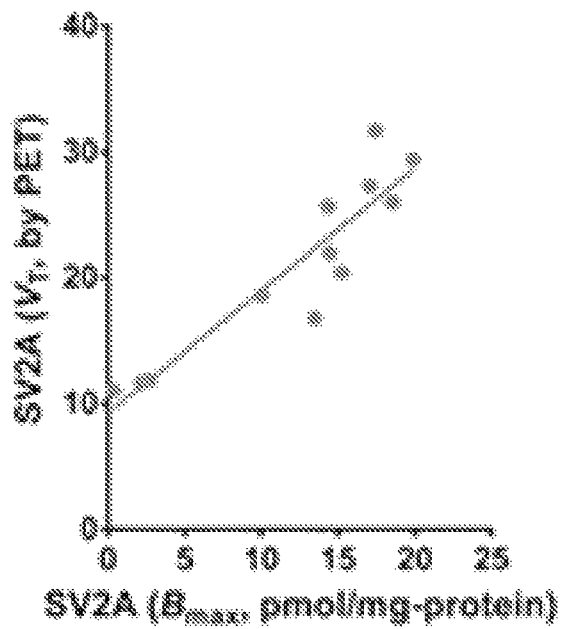
FIG. 8H is a graph that depicts the correlation between regional SV2A density ($B_{max}$) measured in vitro using tissue homogenate binding with (R)-[11]C-3 and regional (R)-[11]C-3 binding measured in vivo in a baboon using PET. Data are from 12 brain regions.
Figure 8I:
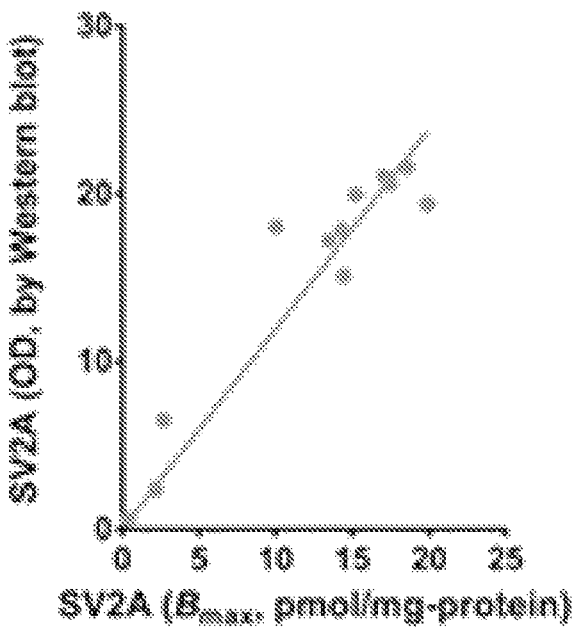
FIG. 8I is a graph that depicts the correlation between regional SV2A density ($B_{max}$) measured in vitro using tissue homogenate binding and SV2A density using in vitro Western blot analyses (optical density, OD). Data are from 12 baboon brain regions.

To further evaluate the relationship between in vivo $^{11}$C-3 binding and SV2A density, homogenate binding studies were performed to determine affinity ($K_D$) and regional SV2A densities ($B_{max}$). Saturation studies using $^{11}$C-3 were conducted for 12 brain regions in a competition binding assay. $^{11}$C-3 bound with an average $K_D$ of 3.9±0.6 nM (Mean±SD, n=11) to a homogeneous population of binding sites, as illustrated in the temporal cortex, the region with the highest SV2A density (FIG. 8F-8G). The regional SV2A $B_{max}$ ranged from 2.2 pmol/mg-protein (111 pmol/mL-brain tissue) in the pons to 19.9 pmol/mg-protein (918 pmol/mL-brain tissue) in the temporal cortex; specific binding could not be reliably detected in the centrum semiovale. The in vitro $B_{max}$ values also correlated well with the in vivo $V_T$ values measured in baboon (FIG. 8H). There was excellent correlation between the in vitro $B_{max}$ derived from homogenate binding and the regional SV2A Western blot measurements (FIG. 8I).

Figure 8J:
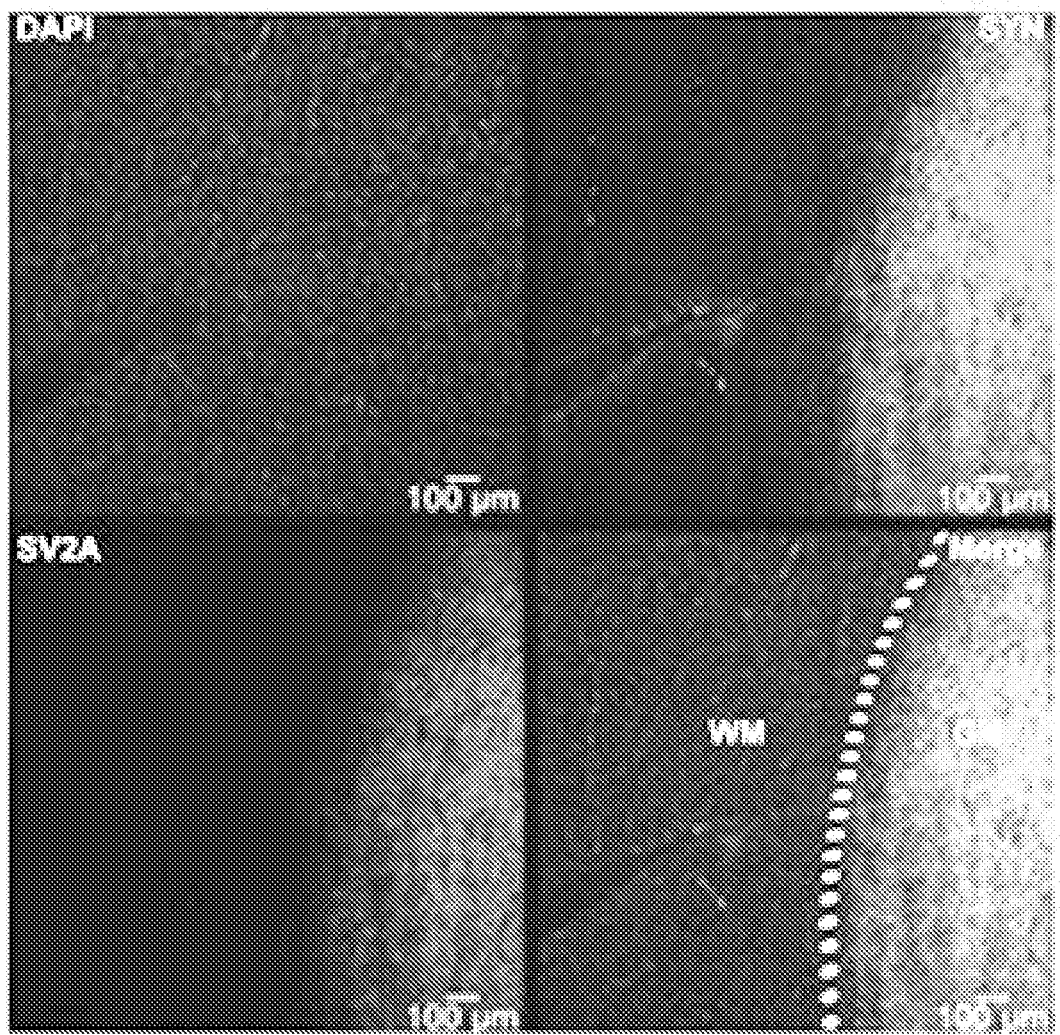
FIG. 8J is a low-power confocal microscopy image of 4′,6-diamidino-2-phenylindole (DAPI), SYN and SV2A in white matter and cortical gray matter of the baboon brain. The dotted white line indicates the border between the white matter (WM, left) and the gray matter (GM, right).
Figure 8K:
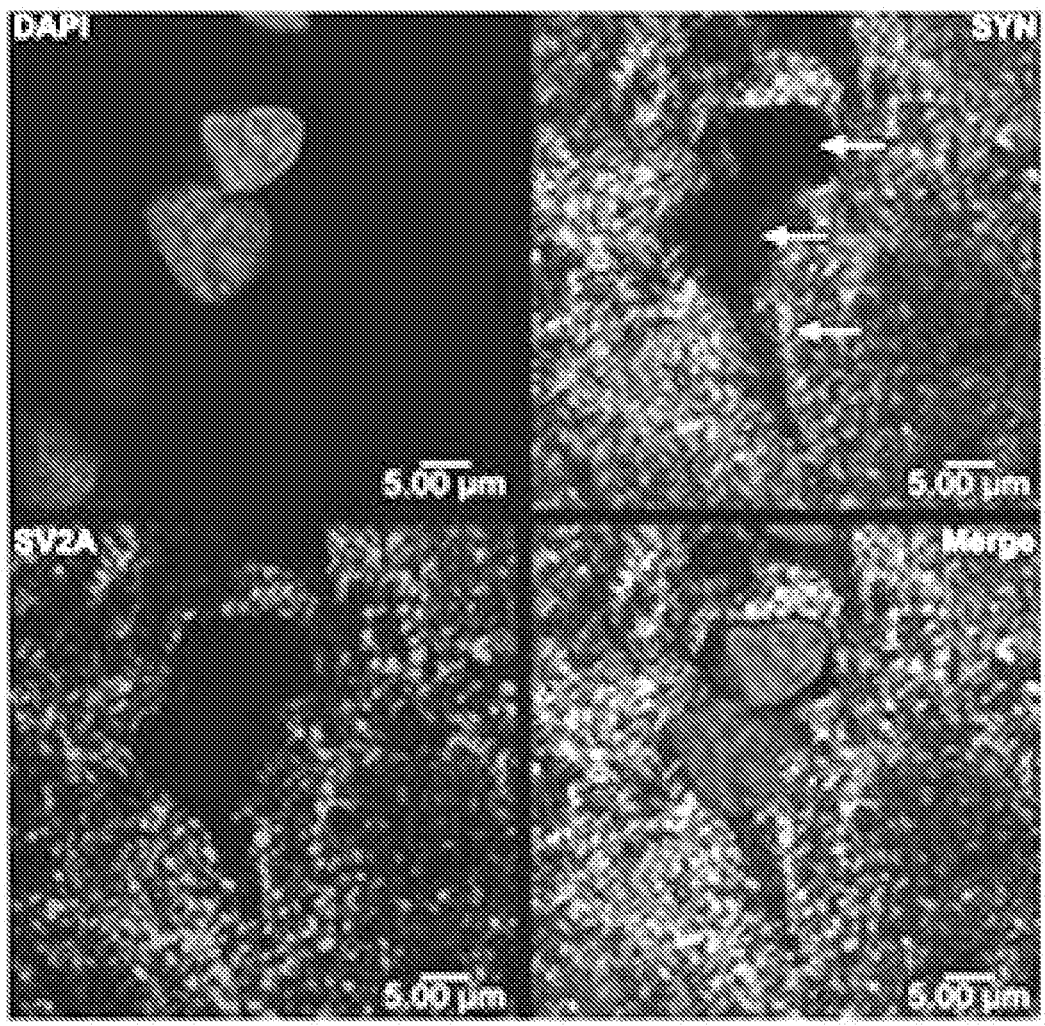
FIG. 8K is a high-power confocal microscopy image of DAPI, SYN and SV2A in the gray matter of the baboon brain from FIG. 8J. Labeling for SYN and SV2A is evident as punctate staining in the neuropil, particularly surrounding neuronal cell bodies and proximal dendrites (arrow), but absent in neuronal cell bodies (white arrows). Nuclei are indicated by the DAPI stain.

To evaluate the cellular distribution of SV2A, the localization of SV2A and SYN was compared using selective antibodies. Immunoreactivity was evaluated in a section of the somatosensory cortex and the adjacent white matter using confocal microscopy (FIGS. 8J-8K). There was considerable overlap between the staining for SYN and SV2A. SV2A and SYN staining was negligible in the white matter, but high in the gray matter (FIG. 8J). SV2A and SYN staining was absent in neuronal cell bodies (white arrows in FIG. 8K), but high at the border of a proximal dendrite (yellow arrow in FIG. 8K). These data further support SV2A as an alternative to SYN for synapse quantification.

Example 5: Use of SV2A PET Imaging to Detect Changes of Synaptic Density Under Disease Conditions PET imaging with (R)-$^{11}$C-3 was performed in healthy human subjects and patients with various disorders to determine if SV2A imaging can be used as an in vivo biomarker to detect changes in synaptic density in human diseases. PET scans were carried out on the Siemens High Resolution Research Tomograph (HRRT) for 90-120 min after injection of the radiotracer with typical radioactivity dose of 5-20 mCi. Procedures for PET image acquisition, arterial blood sampling for metabolite analysis and input function measurement, PET image processing, drawing of regions of interest (ROIs), generation of brain regional time activity curves (TACs), and kinetic analysis of imaging data to derive binding parameters ($V_T$ and $BP_{ND}$) were similar to those described in Examples 3-4.

PET Imaging with (R)-$^{11}$C-3 in Patients with Epilepsy.

Figure 9A:
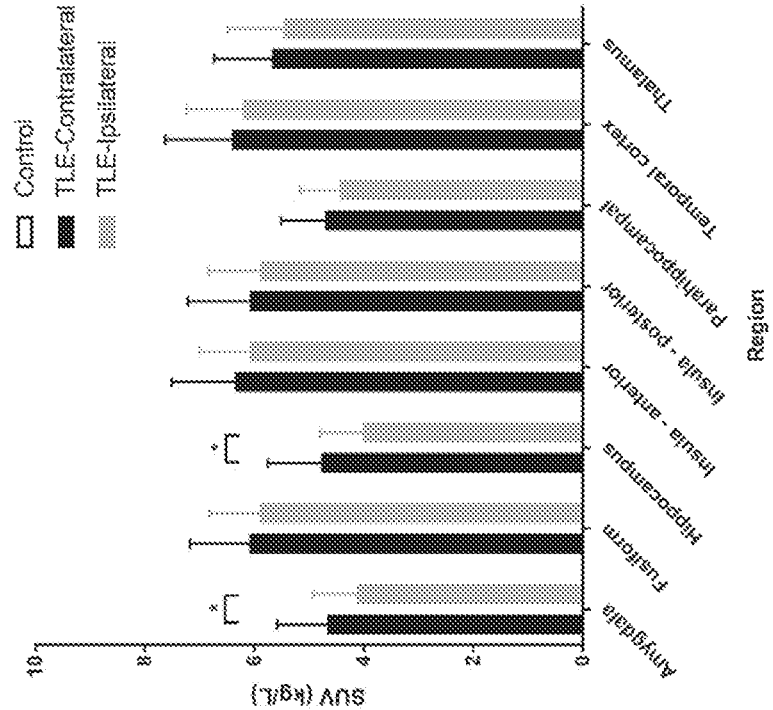
FIG. 9A is a graph depicting the regional binding potential ($BP_{ND}$) values of (R)-[11]C-3 in selected brain regions of ten healthy control subjects and nine temporal lobe epilepsy (TLE) patients with mesial temporal sclerosis (MTS).
Figure 9B:
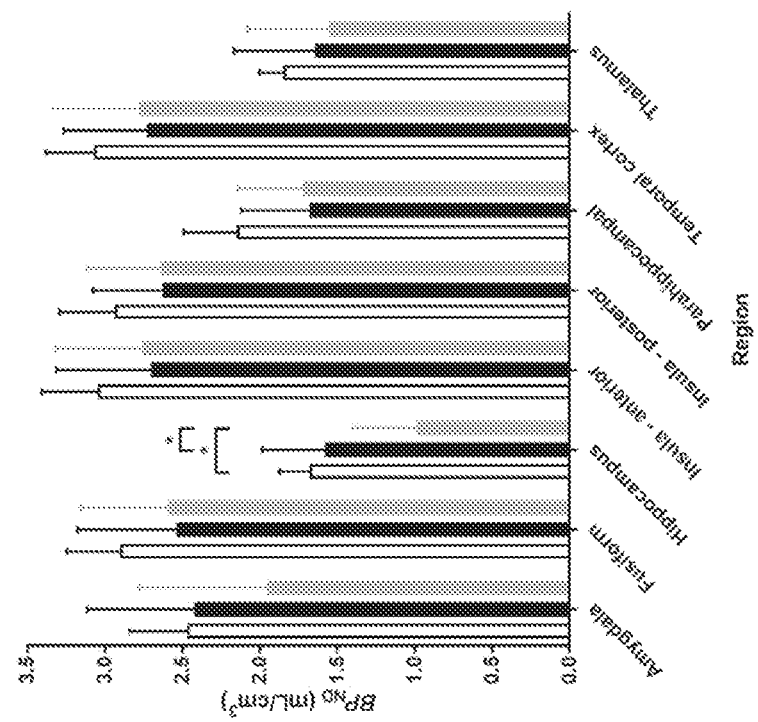
FIG. 9B is a graph depicting the regional standard uptake values (SUV) of $^{18}$F-FDG in the ipsilateral and contralateral sides of selected brain regions of nine TLE patients with MTS. * indicates p<0.05.
Figure 9C:
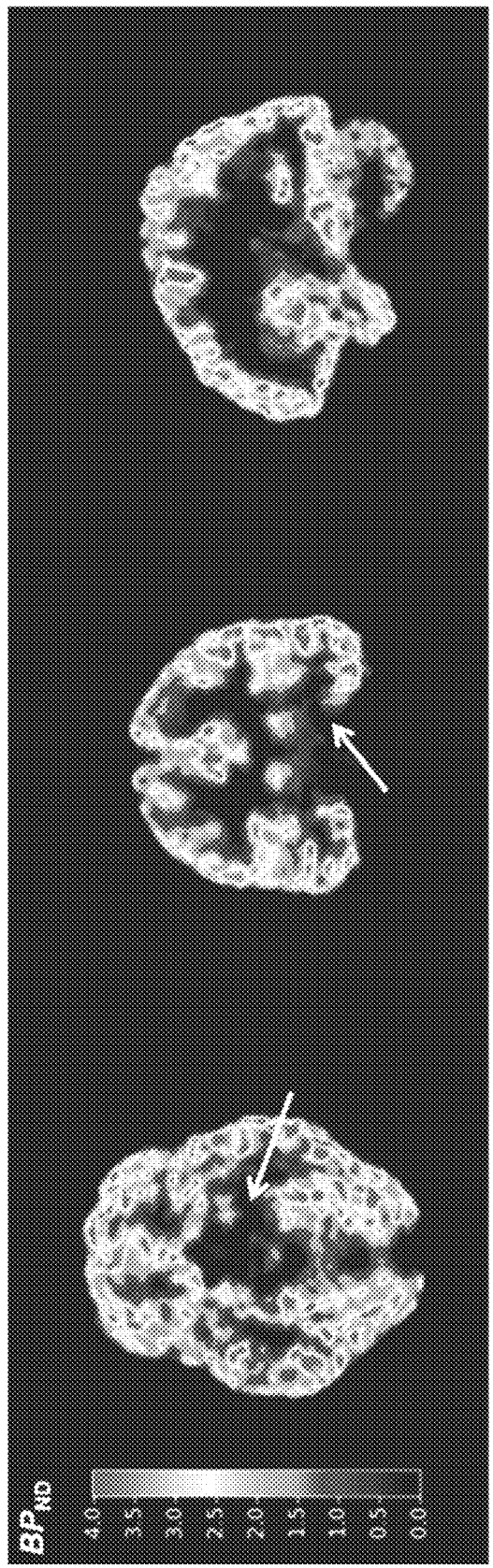
FIG. 9C are representative parametric (R)-[11]C-3 $BP_{ND}$ images of a medial temporal lobe epilepsy (MTLE) patient, with arrow showing a reduction in the hippocampus.

PET imaging with (R)-$^{11}$C-3 was carried out in ten healthy control subjects and nine patients of temporal lobe epilepsy (TLE) with mesial temporal sclerosis (MTS). In nine TLE subjects with MTS seen on MRI, (R)-$^{11}$C-3 $BP_{ND}$ asymmetry indices were −38±21% in the hippocampus, with very limited asymmetry in other brain regions. Reductions in (R)-$^{11}$C-3 $BP_{ND}$ values were restricted to the sclerotic hippocampus when compared to healthy control subjects. The corresponding asymmetry in hippocampal $^{18}$F-FDG uptake was −16±5% and the asymmetry magnitudes correlated with (R)-$^{11}$C-3 binding across subjects (r=0.91). The asymmetries in (R)-$^{11}$C-3 binding were 2.3-fold larger than for $^{18}$F-FDG. These results indicate that (R)-$^{11}$C-3 binding is reduced in the seizure onset zone of subjects with TLE and MTS. Hence, PET imaging of SV2A may be a promising biomarker approach in the presurgical selection and evaluation of TLE patients, and may improve the sensitivity of molecular imaging for seizure focus detection in patients with epilepsy. Shown in FIG. 9 are regional $BP_{ND}$ values of (R)-$^{11}$C-3 (FIG. 9A) and standardized uptake values (SUV) of $^{18}$F-FDG (FIG. 9B) in ten healthy control subjects and nine patients of TLE with MTS, along with representative (R)-$^{11}$C-3 parametric images of a subject with medial temporal lobe epilepsy (FIG. 9C).

PET Imaging with (R)-$^{11}$C-3 in Patients with AD Dementia and Mild Cognitive Impairment (MCI).

PET imaging with (R)-$^{11}$C-3 was performed in 10 patients with AD or MCI and 11 age-matched cognitively normal (CN) healthy subjects. Patients with AD/MCI spanned the disease stages from amnestic Mild Cognitive Impairment (MCI, n=5) to mild dementia (n=5) and were all confirmed β-amyloid positive (Aβ+) by $^{11}$C-Pittsburgh Compound B ($^{11}$C-PiB) PET imaging indicating the presence of the AD pathological biomarker protein aggregates. CN subjects were all confirmed Aβ negative by $^{11}$C-PiB PET imaging, i.e., without deposition of plaques. (R)-$^{11}$C-3 total uptake (volume of distribution, $V_T$) and specific binding (binding potential, $BP_{ND}$) were measured in brain regions of interest (ROIs). When compared to CN subjects, Patients with AD/MCI displayed significant reduction (41%) in hippocampal SV2A binding as assessed by (R)-$^{11}$C-3 $BP_{ND}$ (P=0.005) and $V_T$ (28% reduction, P=0.001). These reductions persisted after correction for tissue loss, i.e., partial volume correction ($BP_{ND}$: P=0.020, $V_T$: P=0.056). Exploratory analyses of other brain ROIs and statistical parametric mapping (SPM) also revealed reductions in entorhinal cortex. Hippocampal SV2A binding was correlated with a composite episodic memory score in the overall sample. Results from this study indicate that PET imaging of SV2A may provide a direct measure of synaptic density in AD/MCI and therefore holds promise as an in vivo biomarker for AD, and as an outcome measure in trials of disease-modifying therapies for AD, particularly those targeted at the preservation and restoration of synapses.

Shown in FIG. 10 are (R)-$^{11}$C-3 parametric PET ($V_T$) images in CN subjects (FIG. 10A), and patients with MCI (FIGS. 10B & 10C) and mild AD dementia (FIGS. 10D & 10E). The pseudo-color in PET images represents the intensity of (R)-$^{11}$C-3 binding ($V_T$). Evident reduction of (R)-$^{11}$C-3 binding in the hippocampus of patients with AD/MCI is noted as compared to CN (arrow denotes the right hippocampus). Various degrees of reduction can also be visualized in the temporoparietal cortex of patients with MCI (FIGS. 10B & 10C) and mild AD dementia (FIG. 10D) and the right temporal cortex of patient with mild AD dementia (FIG. 10E). Whole brain SPM analysis with $V_T$ values from mild AD patients (n=9) with CN subjects (n=8) (FIG. 10F) shows the clearest reductions in the hippocampal region. Blue color indicates the regions with statistically significant reduction of $V_T$ in patients with AD/MCI compared to CN subjects, rendered on brain surfaces at different projections.

PET Imaging with (R)-$^{11}$C-3 in Patients with Parkinson's Disease (PD).

Figure 11:
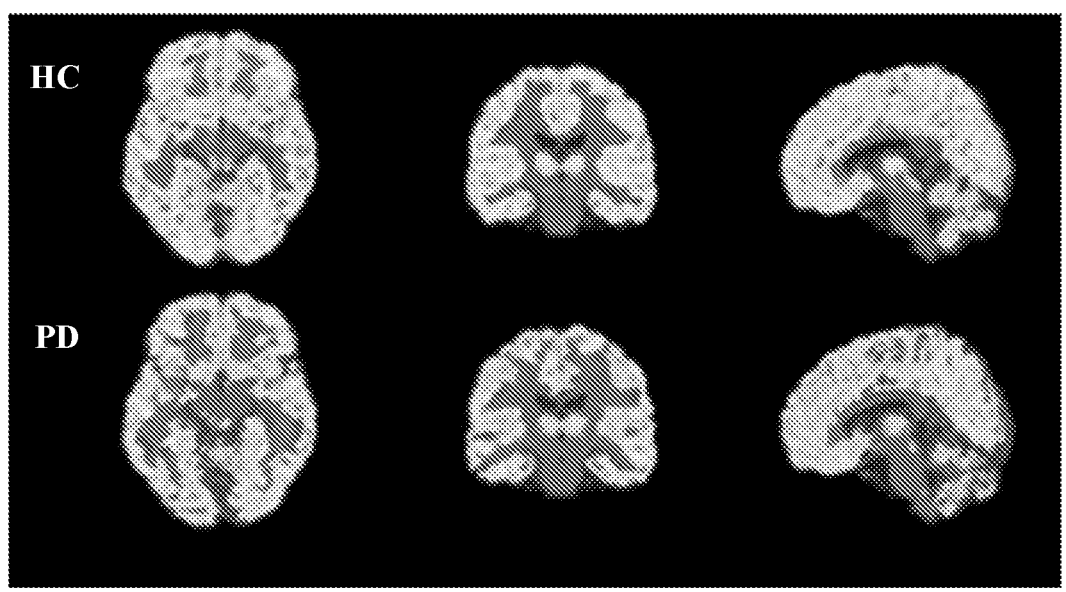
FIG. 11 are parametric PET ($V_T$) images of (R)-[11]C-3 in a representative healthy control subject (top row) and a patient with Parkinson's disease (PD) (bottom row). Reductions in (R)-[11]C-3 $V_T$ are seen across all brain regions, with the most pronounced reductions in the cortical regions (19%-23% decreases), and in the substantia nigra and putamen (19% and 15% decreases, respectively).

PET imaging with (R)-$^{11}$C-3 was conducted in two PD subjects (50 and 43 years old females with clinical onset 10 and 4 years ago). When compared with age-matched healthy control subjects (56 and 42 years old females), reductions in (R)-$^{11}$C-3 $V_T$ were seen across all brain regions, with the most pronounced reductions in cortical regions (19-23% decreases), and in the substantia nigra (SN) and putamen (19% and 15% decreases, respectively). (R)-$^{11}$C-3 $BP_{ND}$ values were also similarly reduced with decreases of 16%-20% in the cortical regions, and 33% and 16% decreases in the SN and putamen, respectively. These preliminary results suggest that synaptic density, as measured by SV2A PET imaging, is dramatically altered throughout the brain of patients with PD, with large decreases in areas known to be involved in the disease process. Hence, SV2A PET imaging may be useful in the diagnosis of PD and in monitoring disease progression. Shown in FIG. 11 are parametric (R)-$^{11}$C-3 PET images ($V_T$) in a healthy control (top) and a PD patient (bottom).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound selected from the group consisting of:

3

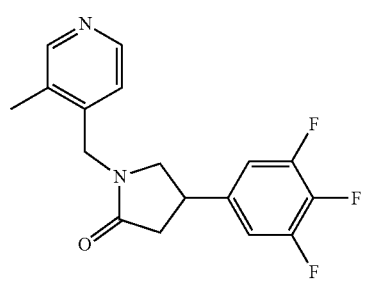

4

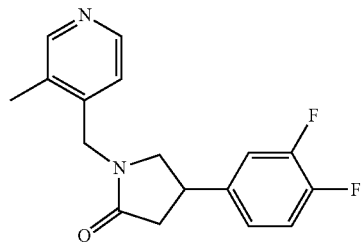

5

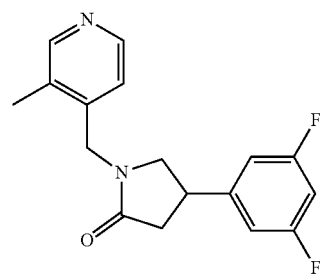

11

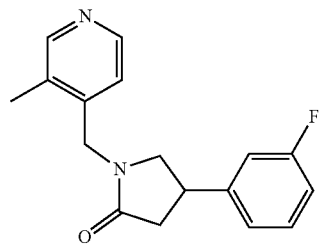

13

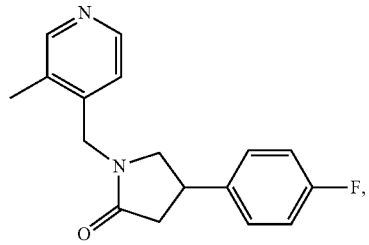

wherein:

at least one instance of F in the compound is $^{18}$F;

or a salt, solvate, tautomer, or enantiomer thereof, or any mixtures thereof.

2. The compound of claim 1, which is in an enantiomerically enriched form.

3. The compound of claim 1, which is a single enantiomer that is essentially free of the corresponding other enantiomer.

4. A pharmaceutical composition comprising:
at least one compound selected from the group consisting of:

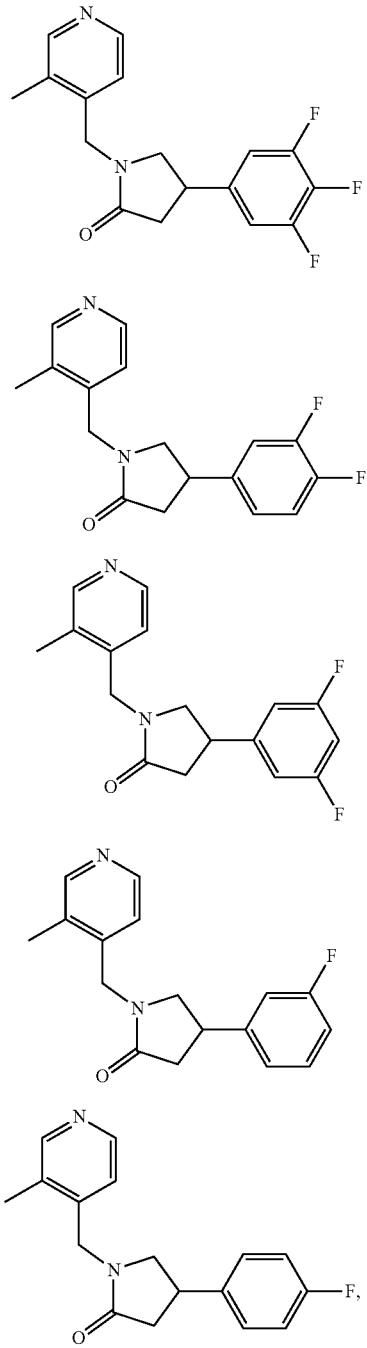

wherein at least one instance of F in the compound is $^{18}$F; and
at least one pharmaceutical excipient.

5. The composition of claim 4, which is formulated for intravenous delivery.

6. A method of decreasing the amount of unbound synaptic vesicle glycoprotein 2A (SV2A) in at least one region of the body of a subject, the method comprising administering to the subject at least one compound of claim 1.

7. A method of detecting or measuring the amount of SV2A in a subject's body, the method comprising:
administering to the subject at least one compound of claim 1, and
detecting the at least one compound bound to the at least one region of the body of the subject;
thereby detecting the amount of SV2A in the at least one region of the body of the subject.

8. A method of imaging at least one region of a subject's body, the method comprising:
administering to the subject at least one compound of claim 1; and
detecting the at least one compound by positron emission tomography (PET) in at least one region of the body of the subject;
thereby generating an image of the at least one region of the body of the subject.

9. A method of detecting or measuring synaptic density in at least one region of a subject's brain, the method comprising:
administering to the subject at least one compound of claim 1;
detecting the at least one compound by PET in the at least one region of the brain of the subject; and
determining a level of SV2A in the at least one region of the brain of the subject.

10. A method of detecting a disease or disorder involving synaptic disruptions or synaptic abnormalities or a metabolic disease or disorder in a subject's body, the method comprising:
administering to the subject at least one compound of claim 1;
detecting the at least one compound by PET in at least one region of the body of the subject;
determining a level of SV2A in the at least one region of the body of the subject, and comparing it to a control reference from a control subject who is not affected by the disease or disorder;
wherein, if the SV2A level in the at least one region of the subject's body is lower than in the control reference, the disease or disorder is detected in the subject.

11. A method of monitoring or evaluating effectiveness of treatment or therapy for a disease or disorder involving synaptic disruptions or synaptic abnormalities a metabolic disease or disorder in a subject's body, the method comprising:
administering to the subject at least one compound of claim 1;
detecting the at least one compound by PET in at least one region of the body of the subject;
determining a level of SV2A in the at least one region of the body of the subject, and comparing it to a control reference from the subject before receiving the therapy or treatment; wherein, if the SV2A level in the at least one region of the body of the subject is higher than in the control reference, the treatment or therapy is at least partially effective for the subject.

12. The method of claim 10, wherein the disease or disorder is at least one selected from the group consisting of Alzheimer's disease (AD), Parkinson's disease (PD), multiple sclerosis (MS), autism, epilepsy, stroke, traumatic brain injury (TBI), psychiatric disorder, and diabetes.

13. The method of claim 12, wherein the disease or disorder is AD.

14. The method of claim 13, wherein the AD is pre-clinical or prodromal AD.

15. The method of claim 12, wherein the psychiatric disorder comprises depression, schizophrenia, post-traumatic stress disorder (PTSD), or substance abuse disorder.

16. The method of claim 12, wherein the disease or disorder is diabetes.

17. A method of detecting or measuring a seizure onset zone in a subject with epilepsy, stroke, traumatic brain injury, Parkinson's disease, or autism, the method comprising:
administering to the subject at least one compound of claim 1;
detecting the at least one compound by PET in at least one region of the brain of the subject;
determining a level of SV2A in the at least one region of the brain of the subject, whereby, if an area within the at least one region has lower SV2A level than the rest of the at least one region, the area is identified as a seizure onset zone.

18. A method of detecting an ischemic area in a subject with stroke, the method comprising:
administering to the subject at least one compound of claim 1;
detecting the at least one compound by PET in at least one region of the brain of the subject;
determining a level of SV2A in the at least one region of the brain of the subject, whereby, if an area within the at least one region has lower SV2A level than the rest of the at least one region, the area is identified as being ischemic.

19. The method of claim 6, wherein the region of the subject's body is a region of the brain comprising at least one selected from the group consisting of cingulate cortex, frontal cortex, insular cortex, nucleus accumbens, occipital cortex, temporal cortex, putamen, caudate nucleus, thalamus, cerebellum, hippocampus, globus pallidus, amygdala, brainstem, pons, and centrum semiovale.

20. The method of claim 16, wherein the region of the subject's body comprises a region of the pancreas.

* * * * *